(12) United States Patent
Penner

(10) Patent No.: US 8,195,297 B2
(45) Date of Patent: Jun. 5, 2012

(54) DEVICES AND METHODS FOR ELECTRICAL STIMULATION OF THE DIAPHRAGM AND NERVES

(75) Inventor: Abraham Penner, Tel Aviv (IL)

(73) Assignee: E-Pacing, Inc., Wilmington, DE (US)

(*) Notice: Subject to any disclaimer, the term of this patent is extended or adjusted under 35 U.S.C. 154(b) by 322 days.

(21) Appl. No.: 12/578,370

(22) Filed: Oct. 13, 2009

(65) Prior Publication Data

US 2010/0094376 A1  Apr. 15, 2010

Related U.S. Application Data

(60) Provisional application No. 61/104,908, filed on Oct. 13, 2008.

(51) Int. Cl.
*A61N 1/00* (2006.01)
(52) U.S. Cl. .......................................................... 607/42
(58) Field of Classification Search .................. 607/2, 3, 607/42
See application file for complete search history.

(56) References Cited

U.S. PATENT DOCUMENTS

| | | |
|---|---|---|
| 4,090,518 A | 5/1978 | Elam |
| 4,156,429 A | 5/1979 | Amundson |
| 4,198,963 A | 4/1980 | Barkalow et al. |
| 4,351,330 A | 9/1982 | Scarberry |
| 4,574,807 A | 3/1986 | Hewson et al. |
| 4,640,298 A | 2/1987 | Pless et al. |
| 4,735,206 A | 4/1988 | Hewson |
| 4,817,611 A | 4/1989 | Arzbaecher et al. |
| 4,960,133 A | 10/1990 | Hewson |
| 5,056,532 A | 10/1991 | Hull et al. |
| 5,170,803 A | 12/1992 | Hewson et al. |
| 5,179,952 A | 1/1993 | Buinevicius et al. |
| 5,230,337 A | 7/1993 | Dahl et al. |
| 5,307,818 A | 5/1994 | Segalowitz |
| 5,379,765 A | 1/1995 | Kajiwara et al. |
| 5,387,232 A | 2/1995 | Trailer |
| 5,417,713 A | 5/1995 | Cohen |
| 5,556,425 A | 9/1996 | Hewson et al. |

(Continued)

FOREIGN PATENT DOCUMENTS

WO  WO 2005/053788 A1  6/2005

(Continued)

OTHER PUBLICATIONS

International Searching Authority, "International Preliminary Report on Patentability," PCT Application No. PCT/US2008/064998, mailed Jul. 10, 2009.

(Continued)

*Primary Examiner* — Scott Getzow
(74) *Attorney, Agent, or Firm* — Sutherland Asbill & Brennan LLP

(57) ABSTRACT

Medical devices, systems, and methods are provided for providing respiratory therapy by electrically stimulating the phrenic nerves and/or the thoracic diaphragm. In one embodiment, at least one electrode is deployed to a position within the patient's airway and placed in proximity to a phrenic nerve or to the diaphragm. The electrode may be attached to a controller housing including a pulse generator using one or more electrical lead or leads or may be in wireless communication with the pulse generator. The controller housing may be implanted at a position within the patient or the controller housing may reside external to the patient.

11 Claims, 33 Drawing Sheets

U.S. PATENT DOCUMENTS

| | | | |
|---|---|---|---|
| 5,626,618 | A | 5/1997 | Ward et al. |
| 5,678,535 | A | 10/1997 | DiMarco |
| 5,902,330 | A | 5/1999 | Ollivier et al. |
| 6,056,532 | A | 5/2000 | Pagel |
| 6,148,222 | A | 11/2000 | Ramsey, III |
| 6,223,079 | B1 | 4/2001 | Bakels et al. |
| 6,249,316 | B1 | 6/2001 | Anderson |
| 6,283,988 | B1 * | 9/2001 | Laufer et al. .................... 607/96 |
| 6,415,183 | B1 | 7/2002 | Scheiner et al. |
| 6,473,640 | B1 | 10/2002 | Erlebacher |
| 6,532,388 | B1 * | 3/2003 | Hill et al. ......................... 607/2 |
| 6,574,506 | B2 | 6/2003 | Kramer et al. |
| 6,735,471 | B2 | 5/2004 | Hill et al. |
| 6,778,854 | B2 | 8/2004 | Puskas |
| 7,085,606 | B2 | 8/2006 | Flach et al. |
| 7,158,838 | B2 | 1/2007 | Seifert et al. |
| 7,183,837 | B2 | 2/2007 | Fujiwara |
| 7,231,249 | B2 | 6/2007 | Mower |
| 7,340,299 | B2 | 3/2008 | Puskas |
| 7,840,281 | B2 * | 11/2010 | Kveen et al. .................. 607/126 |
| 2003/0074039 | A1 | 4/2003 | Puskas |
| 2003/0130702 | A1 | 7/2003 | Kramer et al. |
| 2003/0195575 | A1 | 10/2003 | Kramer et al. |
| 2003/0225402 | A1 | 12/2003 | Stevens et al. |
| 2003/0236557 | A1 | 12/2003 | Whitehurst et al. |
| 2005/0015132 | A1 | 1/2005 | Kronzon |
| 2005/0043765 | A1 | 2/2005 | Williams et al. |
| 2006/0025654 | A1 | 2/2006 | Suzuki et al. |
| 2006/0069413 | A1 | 3/2006 | Imran |
| 2006/0130830 | A1 | 6/2006 | Barry |
| 2006/0224225 | A1 | 10/2006 | Ransbury et al. |
| 2007/0074728 | A1 | 4/2007 | Rea |
| 2008/0046016 | A1 * | 2/2008 | Ben-David et al. ............... 607/6 |
| 2008/0071317 | A1 | 3/2008 | Stahmann et al. |
| 2008/0125828 | A1 | 5/2008 | Ignagni |
| 2008/0177190 | A1 * | 7/2008 | Libbus et al. ................. 600/509 |
| 2008/0312712 | A1 | 12/2008 | Penner |
| 2008/0312725 | A1 | 12/2008 | Penner |

FOREIGN PATENT DOCUMENTS

| | | | |
|---|---|---|---|
| WO | WO 2006/034400 | A2 | 3/2006 |
| WO | WO 2006/115772 | A2 | 11/2006 |
| WO | WO 2008/092246 | A1 | 8/2008 |
| WO | WO 2009/029172 | A1 | 3/2009 |

OTHER PUBLICATIONS

International Preliminary Report on Patentability dated Dec. 17, 2009 for International Application No. PCT/US2008/066571.

International Search Report for PCT/US2008/064998 dated Sep. 25, 2008 (4 pages).

International Search Report for PCT/US2008/066571 dated Sep. 25, 2008 (4 pages).

Super Dimension, "InReach System", http://www.superdimension.com, (NDN).

Boston Scientific, "UltraFlex Esophageal NG Stent System", http://www.bostonscientific.com, (NDN).

Super Dimension, "InReach Expanding the Boundaries of Pulmonary Care", http://www.superdimension.com, Dec. 3, 2007.

Boston Scientific, "Polyflex Esophageal Stent", http://www.bostonscientific.com, 2005.

Mediguide, "Medical Positioning System gMPS", http://www.mediguide.co.il, (NDN).

Gammage, "Electrophysiology Temporary Cardiac Pacing", Heart, 2000, 715-720, vol. 83.

Goldstein, "Unipolar Bronchial Electrocardiographic Exploration of the Heart in Man: A Preliminary Report", Circulation, 1951, 911-922, vol. 3.

Langner, "Intrabronchial Electrocardiography: A Preliminary Report", Circulation, 1950, 419-421, vol. 2.

Ypenburg, "Intrathoracic Impedance Monitoring to Predict Decompensated Heart Failure", American Journal of Cardiology, vol. 99, 554-557, (NDN).

Wallace, "Endotracheal Cardiac Output Monitor", Anesthesiology, 2000, Abstract.

Ayas et al., "Prevention of Human Diaphragm Atrophy with Short Periods of Electrical Stimulation," Brief Communications; American Journal of Respiratory and Critical Care Medicine vol. 159, 1999.

R. Onders et al., "Diaphragm Pacing with Natural Orifice Transluminal Endoscopic Surgery: Potential for Difficult-to-Wean Intensive Care Unit Patients", Surg, (NDN).

John R. Elefteriades et al., "Pacing of the Diaphragm," Chapter-18: Techbooks [PPG-Quark], (NDN).

* cited by examiner

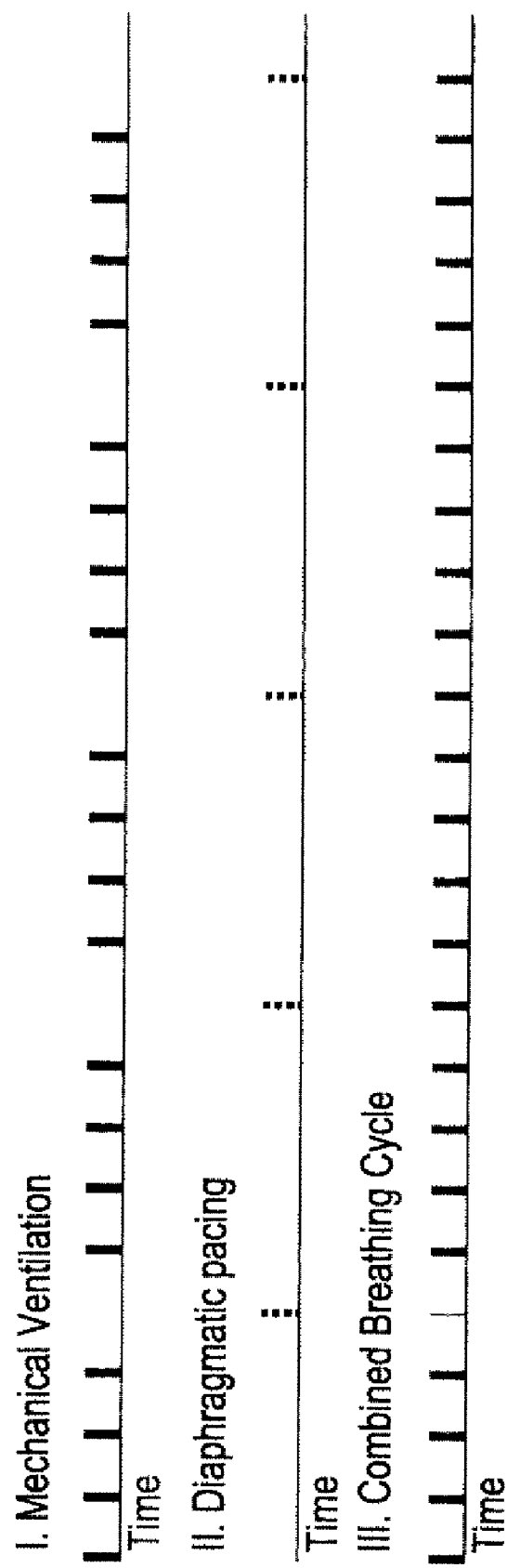

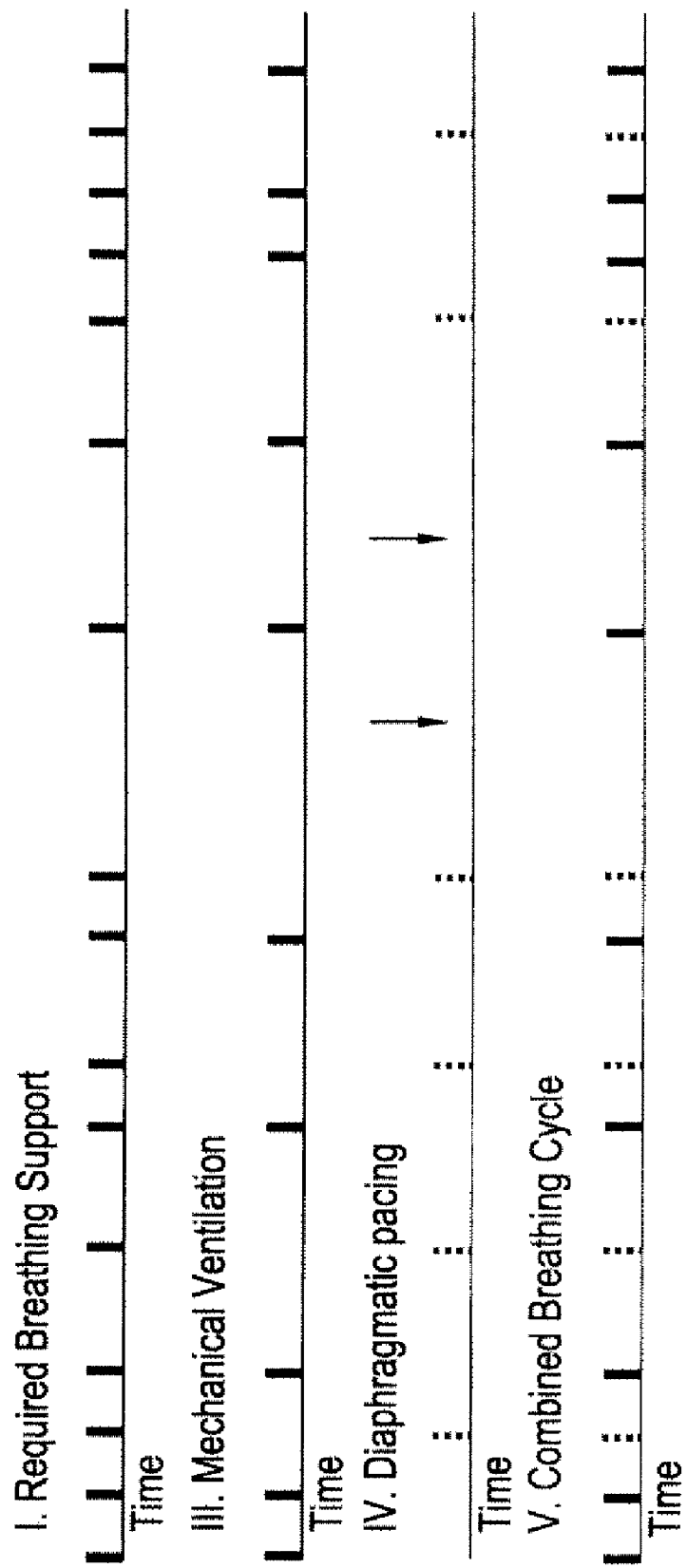

DEVICES AND METHODS FOR ELECTRICAL STIMULATION OF THE DIAPHRAGM AND NERVES

RELATED APPLICATION

This application claims priority to U.S. Provisional Application Ser. No. 61/104,908, entitled "Systems and Methods for Electrical Stimulation of the Diaphragm and Nerves," filed on Oct. 13, 2008, which is incorporated by referenced as if fully set forth herein.

BACKGROUND OF THE INVENTION

This invention is generally in the field of medical devices and treatment methods, and more particularly devices and methods for treating respiratory deficiencies with electrical stimulation.

A variety of medical disorders may prevent a patient from breathing normally in a spontaneous fashion and may require some external ventilation assistance. This disorder can last for a limited time, such as in anesthetized patients or in people after a serious surgery or as a result of a serious illness. In certain cases the need for ventilation assistance can last for a long time, such as in patients suffering from chronic illness including Spinal Cord Injury (SCI) or from Amyotrophic Lateral Sclerosis (ALS), or in Cheyne-Stokes respiration patients. A common acute ventilation assistance technique is performed by providing positive pressure mechanical ventilation via an intubation inserted to the patient trachea via the mouth, which works by increasing the pressure in the patient's airway and thus forcing additional air into the lungs. This technique, while being effective, suffers from several drawbacks and risks including ventilator-associated pneumonia, pneumothorax, airway injury, and alveolar damage among others. Prolonged use of mechanical ventilation may also cause the body to become dependent on the ventilation due to weakening of the diaphragm and the costal muscles, as well as cause barotrauma, posterior lob atelectasis, or impaired hemodynamics. Accordingly it is beneficial to wean the patient off, or to reduce the assistance level, of the ventilation machine as soon as possible. For patients requiring mechanical ventilation assistance for prolonged periods, a significant portion of that time (some studies have shown up to 40% of the time) is spent weaning the patient from the mechanical ventilation.

Two other techniques for assisting breathing that are available today include phrenic nerve stimulation and diaphragmatic pacing. Both methods use electrical stimulation to induce contraction of the diaphragm using an electrode and an external pacing control box. The two phrenic nerves, which control activation of the diaphragm, run through the thorax, along the left and right sides of the heart, and then to the diaphragm. Phrenic nerve stimulation is performed by electrically stimulating the phrenic nerve to control the patient's diaphragm, which may induce a respiratory cycle. Conventional techniques include surgically implanting a nerve cuff around the phrenic nerve (at the neck or chest level), and then delivering an electrical stimulus from an externally located controller through the cuff to the phrenic nerve. This procedure is quite invasive, requiring incisions when deploying the nerve cuffs. In addition, the direct placement of the nerve cuffs around the phrenic nerves may damage the phrenic nerve. Additionally, phrenic nerve stimulation is limited to patients having a functional phrenic nerve below the implantation level.

Another method for electrically stimulating the diaphragm is known as diaphragmatic pacing. Conventionally, diaphragmatic pacing is performed by laparoscopically implanting four electrodes directly on the diaphragm (two on each side), with electrical leads connected to a controller residing external to the body. Conventional diaphragmatic pacing procedures are also relatively invasive, requiring incisions during implantation, presenting risk during the implantation procedure and risk of chronic infection at the lead entrance site to the body.

Accordingly, there exists a need for a less invasive, safer, and simpler system and technique to provide reliable diaphragmatic pacing and phrenic nerve stimulation. It thus would be desirable to provide alternative systems, devices, and methods for positioning and fixing diaphragm stimulation electrodes proximate to desired stimulation sites, particularly for phrenic nerve stimulation and diaphragmatic pacing.

SUMMARY OF THE INVENTION

Medical devices, systems, and methods are disclosed for providing respiratory therapy by electrically stimulating the phrenic nerves and/or the thoracic diaphragm. In one aspect, at least one electrode is deployed to a position within the patient's airway and placed in proximity to a phrenic nerve or to the diaphragm. The electrode may be attached to a controller housing including a pulse generator using one or more electrical lead or leads or may be in operable wireless communication with the pulse generator. The controller housing may be implanted at a position within the patient or the controller housing may reside external to the patient.

According to another aspect, methods for electrically stimulating a diaphragm are provided. In one embodiment, the method may include positioning and fixing at least one electrode at a selected position within a patient's trachea or bronchus in operable proximity to at least one of a thoracic diaphragm or a phrenic nerve. The at least one electrode is in operable electrical communication with a pulse generator housed within a controller housing. The method may further include delivering at least one electrical stimulation signal from the at least one electrode.

According to yet another aspect, methods for operably associating a stimulation system with a patient in need thereof are provided. In one embodiment, the method may include deploying at least one electrode at a selected position within a patient's trachea or bronchus in operable proximity to at least one of a thoracic diaphragm or a phrenic nerve. The at least one electrode is in operable electrical communication with a pulse generator housed within a controller housing.

BRIEF DESCRIPTION OF THE DRAWINGS

FIGS. 24A-25B are schematic diagrams of illustrative wireless electrode and placement thereof according to some embodiments of the invention.

FIGS. 27A-27B are diagrams of illustrative stimulation patterns according to some embodiments of the invention.

DETAILED DESCRIPTION OF THE INVENTION

Figure 1A:
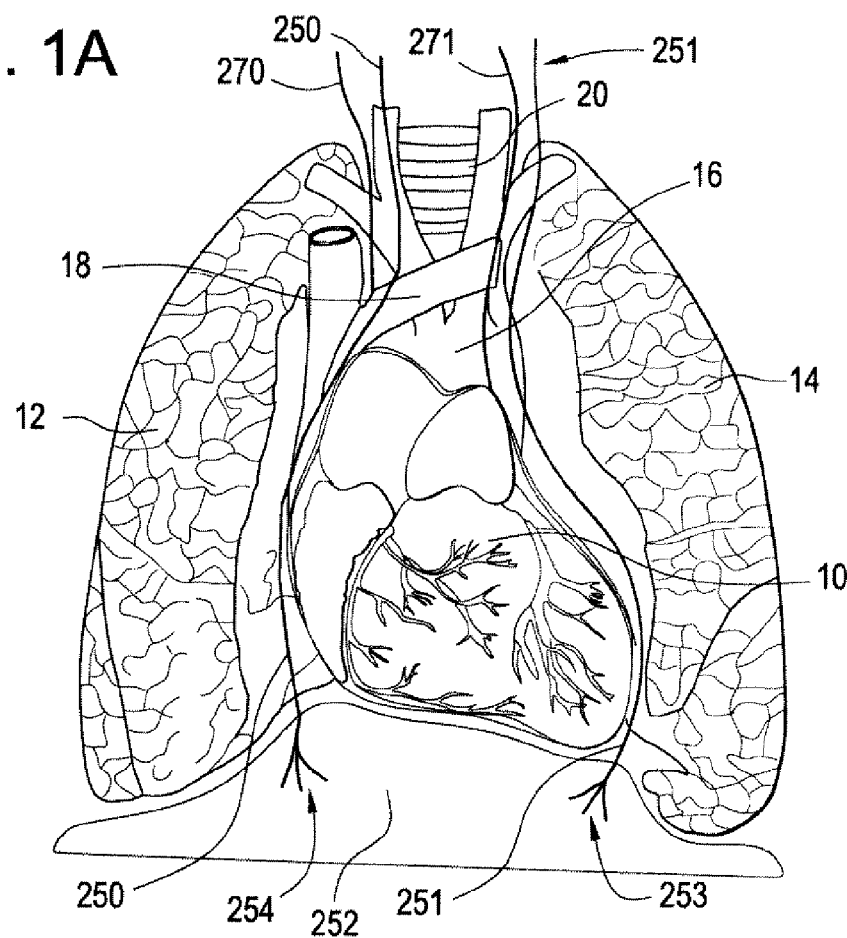
FIGS. 1A-1B illustrate a human cardiovasculature system and human respiratory system.

Medical devices, systems, and methods are provided for stimulating a patient's thoracic diaphragm or other tissues via electrodes implanted within the patient's airway. The human anatomy beneficially provides access to electrode implantation sites within the patient's airway that are in close proximity to areas of the diaphragm, or to the phrenic nerves controlling its contraction, and thus allows for alternative implantation devices and methods for electrically pacing the diaphragm and for sensing respiration activity. The stimulation electrodes beneficially can be deployed and fixed using minimally or non-invasive techniques, thus avoiding the complex, higher-risk procedures associated with traditional implantation and stimulation techniques.

In one aspect, a diaphragm pacing system is provided that includes one or more electrodes carried by one or more electrical leads, fixable within a patient's airway. The electrical leads are attachable to an implantable pulse generator for generating and delivering electrical stimulation signal to the electrodes, and optionally for receiving electrical signals from one or more electrodes representing sensed parameters. The pulse generator may be housed in a control housing, which may be implanted within the patient's airway using minimally or non-invasive techniques, for example in the patient's trachea or bronchus. In some embodiments, the pulse generator is implantable subcutaneously, for example in the patient's pectoral region. In one embodiment, the pulse generator may reside external to the patient's body and the lead may be passed through the trachea via a cannula, similar to those used to perform a tracheotomy, for example, or the lead may be passed to the airway through the mouth or nose via the pharynx without any incision, such as via an intubation tube.

In another aspect, use of an electrically conductive material in the manufacture of an electrode for a device for electrically stimulating a diaphragm is provided. The manufactured electrode is operable to electrically communication with a pulse generator and is adapted for positioning within a patient's trachea or bronchus in operable proximity to at least one of a thoracic diaphragm or a phrenic nerve. Electrical stimulation signals can be delivered from the electrode to the patient's thoracic diaphragm and/or the phrenic nerve.

The electrical stimulation signal generated by the pacing system is effective for performing direct stimulation of the diaphragm, phrenic nerve stimulation, vagus nerve stimulation, or a combination thereof. As used herein, the terms "electrical stimulation signal," "electrical signal," and "signal" are used interchangeably and may generally refer to any transmittable electrical current, and are not limited to a transmission containing information or data. Also, as used herein, the terms "electrical pulse" or "pulse" are used interchangeably and may generally refer to one or more intermittent transmissions of an electrical current, such as is used during phrenic nerve stimulation or diaphragmatic pacing. Also, as used herein, the terms "diaphragm," "thoracic diaphragm," or "peritoneal diaphragm" are used interchangeably and generally refer to the diaphragm separating the thoracic cavity from the abdominal cavity, which may serve a substantial role in respiration. Also, as used herein, the terms "diaphragm pacing" and "diaphragmatic pacing" may be used interchangeably to generally refer to electrically stimulating a phrenic nerve, directly stimulating a diaphragm, or any combination thereof.

Because the diaphragm is skeletal muscle, diaphragmatic pacing may be accomplished by delivering a series of multiple stimulation signals to produce a mechanically effective contraction of the diaphragm. Multiple stimulation signals are also referred to as a pulse train or a pulse train signal or signals. A pulse train is typically characterized by the rate, the duration, the pulse width, the frequency, and the amplitude of the signals. The rate of the pulse train corresponds to the number of pulse trains delivered per minute, which in turn correlates with the patient's respiratory rate. The duration of the pulse train refers to the length of time the pulse train is delivered. The pulse width indicates the duration of each individual pulse creating the pulse train. Similarly, the frequency indicates the number of individual pulses delivered per second. Finally, the amplitude refers to the voltage of each pulse delivered. The parameters of amplitude, frequency, and pulse width determine the strength of the induced diaphragmatic pacing. Parameters of example pulse train signals that can be administered according to the various methods and systems described herein are provided in more detail with reference to the description of the pulse generator, and with reference to FIG. 4.

In some embodiments, incomplete or selective nerve stimulation is delivered, which is effective to allow some diaphragm muscle bundles to contract while others rest, which more closely resembles natural respiratory patterns. In other embodiments, other pulse train patterns and/or pacing techniques may be administered, such as, but not limited to, unilateral stimulation, which may be performed at higher frequencies, or low-frequency, continuous bilateral pacing. As discussed further herein, pacing can be delivered for various durations, such as for periods of minutes or hours, which is useful when conditioning patients for diaphragmatic stimulation therapies, or delivering period therapy. Over time, diaphragmatic stimulation therapy may be delivered using reduced frequencies to minimize the diaphragmatic pacing fatigue that patients may suffer.

The diaphragm pacing system described herein may be adapted to be operable to sense diaphragm and/or cardiac electrical activity, respiratory activity, other cardiac activity, or other physiological parameters, and to generate and deliver electrical stimulation pulses in response thereto. In yet another embodiment, the electrodes positioned within the patient's airway for stimulating the diaphragm, or additional electrodes positioned in the airway, are used to stimulate and/or sense the patient's heart, as described in U.S. application Ser. No. 12/128,489 entitled "Implantable Devices and Methods for Stimulation of Cardiac and Other Tissues," filed on May 28, 2008, and U.S. application Ser. No. 12/136,812 entitled "Implantable Devices and Methods for Stimulation of Cardiac and Other Tissues," filed on Jun. 11, 2008, both of which are incorporated herein by reference in their entirety.

Accordingly, the devices and methods described herein may be employed to treat or mitigate various respiratory disorders such as central sleep apnea, Cheyne-Stokes respiration disorder, chronic intractable hiccups, muscular dystrophies, motor neuron disease including ALS, damage to the brain's respiratory centers, polio, myasthenia gravis, myopathies affecting the diaphragm or the chest muscles, and various respiratory problems that results from spine injury or other types of paralysis that may impair a patient's ability to breath. The devices and methods described herein may further be employed to support surgical anesthesia procedures and cardiac procedures. The devices and methods described herein may also be used to provide ventilation assistance therapy by delivering diaphragm stimulation signals alone, or in combination with other ventilation assistance therapies, such as mechanical ventilation. In a similar manner, diaphragm stimulation can also facilitate regenerating and/or reconditioning a patient's diaphragm and/or costal muscles during or after the administration of ventilation assistance therapy.

In another aspect, implantable system and devices are provided for stimulation of essentially any tissue structure accessible via a patient's airway. That is, the airway may be used to position one or more electrodes for stimulating tissue structures other than the diaphragm. For example, the vagus left and/or right nerves at their thoracic section may be stimulated to control gastric activity, treat digestive disorders (blocking the vagus nerve signal by electrical stimulation was demonstrated to help obese patients to lose weight), treat clinical depression, treat and prevent epileptic seizures, and/or to control heart rate.

As used herein, the terms "comprise," "comprising," "include," and "including" are intended to be open, non-limiting terms, unless the contrary is expressly indicated.

Like numbers refer to like elements throughout the following description.

I. Description of Anatomy

FIG. 1A illustrates an anatomical view of a human pulmonary system, nervous system and cardiovascular system, representing the relative position of the heart 10, the right lung 12 and left lung 14, the aorta 16, the pulmonary artery 18, the trachea 20, the left phrenic nerve 251, the right phrenic nerve 250, the left vagus nerve 271, the right vagus nerve 270, and the diaphragm 252. The right phrenic 250 passes posterior to the subclavian vein over the right atrium crosses the root of the right lung and to the diaphragm 252, where several right phrenic nerve branches 254 are formed. The left phrenic nerve 251 passes adjacent the left side of the heart, over the left ventricle, and to the diaphragm 252, where several left phrenic nerve branches 253 are formed.

The right vagus nerve 270 ascends into the neck between the trachea and esophagus. The right vagus passes anterior to the right subclavian artery, runs posterior to the superior vena cava, and descends posterior to the right main bronchus, forming the posterior vagal trunk at lower part of esophagus and entering the diaphragm through esophageal hiatus. The left vagus nerve 271 descends over the aortic arch and ascends between the trachea and the esophagus. The left vagus forms the thoracic cardiac branches, splits into pulmonary plexus, and continues via the diaphragm 252 where it enters the abdomen.

The diaphragm 252 is a dome-shaped, musculofibrous septum, with a convex upper surface, which separates the thoracic cavity from the abdominal cavity. The left and right diaphragm muscles are innervated by the left and right phrenic nerve branches 253, 254, respectively. The branches innervate the respective diaphragm muscles in a substantially even distribution. Accordingly, stimulating a portion of a phrenic nerve will result in a substantially even contraction of the respective muscle innervated by the phrenic nerve.

Figure 1B:
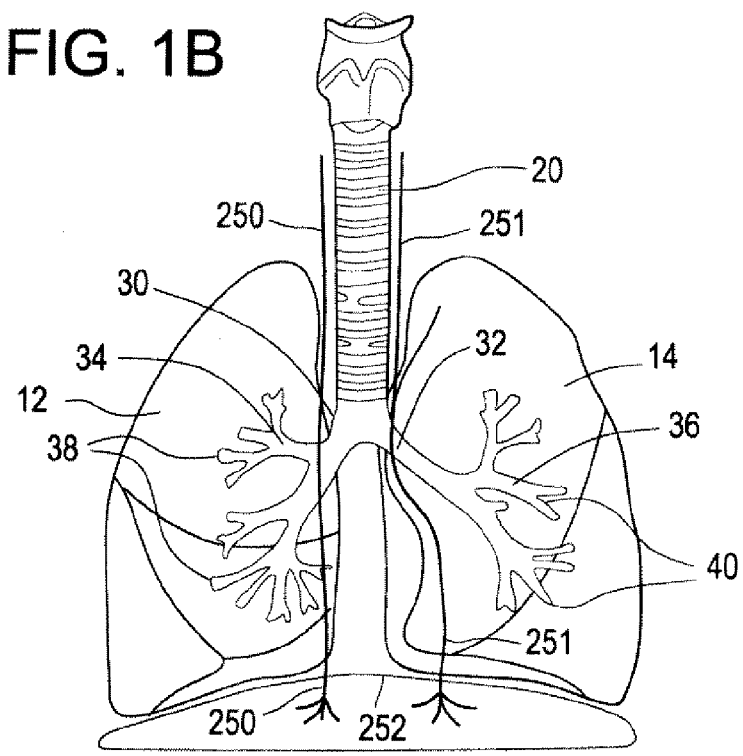

The human pulmonary system includes the trachea and bronchial tree, which includes the bronchi and bronchioles. Each time one of these airways branches (e.g., splits into two or three), it forms a new generation of airway. FIG. 1B illustrates an anatomical view of a pulmonary system that includes the trachea 20 (0 generation airway), and the right lung 12 and the left lung 14. The trachea 20 branches into the right primary bronchus 30 and left primary bronchus 32 (first generation airways), which in turn branch into the lobar bronchi (second generation airways). The lobar bronchi include three right secondary bronchi 34 and two left secondary bronchi 36. The secondary bronchi 34, 36 branch into the segmental bronchi that serve bronchopulmonary segments (third generation airways), which includes, as shown in the Figure, the right tertiary bronchi 38 and left tertiary bronchi 40. Although not shown in FIG. 1B, the tertiary bronchi 38, 40 branch into primary bronchioles (fourth generation airways) and ultimately into terminal bronchioles which are associated with alveoli for facilitating gas exchange in the lungs. The diameter of the bronchi is typically approximately 7 to 11 mm at the primary bronchi, and progressively decreases down the segmental bronchi to a diameter of less than about 1 millimeter at the bronchioles. The terms "bronchus," "bronchi," and "bronchial tree" as used herein may refer to any of the individual components of the bronchi, including the primary bronchi 30, 32, the secondary bronchi 34, 36, the tertiary bronchi 38, 40, and/or the bronchioles branching therefrom. The term "airway" as used herein may refer to the bronchi and/or the trachea 20. FIG. 1B demonstrates that the bronchi reach a substantial portion of the left and right lungs 14, 12, enabling access through at least one branch to be in proximity to various areas of the heart 10.

Since the phrenic nerves and the vagus nerves run in close proximity to the lungs with just the very thin lung pleura separating them in some areas, an electrode positioned in the bronchi may operate to achieve results similar to cuff electrodes around the phrenic or vagus nerves. Moreover, since the lungs are proximate to and in contacting relationship to the diaphragm, an electrode positioned in the periphery of the bronchi may be used to stimulate the diaphragm in a similar fashion to an electrode surgically implanted on the diaphragm through an invasive procedure. Accordingly, positioning an electrode in a patient's airway in operable proximity to the phrenic nerves or to the diaphragm provides a minimally or non-invasive technique for performing diaphragmatic stimulation and/or for sensing, which avoids the complexity and inherent risks of traditional techniques requiring complex, invasive procedures for implantation. As used herein, the term "operable proximity" may be used to generally refer to a distance between an electrode implantation site and the target nerve or diaphragm (or other organ or tissue) that is close enough to effectively deliver the desired stimulation and/or to sense the desired property at or about the respective nerve or diaphragm. In one embodiment, a distance ranging between approximately 0.05 mm to approximately 15 mm may be in "operable proximity" for stimulating a phrenic nerve or diaphragm. In another embodiment, a distance ranging between 0.05 mm and 5 mm may be in "operable proximity." However, any distance suitable for delivering the intended stimulation signal may be considered within "operable proximity."

According to another embodiment, one or more electrodes carried by electrical leads may be implanted in a patient's upper gastrointestinal tract in operable proximity to the diaphragm and/or a phrenic nerve for performing diaphragmatic stimulation. The human anatomy can provide access to electrode implantation sites within the patient's upper gastrointestinal tract, such as the esophagus and the stomach, that are in close enough proximity to the diaphragm or phrenic nerves to provide stimulation thereof, allowing for alternative implantation devices and methods for diaphragmatic stimulation, and/or for stimulating other tissues. Although the examples described herein may be generally directed to embodiments in which one or more electrodes and/or controllers are implantable within a patient's airway, the system may be adapted for implantation within the stomach or the esophagus. The system may be configured and operate in manners similar to that described in U.S. application Ser. No. 12/136,812 and incorporated herein by reference, but adapted for positioning near and simulating the thoracic diaphragm and/or phrenic nerve(s).

Representative embodiments and configurations of diaphragmatic stimulation systems and methods are provided in more detail herein.

Figure 2:
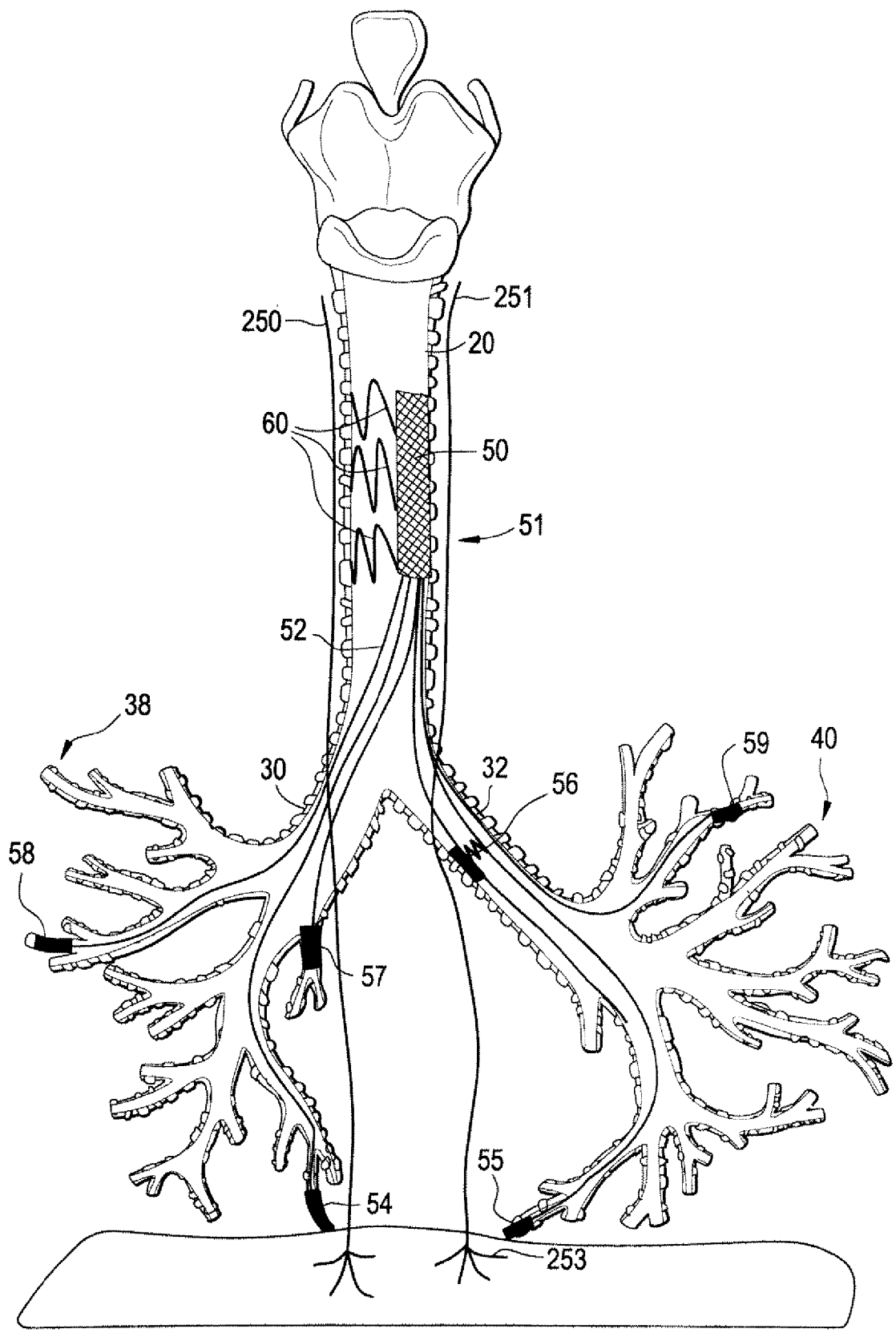
FIG. 2 is a diagram of an illustrative diaphragm pacing device placement according to one embodiment of the invention.

II. Implantable Electrodes and Electrical Leads Attachable to a Pulse Generator Implantable in an Airway FIG. 2 illustrates one embodiment of an implantable diaphragmatic stimulation system. A controller housing 50 including a pulse generator 51 is adaptable for implantation at a selected housing position within the trachea 20, the bronchus, such as the right or left primary bronchus 30, 32, or a branch thereof. In some embodiments, the controller housing 50 is retained by one or more anchor devices 60, as is more fully described herein.

It is appreciated that as used herein the terms "controller housing" and "control box" may be used interchangeably to generally refer to the structure or casing that houses the pulse generator and any other electronic circuitry, hardware, software, and for performing electrical stimulation and sensing as described herein. As used herein, the terms "pulse generator" and "controller" may be used interchangeably to generally refer to any device operable of generating electrical stimulation signals, such as an electrical current; though, in some embodiments, a "pulse generator" or "controller" may also be operable for receiving electrical signals representing sensed or measured parameters from one or more sensing electrodes or other sensors; and in other embodiments, a "pulse generator" or "controller" may be operable to wirelessly cause delivery of an electrical stimulation signal via wireless control commands to one or more wireless electrodes that generate an electrical stimulation signal. Accordingly, a "pulse generator" or "controller" as referred to herein may generate, or wirelessly cause the delivery or generation of, electrical signals or electrical pulses, such as when performing diaphragmatic pacing, receive electrical signals, such as when performing sensing functions, or both. Furthermore, when referencing the "controller housing," it is appreciated that the "pulse generator" is included therein.

The pulse generator 51 may be electrically coupled to at least one electrical lead 52. At least one electrode is affixed to, integrated within, or carried by an electrical lead 52. As used herein, the term "carried" when referring to an electrical lead carrying an electrode includes electrodes, temporarily or permanently affixed to the electrical lead, electrodes integrated within the electrical lead such that they are a single component, or otherwise. In another embodiment, the pulse generator communicates wirelessly with one or more electrodes or other sensors, and thus an electrical lead is not required. In the embodiment illustrated in FIG. 2, six electrodes 54, 55, 56, 57, 58, 59, each carried by an individual electrical lead 52 are attachable to the pulse generator 51. The electrodes are positioned at or near the distal end of the electrical lead 52, as illustrated in FIG. 2. However, in other embodiments, an electrode may be positioned proximal to the distal end of the electrical lead 52, for example, in embodiments including a single electrical lead 52 that carries more than one electrode, such as one at or near the distal portion of the lead and one or more electrodes on the same electrical lead 52 proximal to the distal electrode.

The implantable diaphragmatic stimulation system may include one or more electrodes, depending on the type of stimulation or sensing to be performed. The electrodes can be positioned and fixed at different areas within the airway to electrically stimulate various nerves and tissues, including, but not limited to, the left phrenic nerve, right phrenic nerve, the diaphragm (the left and/or right hemispheres), or any combination thereof. In one embodiment, the electrodes are operable to stimulate, in combination with the diaphragmatic stimulation or alone, the left vagus nerve, the right vagus nerve, the sympathetic trunk, the recurrent laryngeal nerve, the sinoatrial node, the vagus nerve, the right atrium, the right ventricle, the left atrium, the left ventricle, or any combination thereof. Employing multiple electrodes in combination may optimize the path of electrical current, thus improving treatment and minimizing current or voltage requirements to achieve the intended therapy.

The embodiment in FIG. 2 illustrates six electrodes positionable and fixable at six selected positions within the bronchi, each connected to a different electrical lead 52. As illustrated, three electrodes 54, 57, 58 are positioned and fixed within the right tertiary bronchi 38, two electrodes 55, 59 are positioned and fixed within left tertiary bronchi 40, and one electrode 56 is positioned and fixed within the left primary bronchi 32. In this embodiment, each electrode 54, 55, 56, 57, 58, 59 is carried by a separate electrical lead 52 that is electrically coupled to the pulse generator 51.

In other embodiments, however, a single lead 52 is coupled to the pulse generator 51 and splits into multiple leads 52 each carrying a single electrode to its implantation site. In yet other embodiments, a single lead 52 is coupled to the pulse generator 51 and carries multiple electrodes to approximately the same implantation site, for example, when delivering stimulation signals to a phrenic nerve at or around the same position through multiple electrodes, so as to provide greater and/or varied stimulation to the nerve at a single implantation site, or when delivering stimulation to the thoracic diaphragm by multiple electrodes to increase the amount of the tissue being stimulated.

The embodiment illustrated in FIG. 2 is provided for illustrative purposes, showing possible electrode positioning that may be used to provide the various therapies described herein; however, other electrode and pulse generator positioning and configurations are possible, as further described herein.

For example, according to another embodiment, one or more electrodes carried by one or more electrical leads are adaptable for deployment to a position within the airway and for penetration through the airway for directly coupling with a phrenic nerve or the diaphragm. The electrode may be deployed by any suitable delivery means known in the art, such as using a delivery device like an endoscope or a catheter, which may optionally have a substantially sharp and/or rigid tip at its distal end. The electrode may be similar to conventional phrenic nerve or diaphragm stimulation electrodes and may be affixed to thereto in any conventional manner. In another embodiment, the electrode may be configured as a needle electrode, which may puncture and penetrate the wall of the airway and directly couple to the phrenic nerve or the diaphragm. In one example, fluoroscopy or other imaging techniques may be used to deploy the electrode and/or delivery device. Penetrating the airway can overcome the potential difficulties of navigating through the complex bronchial tree to position one or more electrodes in operable proximity to the desired implantation site, allowing the airway to provide access to an approximate penetration site and then navigating directly to the nerve or diaphragm.

Housing

The controller housing 50 is implantable within a patient's trachea 20, as illustrated in FIG. 2, within the right or left primary bronchus 30, 32, or a branch thereof. In one embodiment, the controller housing 50 is dimensioned to be implanted further down the airway, such as within the secondary or tertiary bronchi. As described above, the pulse generator 51 may be operable to generate and deliver electrical stimulation signals to the one or more electrodes 54, 55, 56, 57, 58, 59 via the electrical leads 52 effective in performing diaphragmatic pacing, vagus nerve stimulation, blocking for gastric control, treating and/or preventing epileptic seizures, controlling heart rhythms, controlling blood pressure, treating depression, or any combination thereof.

In one embodiment, the pulse generator 51 is operable to measure physiological conditions via one or more of the electrodes 54, 55, 56, 57, 58, 59, such as measuring electrical respiration and/or cardiac activities, like electrical impedance across two points or diaphragm depolarization. In another embodiment, the pulse generator 51 is operable to control and receive measurements representing other physiological parameters from additional sensors, such as an accelerometer, a position sensor, a strain gauge, a pressure transducer, or a temperature sensor, implanted within the patient's body that may measure parameters related to respiration and its quality, or other physiological conditions. Although various embodiments described herein include a single controller housing and pulse generator performing all of the diaphragmatic stimulation and sensing functions, other embodiments may include more than one controller housing and pulse generator, with each pulse generator performing separate functions and/or providing redundant functioning for reliability and safety purposes.

A controller housing 50 implantable in an airway is proportioned to substantially permit airflow through the respective airway past the controller housing and to avoid substantial discomfort to the patient. A trachea may have an inner diameter of approximately 15 mm to 25 mm and a length of approximately 10 cm to 16 cm; thus, the controller housing 50 may be proportioned to be smaller in diameter than approximately 15 mm to 25 mm and have a length less than approximately 10 cm to 16 cm. For example, in one embodiment, the controller housing 50 is an elongated cylinder with a diameter of approximately 4 mm to 10 mm, and a length of approximately 4 cm to 11 cm. In another embodiment, the controller housing 50 has a diameter less than approximately 7 mm and a length of less than approximately 6 cm. In certain embodiments, the cross section of the controller housing 50 may be substantially curvilinear, such as circular or elliptical; though in other embodiments, the cross section may be substantially square, rectangular, triangular, or have any other cross-sectional geometry. The controller housing 50 may further be proportioned such that at least part of the controller housing 50 will substantially contact the inner wall of the airway at the selected implantation site. In embodiments in which the controller housing 50 has a curvilinear cross section, the radius of curvature may approximate that of the inner wall of the trachea 20 or bronchus.

In addition, any of the illustrative controller housing embodiments described herein may optionally include radiopaque material to aid in deployment procedures using imaging techniques, biocompatible coating, medicinal or therapeutic coating, such as anti-proliferative agents, steroids, antibiotic agents, or any combination thereof.

Anchor Devices

FIGS. 3A-3E illustrate several illustrative devices for anchoring the controller housing containing the pulse generator within the trachea or bronchus, according to certain embodiments. The embodiments described herein are representative; however, other means for positioning and anchoring the controller housing within an airway may be employed. Although at least some of the embodiments of the anchor device may be described as being implantable within the trachea, the anchor device designs equally apply to controller housing implantable within the bronchus.

Figure 3A:
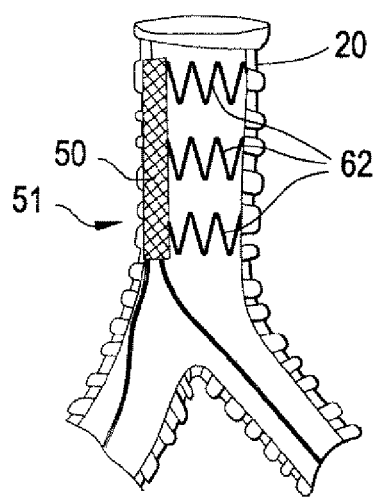
FIGS. 3A-3F are diagrams of illustrative devices for anchoring a controller housing according to some embodiments of the invention.

FIG. 3A illustrates an extensible member, such as a radially expandable member 62 for anchoring the controller housing containing the pulse generator 51 to the inner wall of the trachea 20, for example to the epithelial tissue. The expandable member 62 is configured in a substantially tubular shape similar to a stent, such that it includes at least one circumferential ring extending from the controller housing 50 and proportioned to interface with the inner wall of the trachea 20. For example, a stent-like expandable member 62 may have a interwoven, zigzag, wave-like, mesh, z-shaped, helical, or otherwise radially expandable and contractible or collapsible shape as is known, and extends from one side of the controller housing 50. In its expanded or extended position, the expandable member 62 has a radius of curvature substantially similar to the inner wall of the trachea 20 to promote retention of the controller housing 50. Furthermore, an expandable member 62 configured similar to a stent, having a hollow lumen or path existing along its axis, is advantageously proportioned to permit airflow through the trachea 20 and around the controller housing 50 at the selected housing implantation site or position. The expandable member 62 may be formed from metals, such as nickel-titanium alloys, stainless steels, tantalum, titanium, gold, cobalt chromium alloys, cobalt chromium nickel alloys (e.g., Nitinol™, Elgiloy™) or from polymers, such as silicone, polyurethane, polyester, or any combination thereof. In other embodiments, the anchor device may be formed as a substantially solid tubular member, and may include a separate expansion means for extending from the controller housing 50 and exerting force against the tubular member, causing the tubular member to substantially engage the inner wall of the trachea 20. Each embodiment of the expandable member 62 as described provides sufficient force against the trachea 20 for retaining the controller housing 50 in place, but should not apply too much force to avoid damaging the trachea 20 or causing discomfort to the patient. Expansion of these expandable member 62 embodiments may be performed mechanically, such as by stent-like designs, springs, balloons, and the like, or expansion may be caused by the material characteristics of the members, such as shape memory alloys, or any combination thereof. Optionally, any of the described expandable members 62 may additionally include one or more barbs, hooks, suture, and the like for securing the member 62 to the inner wall of the trachea 20.

Figure 3B:
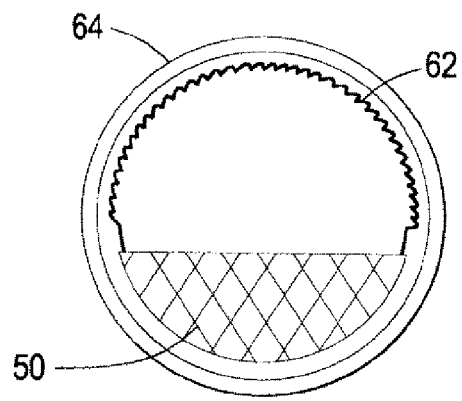

During implantation of the controller housing 50, the stent-like expandable member 62 can be contracted or collapsed against, or within close proximity to, the controller housing 50 to minimize the profile during deployment, for example when deployed using a delivery device 64, such as a catheter or other elongated cannula for delivery, as is illustrated in FIG. 3B. Upon positioning the controller housing 50 at the implantation site and releasing it from the delivery device 64, the expandable member 62 expands and substantially engages the inner wall of the trachea. The controller housing 50 may optionally include a recess or have a substantially flat surface on the side from which the expandable member 62 extends, such that the recess or flat surface receives at least part of the expandable member 62 when in compressed form, further reducing the profile to aid in deployment by a delivery device.

Figure 3C:
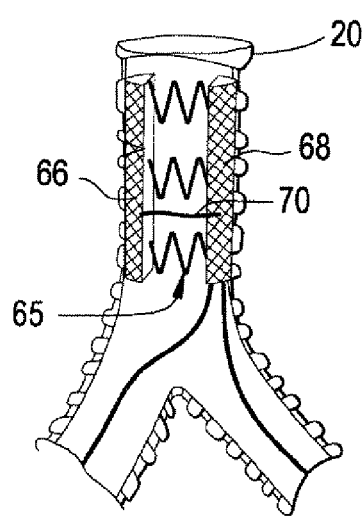

FIG. 3C illustrates another embodiment of an extensible member including one or more expandable connectors 65 connecting at least two separated controller housing sub-components 66, 68. In this embodiment, the one or more expandable connectors 65 create opposing forces against the two separated controller housing sub-components 66, 68, biasing each against the inner wall of the trachea 20 at opposing areas, and thus anchoring the controller housing sub-components 66, 68 in place. The expandable connectors 65 may be configured similar to the expandable member 62 described with reference to FIGS. 3A-3B. In some embodiments, the expandable connectors 65 may be formed as a metallic or polymeric spring, from a shape memory alloy, as mechanically adjustable rigid members, or as telescoping members. In one embodiment, the two separate sub-components 66, 68 are electrically coupled by one or more isolated electrical leads 70 to facilitate power transfer and/or electrical communication between the pulse generator circuitry existing within the controller housing sub-components 66, 68 and/or with one or more electrical leads carrying electrodes. Although the embodiment illustrated by FIG. 3C includes only two separated controller housing sub-components 66, 68, the controller housing may be formed as any number of controller housing sub-components, each radially biased toward the inner wall of the trachea 20.

Figure 3D:
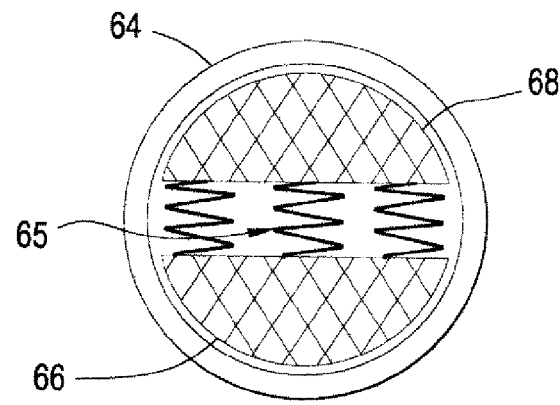

Similar to the embodiment illustrated in FIGS. 3A and 3B, the two or more separated controller housing sub-components 66, 68 connected by one or more expandable connectors 65 may be compressed to a reduced profile during placement, for example, when deploying using a delivery device 64, as illustrated in FIG. 3D. In this embodiment, two separated controller housing sub-components 66, 68 each have a substantially semi-circular cross section and are complementary in shape to each other.

Figure 3E:
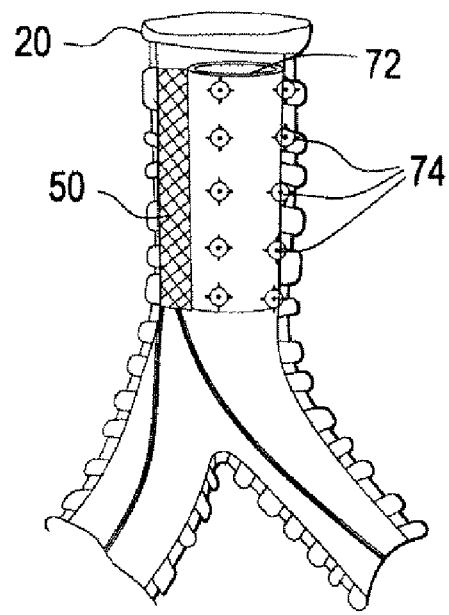

FIG. 3E illustrates another embodiment of an extensible member attached to the controller housing 50, configured as a tubular expandable member 72. The tubular expandable member 72 is substantially tubular in shape, similar to that as described with reference to FIGS. 3A and 3B, and may have solid or substantially solid tubular walls. The tubular expandable member 72 illustrated in FIG. 3E further includes one or more studs, barbs, hooks 74, or any combination thereof, to assist retaining the member 72 against the inner wall of the trachea 20 at the selected housing implantation position. In certain embodiments, the tubular expandable member 72 may be formed from a polymer, such as silicone or polyurethane; though, in other embodiments, the tubular expandable member 72 may be formed from a metallic material in a mesh or woven configuration.

Figure 3F:
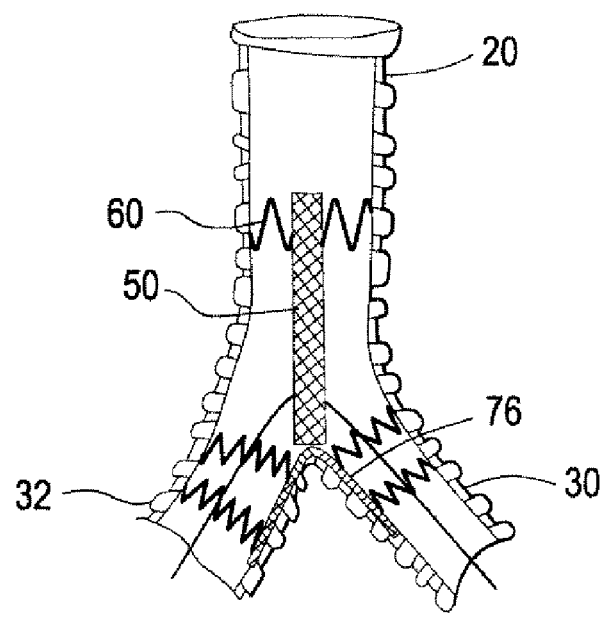

FIG. 3F illustrates an embodiment of an anchor device which may be employed to prevent distal migration of the controller housing 50. According to this embodiment, the bifurcation between the trachea 20 and the right and left primary bronchus 30, 32 support the controller housing 50. An arched member 76 is attached to the distal end of the controller housing 50, includes an arm extending into each primary bronchus 30, 32, and is substantially supported by the bifurcation. The arched member 76 may be secured using an extensible member, such as any anchor device described with reference to FIGS. 3A-3E, or by any other anchoring means, such as a balloon, suture, staples, barbs, hooks, studs, adhesive, shape memory alloy members, or any combination thereof. In one embodiment, the arched member 76 may be shaped before or during implantation to more specifically follow the curvature of the bifurcation, further facilitating retention of the controller housing 50 within the airway. In this embodiment, an additional anchor device 60 is affixed to the controller housing 50, such as those described herein. In other embodiments, anchor members may not be included with either the controller housing, the arched member, or both.

Other embodiments of the anchor device for retaining the controller housing 50 at a desired position within the trachea, though not illustrated, may be employed. For example, the controller housing may be held against the trachea by suture, adhesive, or a combination thereof, as is known. In another embodiment, the anchor device may be a reversibly inflatable balloon, formed as a sleeve, having an opening passing axially therethrough, and expanding radially. In this example, the balloon may be deflated during placement and then inflated to expand radially by methods known, causing a biasing force against the trachea. Further, the external surface of the balloon sleeve may be include texturing, texturing, suture, barbs, hooks, studs, adhesive, or any combination thereof, to further facilitate retaining the sleeve against the trachea wall. In yet another embodiment, the anchor device may be formed as one or more radially extending rigid members, which may be extensible, collapsible, telescoping, inflatable, formed from shape memory alloy, and the like, causing a radially biasing force against the inner wall of the trachea.

In addition, any of the anchor devices described herein optionally may include a radiopaque material to aid in deployment procedures. The radiopaque material may be used in part or all of device. The radiopaque material may be useful to facilitate device or component placement using known imaging techniques. The anchor devices described herein optionally may include a biocompatible coating. The coating may include one or more prophylactic or therapeutic agents, such as anti-proliferative agents, steroids, antibiotic agents, or any combination thereof.

Pulse Generator

Figure 4:
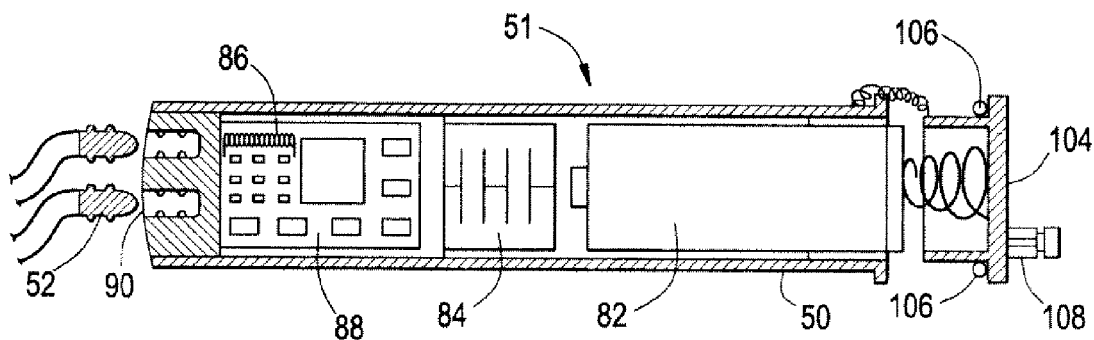
FIG. 4 is a schematic diagram of an illustrative controller housing including a pulse generator according to one embodiment of the invention.

FIG. 4 illustrates an embodiment of a pulse generator 51 and many of the features that may be included as components of the pulse generator 51. Example features which may be included in a typical pulse generator 51 include a power source 82, a capacitor circuit 84, which may be used to charge and discharge during stimulation, an electronic controller 88, which may be implemented by a microprocessor, an integrated circuit, a field programmable gate array ("FPGA"), or other electronic circuitry as is known, a communication module 86, one or more electrical lead sockets 90, and a controller housing 50 encapsulating components contained within the pulse generator 51 and forming the external structure thereof. As described herein, the pulse generator 51 and its associated elements are operable to generate and deliver an electrical stimulation signal or pulse effective for performing phrenic nerve stimulation, diaphragmatic pacing, vagus nerve stimulation, or any combination thereof. In another embodiment, the pulse generator 51 may be operable to generate and deliver stimulation signals or pulses effective for providing cardiac pacing, cardiac defibrillation, cardioversion, and/or cardiac resynchronization therapy via one or more electrodes suitably positioned. The pulse generator 51 may optionally include electronic circuitry, hardware, and software to measure and sense phrenic nerve electrical activity, diaphragm electrical activity, other diaphragmatic activity, diaphragm mechanical activity, other physiological parameters, or any combination thereof. The pulse generator 51 may also be operable for wirelessly causing one or more electrical signals to be generated and delivered by one or more wireless electrodes via wireless control commands, such that the generation of electrical signals occurs within the circuitry of the one or more wireless electrodes, as described in more detail with reference to FIGS. 25A-25B. Accordingly, the power source 82 in combination with the electronic controller 88 may include hardware and/or software suitable for delivering electrical stimulation signals, and optionally for receiving electrical sensing signals, via one or more electrical leads 52 electrically coupled to the lead sockets 90 and carrying one or more electrodes, as is described more fully herein.

In illustrative embodiments, the pulse generator is operable to deliver pulse or pulse train stimulation signals, such as when performing diaphragmatic stimulation. The stimulation signal patterns and characteristics may vary based upon the intended use, such as if being delivered to a phrenic nerve or to a diaphragm directly, or if being delivered for respiratory therapy or for digestive therapy. According to one embodiment, a pulse stimulation signal (also referred to herein as "pulse pattern" or "signal pattern") may have an amplitude ranging from approximately 0.2 volts to approximately 12 volts (or an equivalent current based on the impedance of the system) and a pulse duration ranging from approximately 0.3 milliseconds to approximately 12 milliseconds. According to another embodiment, a pulse train signal pattern may have an amplitude ranging from approximately 0.5 volts to approximately 12 volts (or an equivalent current based on the impedance of the system), or in one embodiment ranging from approximately 2 volts to approximately 5 volts, and an "on" time (similar to width) ranging from approximately 0.1 seconds to approximately 5 seconds. The amplitude of the pulse train output may be adjusted to obtain sufficient tidal volume and to maintain $PaCO_2$ (the carbon dioxide pressure in arterial blood) within an acceptable range, which may be approximately 40 mmHg in one example. A pulse train signal pattern may have a pulse width ranging from approximately 80 microseconds to approximately 300 microseconds, or in one embodiment, approximately 150 microseconds, and an excitation frequency ranging from approximately 10 Hertz to approximately 50 Hertz, or in one embodiment approximately 20 Hertz. The signal patterns delivered when performing diaphragmatic pacing to deliver respiratory therapy may be delivered to facilitate breathing rates ranging from approximately 10 breaths per minute to approximately 50 breaths per minute. Moreover, the stimulation signal patterns may be delivered at varying frequencies, pulse widths, pulse trains, and/or voltage outputs, or may be dependent upon other ventilation therapies and/or a patient's breathing pattern, such as is described with reference to FIGS. 27A-27B, to optimize diaphragmatic pacing and/or other therapies provided by the systems and methods described herein.

Because the pulse generator 51 is implantable within a trachea or bronchus, or in some embodiments subcutaneously, the controller housing 50 may be constructed so as to withstand humidity, gasses, and biological fluids. In one embodiment, the controller housing 50 is hermetically sealed and constructed to withstand the environment of the airway and protect the circuitry, power source, and other elements contained therein. A controller housing 50 implantable in either the trachea or the bronchus generally will not be continually immersed in a liquid environment, which enables the use of polymeric materials for construction. In contrast, a subcutaneous implant may be constructed from metallic materials. Accordingly, in embodiments implanted in the airway, the controller housing 50 may be entirely or partially constructed from polymeric material, such as but not limited to, epoxy, polypropylene, polyethylene, polyamide, polyamide, polyxylene, polyvinyl chloride ("PVC"), polyurethane, polyetheretherketone ("PEEK"), polyethylene terephthalate ("PET"), liquid crystal polymer ("LCP"), and the like. In other embodiments, however, the controller housing 50 may be constructed from entirely or partially metallic materials, such as, but not limited to, nickel, titanium, stainless steel, tantalum, titanium, gold, cobalt chromium alloy, or any combination thereof, and may be constructed using laser or electron beam welded seams. In yet other embodiments, the controller housing 50 may be constructed from any combination of one or more of these polymeric or metallic materials, or other materials known in the art to be suitable for fabricating or encasing implantable medical devices.

All or partial polymeric construction of the controller housing 50 may be advantageous as compared to completely metallic construction, avoiding the Faraday cage effect that may be caused by a complete metallic casing. A Faraday cage effect may limit the use of electromagnetic fields to communicate or otherwise interface with the pulse generator 51. Accordingly, a non-conductive controller housing 50, such as one constructed from polymeric materials as described herein, allows electromagnetic fields for communicating with, controlling, and otherwise interfacing with the pulse generator 51. For example, electromagnetic fields may be used for recharging battery power sources associated with the pulse generator 51, without removing the pulse generator 51 and/or the battery power source. In another embodiment, the controller housing 50 may be constructed partially from metallic materials, for example at the points interfacing with the trachea and/or bronchus, and partially from polymeric materials. A controller housing 50 constructed in such a manner also avoids the Faraday cage effect by not being completely surrounded by an electrical conducting metal.

Some or all of the external components of the pulse generator 51, including the controller housing 50 and the anchor device described with reference to FIGS. 3A-3F, may be entirely or partially coated to aid or improve hermeticity, electrical conductivity, electrical isolation, thermal insulation, biocompatibility, healing, or any combination thereof. Representative coatings include metals, polymers, ultra-nanocrystalline diamond, ceramic films (e.g., alumina or zirconia), medicinal agents, or combinations thereof. For example, in one embodiment, the controller housing 50 is coated by a polyxylene polymer to further electrically isolate the electrical circuitry, power source, and other elements from the patient's body. In another example, the controller housing 50 and/or the anchor device, particularly at the points interfacing with the trachea or bronchus, is at least partially coated with a biocompatible coating, medicinal or therapeutic coating, such as anti-proliferative agents, steroids, antibiotic agents, or any combination thereof, to promote healing of trauma caused during implantation and/or to avoid infection.

Figure 5:
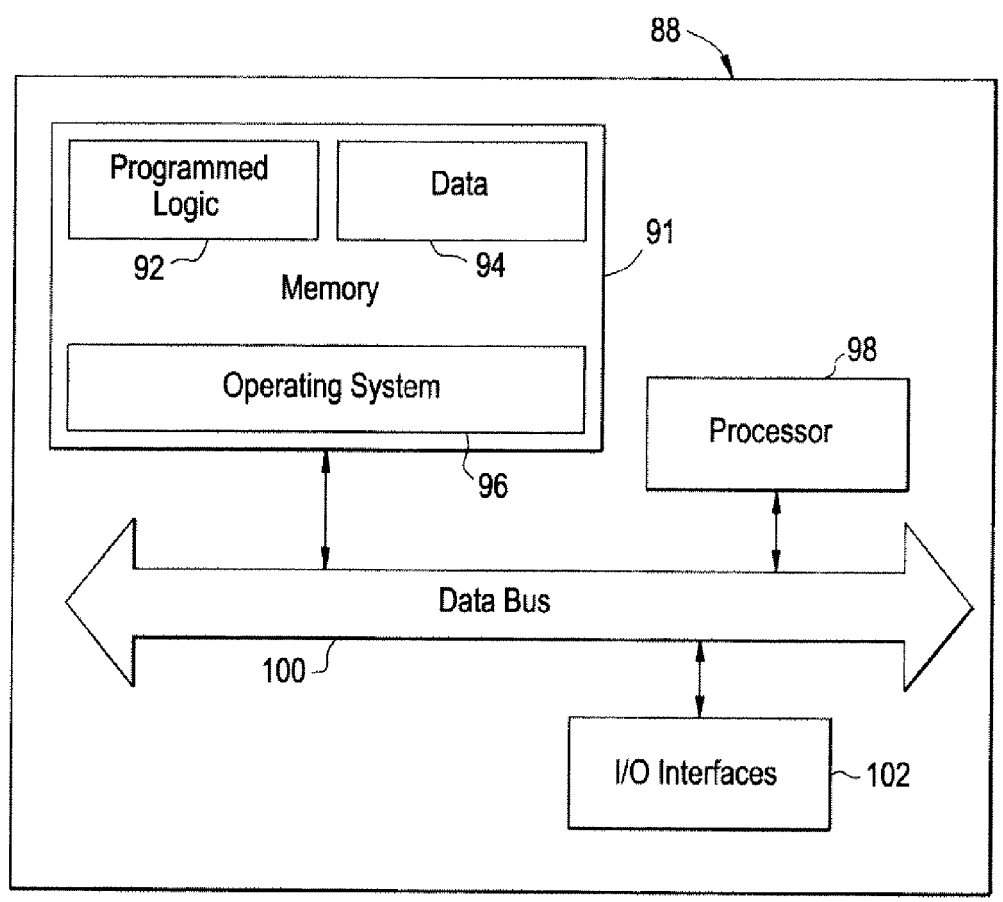
FIG. 5 is a functional diagram of an illustrative electronic controller according to one embodiment of the invention.

FIG. 5 depicts a schematic diagram of one example of an electronic controller 88 that may be utilized to generate, deliver, receive, and/or process electrical stimulation and sensing signals to perform diaphragmatic pacing, according to various embodiments. As used herein, the terms "electronic controller," "electronic circuitry," and "electrical circuitry" may be utilized interchangeably. According to one embodiment, the electronic controller 88 includes a memory 90 that stores programmed logic 92 (for example, software). The memory 91 may also include data 94 utilized during operation and an operating system 96. For example, a processor 98 may utilize the operating system 96 to execute the programmed logic 92, and in doing so, may also utilize the data 94, which may either be stored data or data obtained through measurements or external inputs. A data bus 100 provides communication between the memory 91 and the processor 98. Users may interface with the electronic controller 88 via one or more user interface device(s) 102, such as a keyboard, mouse, control panel, or any other devices suitable for communicating digital data to the electronic controller 88. The user interface device(s) 102 may communicate through wired communication, which may be removably coupled to the pulse generator during implantation or during servicing, or may communicate wirelessly, such as through radio frequency, magnetic, or acoustic telemetry, for example. According to various embodiments, the electronic controller 88 provides the programmed logic described herein and may be embodied in software, hardware, firmware, or any combination thereof.

The elements of the pulse generator, for example the electronic controller 88, may be discrete components, or some or all elements may be based on VLSI technology, having many components embedded within a single semiconductor. In one embodiment, the electronic controller 88 is integrated with a flexible printed circuit board constructed from, for example, a polyimide film, e.g., Kapton™ (E.I. du Pont de Nemours & Co. (Wilmington, Del.)). A suitable electronic controller 88 may include more or less than all of the elements described herein. Although the electronic controller 88 illustrated in FIG. 5 is described as including each individual component internally within a single controller, multiple electronic controllers 88 may be employed, for example, each performing individual functions and/or each performing redundant functions of the other. Some of the components illustrated in FIG. 5 may exist external to the controller housing 50 and the patient, for example, within a separate processing unit, such as a personal computer and the like, in communication with the controller housing 50.

The power source 82 illustrated in FIG. 4 may be a battery of any known chemistry, for example a battery having high voltage, high capacity, low self-discharge, long durability, and that is non-toxic. Example battery chemistries may include, but are not limited to, lithium iodine, lithium thionyl chloride, lithium carbon monoflouride, lithium manganese oxide, and lithium/silver-vanadium-oxide. In another embodiment, the power source 82 may include one or more rechargeable batteries. Example rechargeable battery chemistries may include, but are not limited to, lithium ion, LiPON, nickel-cadmium, and nickel-metal hydride. The power source 82 may comprise more than one battery, for example a primary battery and a back-up battery, or in another example, certain pulse generator 51 elements may be powered by a first battery and certain other elements may be powered by a second battery.

Because the pulse generator 51 is implantable within the trachea or the primary bronchus, and thus relatively close to the patient's surface, a rechargeable power source 82 may be charged using electromagnetic charging, as is known. Other wireless charging methods may be used, such as, magnetic induction, radio frequency charging, or light energy charging. Embodiments including a rechargeable power source 82 may be charged by direct charging, such as may be deployed by a catheter, through an endotracheal tube, or during bronchoscopy, for example, to a charging receptacle 108, feedthrough, or other interface optionally included in the controller housing 50 and in electrical communication with the power source 82. The charging frequency and the charging duration of the power source 82 depends on its capacity and the device usage.

In another embodiment, the power source 82 is replaceable, and the controller housing 50 is adapted for simple, safe access to the power source, memory, processor, electrical circuitry, or other pulse generator elements, while implanted within the airway. For example, the embodiment illustrated in FIG. 4 optionally includes a reattachable detachable portion of the controller housing 50. In one embodiment, the detachable portion is a replaceable removable cap 104 adapted for removably connecting to the controller housing 50 of the controller housing 50. The removable cap 104 creates a hermetic seal between the main body of the controller housing 50 and the cap 104 using a flexible o-ring 106, for example. In some embodiments, the o-ring may be constructed from elastomeric polymers, such as, but not limited to, perfluoroelastomer, silicone, acrylonitrile butadiene copolymers, butadiene rubber, butyl rubber, chlorosulfonated polyethylene, epichiorohydrin, ethylene propylene diene monomer, ethylene propylene monomer, or fluoroelastomers, or from soft metals, such as copper, gold, silver, tin, or indium. The removable cap 104 may be secured to the main body of the controller housing 50 by any fastener suitable for releasably securing two items, such as threads and threaded receiver, bolt, clamp, pin and slot, or adhesive, for example. In one embodiment, the removable cap 104 is removably secured to the proximal end of the controller housing 50, providing easier access to the components contained therein. In another embodiment, the controller housing 50 is adapted to include one or more removable caps 104 at other portions of the controller housing 50. The controller housing 50, may further include one or more recesses or protruding members to facilitate gripping the controller housing 50 during access and removal of the cap 104.

The removable cap 104 may also include means for forming an electrical contact with the power source 82, such as a standard spring, flat spring, or conical spring, such that when the cap 104 is removed the electrical contact is broken and no power is delivered to the pulse generator 51 from the power source 82. Accordingly, a controller housing 50 adapted to include a replaceable power source 82 allows for removing the cap 104, removing the power source 82, replacing the power source 82, re-securing the cap in a non-invasive, incisionless procedure, such as with the use of an endotracheal tube, a catheter, or during a bronchoscopy, for example. In one embodiment, the controller housing 50 has a substantially elongated cylindrical shape and is dimensioned to allow commercially available batteries such as one or more "AAA-size," "AAAA-size," or button cell batteries having any of the battery chemistries described herein.

Other pulse generator 51 elements housed within the controller housing 50 may be accessible by a removable cap 104, and may be accessed and/or removed while the controller housing 50 remains implanted within the patient. For example, elements that may be accessed, maintained, or adjusted via a removable cap 104 may include, but are not limited to, sensors, communication antenna, hardware, software upgrades, lead sockets, circuitry, or memory.

In another embodiment, the reattachably detachable portion is a sub-casing of the controller housing 50 that similarly provides access to one or more elements within the pulse generator. The sub-casing may be reattachably secured to the controller housing in a manner similar to that described with reference to the removable cap 104. For example, the sub-casing may provide an additional, hermetically sealed compartment, which may be in electrical communication with the remainder of the pulse generator 51. The sub-casing may be secured to the main body of the controller housing 50 by any fastener suitable for releasably securing two items, such as, but not limited to, threads and threaded receiver, bolt, clamp, pin and slot, or adhesive, for example. In one embodiment, the sub-casing may be removably secured to the proximal end of the controller housing 50, providing easier access to the components contained therein. With reference to FIG. 4, the removable cap 104 may be replaced by the detachable portion, such that instead of a cap, the detachable portion provides an additional, sealed compartment, which may be in electrical communication with the remainder of the pulse generator 51.

The one or more electrical lead sockets 90 illustrated in FIG. 4 may be an insulated, or otherwise electrically isolated, junction or feedthrough, enabling electrical communication between the one or more leads 52 and elements of the pulse generator 51, such as the electronic controller 88. As compared to conventional pulse generators implanted subcutaneously, typically requiring strict hermetic sealing, a tracheal or bronchial implanted controller housings may be less demanding. For example, the lead socket or sockets 90 may simply consist of polymeric or elastomeric seals. However, it is also appreciated that more robust sealing mechanisms, such as a glass to metal sealed or a ceramic sealed feedthrough, may be used, such as for embodiments implantable subcutaneously. Any conventional fasteners may be used to secure (e.g., removably secure) an electrical lead 52 to a lead socket 90. Removably securing the electrical leads 52 to the controller housing 50 allows flexible implantation techniques. In other pulse generator 51 embodiments, however, the one or more electrical leads 52 may be permanently integrated with the controller housing 50, and thus may not be removable.

The pulse generator 51 and controller housing 50 may optionally include one or more sensors for monitoring conditions external to the patient's body. Being implantable within the trachea or primary bronchus, the pulse generator 51 is substantially exposed to inspired air and may sense, measure, or record parameters substantially representative of the environment external to the patient's body. Examples of sensors may include, but are not limited to, a pressure sensor for monitoring the air pressure within the trachea and for evaluating the barometric pressure or a temperature sensor for estimating temperature external to the patient's body. The measured air pressure in the trachea may also be used for observing and/or recording parameters related to the patient's breathing, including, for example, respiration rate and airway pressure in the inspirium and expirium stages. Measurements related to breathing may help a physician detect, diagnose, and treat various acute and chronic lung problems, such as asthma, bronchitis, emphysema, chronic obstructive pulmonary disease, sleep apnea, shallow breathing, Cheyne-Stokes respiration disorder, or chronic intractable hiccups, for example. These sensor devices and measured parameters are illustrative; other sensor devices may be operably associated with and/or mechanically connected to the pulse generator 51 and controller housing 50, for measuring other parameters.

In another embodiment, the pulse generator 51 and controller housing 50 include at least one input/output interface (e.g., in electrical communication with the I/O interface 102 of the electronic controller 88) operable for communicating with other medical devices. For example, the pulse generator may receive signals from (and optionally transmit signals to) a mechanical ventilator and/or from a patient monitor to provide signals indicating the operation of a mechanical ventilator or the patient's breathing patterns. Receipt of such signals by the pulse generator 51 can be used when performing diaphragmatic pacing in combination with, or as an alternative to, a mechanical ventilator. In other embodiments, one or more input/output interfaces can be adapted for communication with other medical devices or any other equipment.

Representative examples of the pulse generator 51 may also include electronic circuitry and hardware for performing audio-based communication and audio-driven commands to and from the pulse generator 51, such as may be included with the communications module 86. A pulse generator 51 implanted within the airway makes it possible to use transmit such audio-driven commands, for example, voice or digitally generated audio streams, which otherwise would be substantially attenuated in conventional devices surrounded by tissues and/or fluid, to a receiver (not shown). For example, the receiver may be a microphone or other transducer. The receiver may be integrated within the pulse generator 51 and may be in communication with the electronic controller 88 for executing logic within the controller 88 and causing a response in the pulse generator 51 functioning.

Illustrative embodiments of the pulse generator 51 optionally include one or more stimulation and/or sensing electrodes (not shown) positioned on or near the controller housing 50 for substantially communicating with the inner wall of the trachea or bronchus when implanted. A housing electrode is formed from an electrically conductive member, such as a metallic member, and is in electrical communication with the electronic controller 88 within the controller housing 50, directly or by way of one or more electrical leads passing along the external surface of the casing to the one or more electrical lead sockets 90. In another example, one or more electrodes may be affixed to an anchor device and positioned to substantially communicate with the inner wall of the trachea or bronchus upon implantation of the pulse generator 51. A housing electrode integrated with the controller housing 50 or an electrode affixed to an anchor device may be operable to perform any or all of the electrical stimulation and/or sensing functions described herein. In one example, the housing electrode serves as a reference electrode when measuring electrical impedance in the diaphragm region. In another example, a housing electrode affixed to a pulse generator 51 implanted within a primary bronchus is used to electrically stimulate at least one of the right or left phrenic nerves.

Figure 6A:
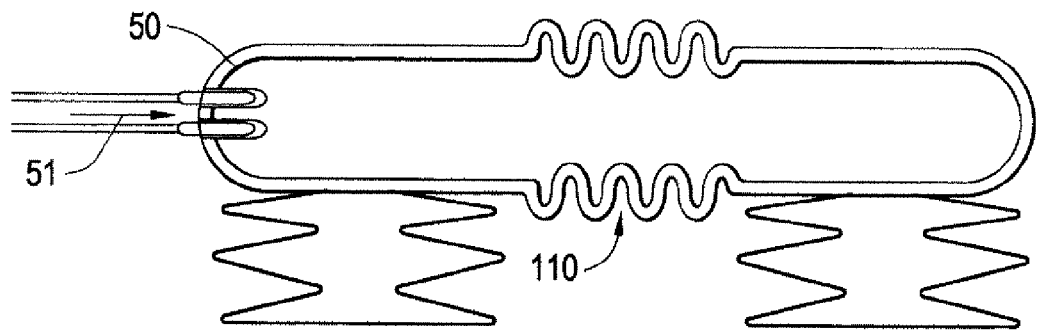
FIGS. 6A-6B are diagrams of illustrative controller housings according to some embodiments of the invention.
Figure 6B:
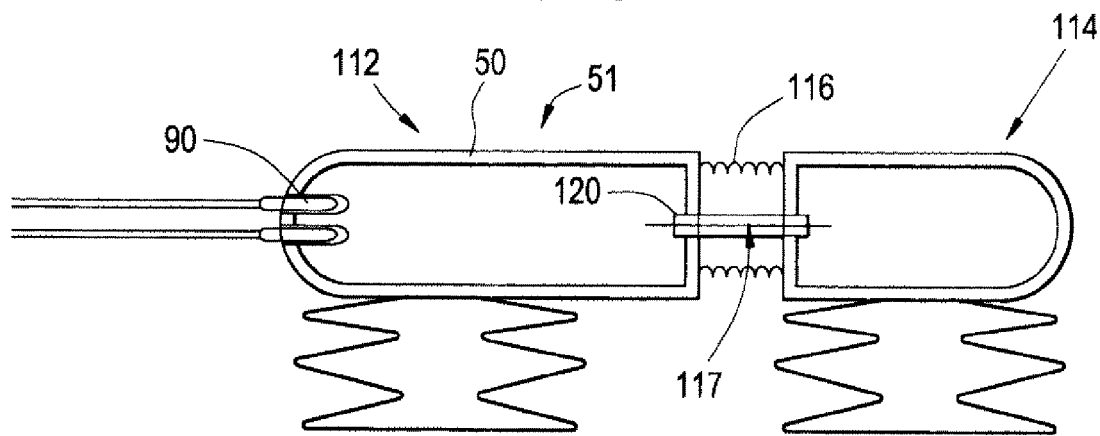

In order to facilitate insertion through either the oral or nasal cavity, in one embodiment, the controller housing 50 is at least partially flexible to ease insertion. A flexible controller housing 50 may be constructed at least partially of elastomeric materials, for example, elastomeric polymers or polyurethane. In other embodiments, a metallic controller housing 50 may include one or more areas along its axis that may bend, flex, or otherwise be malleable. FIGS. 6A and 6B illustrate two possible embodiments of a flexible controller housing 50. The controller housing 50 illustrated by FIG. 6A includes one or more corrugated areas 110, allowing the controller housing 50 to flex or bend at the corrugated areas 110. Though not illustrated, the pulse generator 51 illustrated in FIG. 6A further includes one or more of the pulse generator elements described with reference to FIG. 4; however, these elements are designed and positioned to not restrict or interfere with the flexibility of the controller housing 50.

FIG. 6B illustrates another example of a controller housing 50 configuration that also aids in longitudinal casing flexibility. This controller housing 50 embodiment includes at least two sub-cases 112, 114, each housing some of the components as described with reference to FIG. 4, and connected by one or more flexible connectors 116. Thus, the controller housing 50 of this embodiment bends or otherwise flexes around the flexible connectors 116, and is electrically connected by a non-rigid electrical conductor 117. The flexible connectors 116 may be constructed from metallic materials, polymeric materials, or any combination thereof, and may be formed to limit longitudinal (or axial) movement, but permit lateral flexion at the connectors 116. In one embodiment, the flexible connectors 116 are formed as a spring-like structure; though, other configurations suitable to provide the desired flex may be used. The non-rigid electrical conductor 117 may be an insulated, or otherwise electrically isolated lead, and may provide electrical communications between components within each sub-case 112, 114. In one example, each sub-case 112, 114 includes a hermetically sealed electrical junction 120, such as a feedthrough, operable to receive an end of the non-rigid electrical conductor 117. One or more of the sub-cases 112, 114 may be separated from the controller housing 50, for example, for servicing, programming, calibration, or data abstraction. In one embodiment, the proximal sub-case 114 (that opposite the case including lead sockets 90) houses a power source, which may be removable for charging or replacement, without requiring removal of the entire pulse generator 51 from the implantation site, thus avoiding disengaging leads, anchor devices, and the like.

Figure 7:
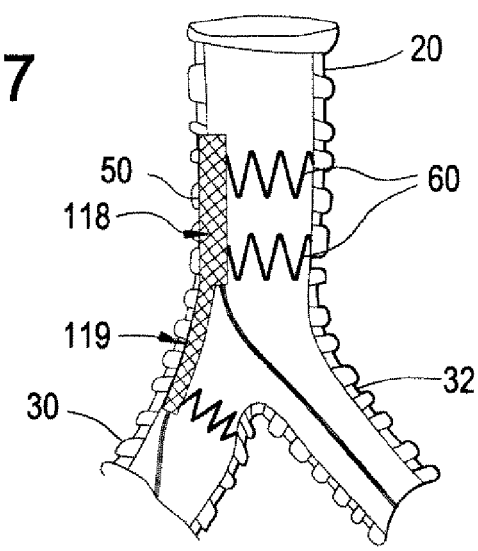
FIG. 7 is a diagram of an illustrative controller housing and device for anchoring a controller housing according to one embodiment of the invention.

FIG. 7 illustrates another possible embodiment of a controller housing 50 having a tracheal component 118 and a bronchial component 119. The controller housing 50 of this embodiment is anchored at least partially within the trachea 20 and one of the right or left primary bronchus 30, 32 as illustrated. A controller housing 50 configured in this manner can be larger in size than an embodiment implanted solely within the trachea 20 or implanted solely within the primary bronchus 30, 32. Accordingly, the diameter of tracheal component 118 may be substantially larger than the diameter of the bronchial component 119, optimizing the controller housing 50 volume while minimizing any interference to airflow through the airway. In another embodiment, the controller housing 50 is implantable within the trachea 20 and both primary bronchi 30, 32. A controller housing 50 implantable within both bronchi 30, 32 and the trachea 20 may be configured in an inverse "Y" shape (not shown), and may at least partially rest at or near the bronchial bifurcation. The controller housing 50 of these embodiments may optionally be anchored to the trachea 20, the primary bronchus 30, 32, or to both, by an anchor device, such as described herein.

Electrodes and Electrical Leads

The electrodes may be operable to provide electrical stimulation or to perform physiological sensing and measurement; though, in some embodiments the electrodes may be operable to perform both stimulation and sensing. An electrode generally includes an electrode body and at least one stimulation surface from which electrical signals may be delivered. The stimulation surface may also serve as a conductor for sensing diaphragmatic electrical activity or other diaphragmatic activity. The electrodes may be unipolar electrodes used in cooperation with another reference electrode, or bipolar or tripolar electrodes, that both include a different and an indifferent pole. In various embodiments, the electrodes are affixed or integrated with an electrical lead at or near its distal tip. However, in other embodiments, such as those including an electrical lead carrying more than one electrode, at least one electrode may be affixed to the electrical lead at a position proximal from the distal end, to allow additional stimulation or sensing at a position in the airway proximal to the distal tip of the electrical lead. In yet other embodiments, such as those described with reference to FIGS. 25A-25B, electrodes may be wireless electrodes that do not require electrical leads.

The electrodes and leads may be guided to and positioned at the desired implantation site using delivery devices, such as a catheter, a guidewire, or any combination thereof, or any other known means for guiding elongate devices within a body lumen.

The electrodes are fixable at one or more selected implantation positions within the airway to prevent electrode migration from the selected position and to promote electrical coupling with the epithelial tissue lining the airway. Various anchoring devices can be employed to fix an electrode at a selected implantation site. For example, these anchoring devices may include, but are not limited to, one or more barbs, one or more hooks, suture, one or more extensible members, one or more stent-like expandable members, a balloon, an adhesive, or any combination thereof, as described more fully herein. Barbs or hooks may be in a fixed relationship with the electrode, or may be selectably retractable by way of mechanical, electrical, chemical means, and the like. Extensible members may include, for example, members made of self expandable metals (e.g., nickel-titanium, cobalt alloy, stainless steel, shape memory alloys), members made of self expandable polymeric materials (e.g., silicone), or mechanically extensible members, such as those stent-like expandable members described with reference to FIGS. 3A-3E for use in conjunction with the controller housing 50.

In one embodiment, the one or more electrodes are proportioned to have a diameter slightly larger or approximately the same size as the inner bronchi at the selected implantation site, causing the electrode to substantially lodge within the airway. Electrode embodiments proportioned to lodge within the airway as a result of its diameter may optionally include a lumen or passageway formed axially through the body of the electrode and in parallel with the airway lumen to permit airflow through the passageway or lumen, thus avoiding interference with respiratory activities occurring at or downstream of the implantation site.

In some embodiments, the electrode or electrodes may be at least partially coated with an insulating material. Examples of suitable materials may include, but are not limited to, a polymer insulator (such as silicone, polyurethane, polytetrafluoroethylene (e.g., Teflon™), or other fluoropolymers), a ceramic insulator, or a glass insulator. An insulative coating enables the control, direction, and focus of the stimulation signal sent by the pulse generator. An insulative coating also allows dividing the electrode into multiple electrode stimulation regions for optimizing the stimulation location and/or for operating in a multi-electrode configuration, such as a bipolar or tripolar electrode.

FIGS. 8A-8G illustrate several example embodiments of electrode configurations that facilitate fixation and retention within the airway, improve electrical coupling, and may or may not permit airflow past the implanted electrode, i.e., past the implantation site. Example electrode configurations and anchor devices are similar in design and function to those described with reference to the controller housing anchor devices. Accordingly, any of the anchor device embodiments described with reference to the controller housing herein may be applied as anchor devices for an electrode, and any anchor device embodiments described with reference to the electrodes herein may be applied as anchor devices for the controller housing.

Figure 8A:
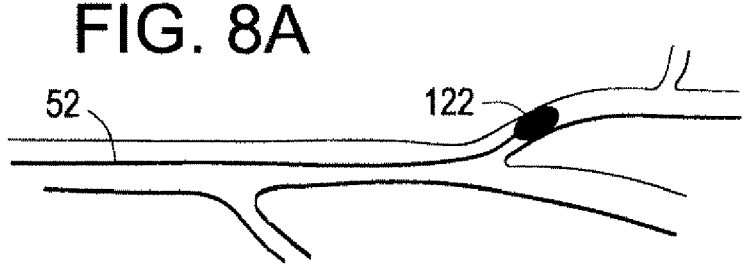
FIGS. 8A-8F are diagrams of illustrative electrodes according to some embodiments of the invention.

FIG. 8A illustrates an electrode 122 positioned at the distal tip of an electrical lead 52 and implantable within the airway of a patient, for example, within the trachea, primary, secondary, or tertiary bronchus, bronchioles, or any branch thereof. The diameter of the electrode 122 is substantially similar or slightly larger than the inner diameter of the airway at the selected implantation site. For example, an electrode 122 proportioned for placement at an implantation site in the tertiary bronchus may have a diameter of approximately 5 mm to approximately 8 mm if the inner diameter of the tertiary bronchus is approximately 5 mm. Accordingly, in some embodiments, the diameter of an electrode 122 may be 0 mm to approximately 8 mm greater than the inner diameter of the airway at the implantation site. The inner diameter of a patient's airway varies depending upon the location within the airway and upon the patient; thus, the diameter of an electrode 122 in accordance with the embodiment illustrated in FIG. 8A also will vary depending upon the intended implantation site dimensions. An electrode 122 having a diameter substantially similar or slightly greater than airway lumen in which it is implanted will aid electrode 122 retention at the implantation site and promote electrical coupling for more effective stimulation or sensing. Additional anchor devices, such as texturing, suture, barbs, hooks, studs, adhesive, shape memory alloy members, or any combination thereof, may optionally be included to enhance electrode 122 retention in the airway. Accordingly, for certain electrode embodiments also including additional anchor devices, the electrode diameter need not be the same or slightly larger as the airway, but may optionally be a slightly smaller diameter than the airway.

The embodiment illustrated in FIG. 8A, without further design enhancements, may inhibit airflow downstream from the implantation site. Accordingly, this embodiment may be generally suited for implantation sites located in the periphery of the bronchi having relatively smaller diameters such that the restricted airflow passage may be clinically insignificant, for example, within smaller branches of the tertiary bronchi or within the bronchioles.

Figure 8B:
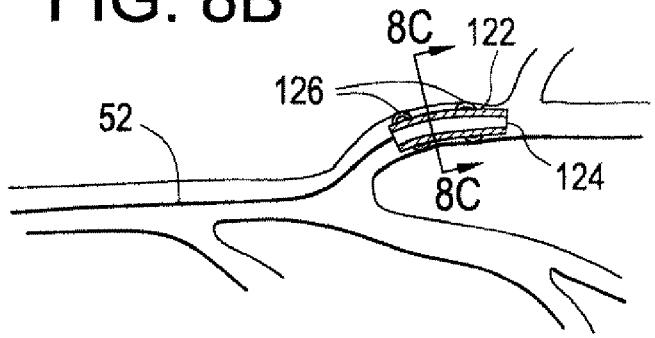

FIG. 8B illustrates another example of an electrode 122 that includes at least one a lumen or passageway 124 extending axially through the electrode 122 to permit airflow through therethrough. The lumen 124 extends axially from the electrode's 122 proximal end to its distal end, and may be centered radially or offset from the central axis of the electrode 122. The lumen 124 is proportioned to permit substantial airflow to pass therethrough. The lumen 124 may further provide a passageway with which delivery devices may cooperate, such as a guidewire, a bronchoscope, and the like for deploying and/or securing the electrode at the implantation site. An offset lumen 124 leaves greater room within the electrode 122 body for electrical circuitry or sensing components as may be called for. In another similar electrode embodiment, a recess (not shown) may be formed in one or more external surfaces of the electrode 122 and extend from the proximal end to the distal end. When implanted in the airway, an electrode 122 having a recess leaves a passageway through which air may pass between the recess and the inner wall of the airway. In addition to the lumen 124 or recess, the electrode 122 body may include one or more protrusions 126, such as studs, barbs, hooks, shape memory alloy members, or any combination thereof, extending substantially radially from the electrode 122 body for engaging the inner wall of the airway to aid in electrode 122 fixation. Furthermore, one or more of the protrusions 126 may be formed from the electrically conducting material of the electrode 122 to promote electrical coupling by improving surface area contact with the inner wall of the airway.

Figure 8D:
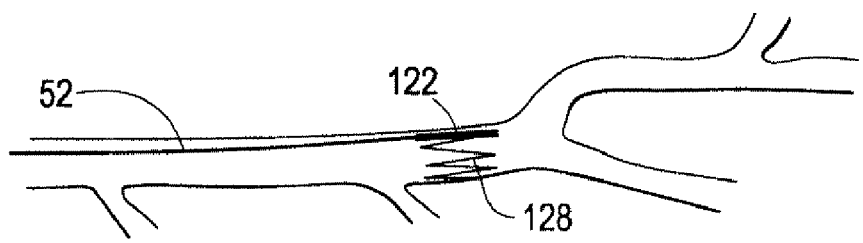
Figure 8E:
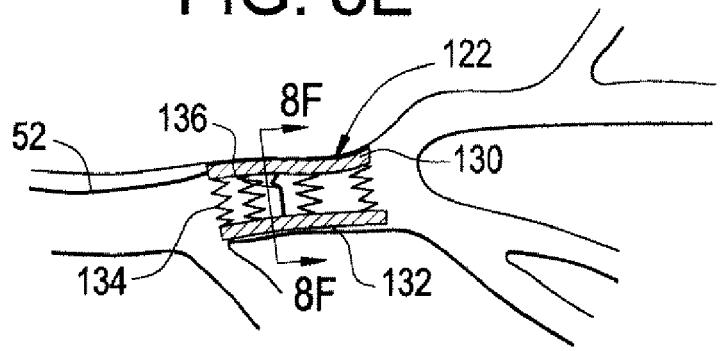
Figure 8C:
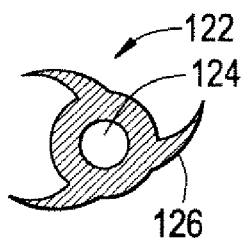

FIG. 8C illustrates a cross-section of the electrode 122 embodiment illustrated in FIG. 8B. Accordingly, this embodiment includes a lumen 124 passing through the electrode 122 body and multiple protrusions 126 extending from the body. As illustrated in FIG. 8C, the protrusions 126 may have a hook shape; though, other shapes may be employed, such as pointed, barbed, rounded, and the like. The protrusions 126 illustrated in FIGS. 8B and 8C are equally applicable to other electrode embodiments described herein.

FIG. 8D illustrates another electrode 122 embodiment including an anchor device 128 similar to those described with reference to FIGS. 3A-3E for use with the controller housing. In this embodiment, the anchor device 128 is an extensible anchor device, such as a stent-like expandable member, as further described herein. Other anchor devices 128 may include one or more radially expandable circumferential rings, balloon sleeves, radially extensible rigid members, tubular members, texturing, suture, barbs, hooks, studs, adhesive, shape memory alloy members, or any combination thereof. In one embodiment, the anchor device 128 is formed from electrically conductive material and serves as part of the electrically conductive electrode 122 function, to further promote electrical stimulation or sensing effectiveness.

Figure 8F:
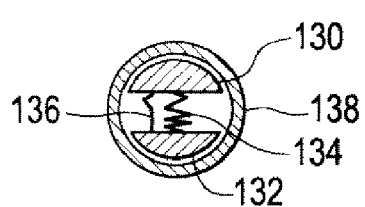

FIGS. 8E and 8F illustrate another embodiment of electrode 122, which includes at least two electrode sub-components 130, 132 configured similarly to the controller housing configuration described with reference to FIGS. 3C and 3D. The at least two electrode sub-components 130, 132 are connected by one or more expandable connectors 134 which create opposing forces against the two electrode sub-components 130, 132, radially biasing each against the inner wall of the airway at opposite areas. The expandable connector 134 and electrode sub-components 130, 132 fix the electrode 122 at the implantation site while leaving a passageway between the electrode sub-components 130, 132 through which airflow may pass. The expandable connector 134 may be configured similarly to any of the expandable members described herein with reference to electrode and/or controller housing embodiments. In various embodiments, the expandable connectors 134 may be formed as a metallic or polymeric spring, from a shape memory alloy, as mechanically adjustable rigid members, as telescoping members, and the like. In one embodiment, the two electrode sub-components 130, 132 are electrically coupled by one or more isolated electrical connector 136, to facilitate electrical communication between each electrode sub-components 130, 132. In another embodiment, the one or more expandable connectors 134 may double as an isolated electrical connector, eliminating the need for an additional isolated electrical connector.

As illustrated in FIG. 8F, the two or more electrode sub-components 130, 132 connected by one or more expandable connectors 134 may be compressed to a reduced profile during deployment and positioning, for example using a delivery device 138, such as a catheter or other cannula. In one embodiment, the two electrode sub-components 130, 132 each have a substantially semi-circular cross section, each being complementary in shape to the other, and having an external radius of curvature substantially similar to the inner wall of the airway in which it may be implanted. Although the embodiment illustrated by FIGS. 8E and 8F includes only two electrode sub-components, the electrode 122 may be formed from any number of electrode sub-components, each being biased radially against the inner wall of the airway implantation site. In another embodiment, only one of the electrode sub-components 130, 132 is electrically conductive and serves the electrode function.

Figure 8G:
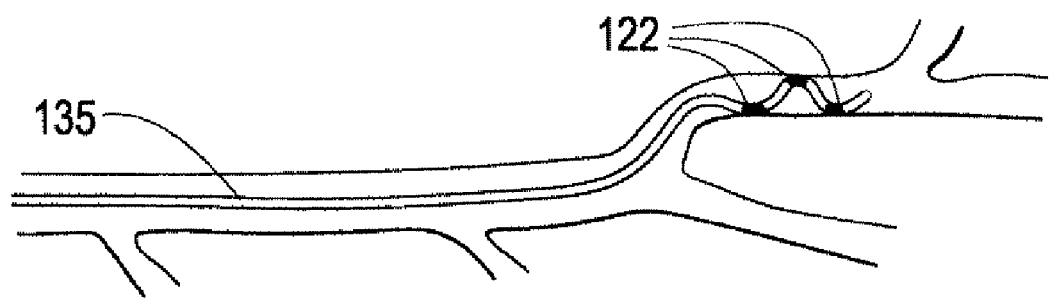

FIG. 8G illustrates another suitable electrode and electrical lead embodiment including at least one electrode and at least one pre-shaped electrical lead. The distal end of the pre-shaped electrical lead 135 is pre-shaped, such that the shape will substantially lodge or wedge within the lumen of the airway in which it may be implanted. As illustrated in FIG. 8G, the pre-shaped electrical lead is shaped substantially waved shape, such as an "S" shape, such that the wave amplitude may be substantially similar or slightly larger than the inner diameter of the airway lumen in which it may be implanted. In other embodiments, the pre-shaped electrical lead 135 may be formed in other shapes, such as, but not limited to, a spiral, circular, elliptical, or hooked, for example. The pre-shaped electrical lead 135 carries one or more electrodes 122. The embodiment illustrated in FIG. 8G includes three electrodes 122, positioned at or near the distal portion, and then along the pre-shaped portion of the electrical lead 135. Positioning the one or more electrodes 122 at or near a maximum or minimum of the pre-shaped form causes the electrode or electrodes 122 to be biased against the inner wall of the airway lumen, thus increasing the electrical coupling therewith.

The pre-shaped portion of the electrical lead 135 may include a less pliable, less flexible and more shape resilient material than the remaining proximal portion of the lead 135. In one example, the pre-shaped portion of the electrical lead is coated or otherwise constructed at least partially with polyurethane whereas the remaining proximal portion may be coated or constructed at least partially with silicone. In another example, a shape memory alloy, such as nickel titanium alloy, is integrated with the pre-shaped portion of the electrical lead 135, such that upon application of energy, the electrical lead 135 can transition from substantially straight shape to assume any pre-defined shape, for example, an "S" shape as illustrated.

A pre-shaped electrical lead 135 carrying one or more electrodes 122 may be deployed using a delivery device, such as a catheter, sheath, stylet, or guidewire. Accordingly, when contained within a lumen of the delivery device, the pre-shaped electrical lead 135 is substantially straightened for delivery and positioning at or near the implantation site. Upon removing the delivery device, the pre-shaped portion of the electrical lead 135 reforms to it's pre-shaped form, causing it to apply a force against the wall of the airway lumen and substantially affix the electrode 122 and electrical lead 135 in place.

Figure 8H:
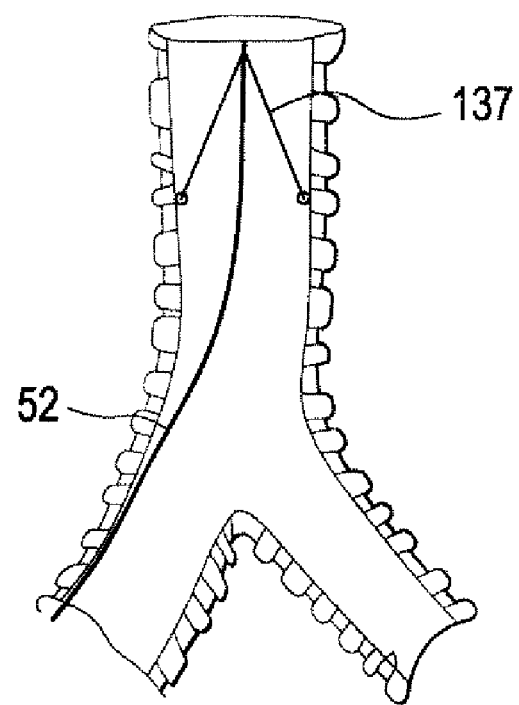
Figure 8I:
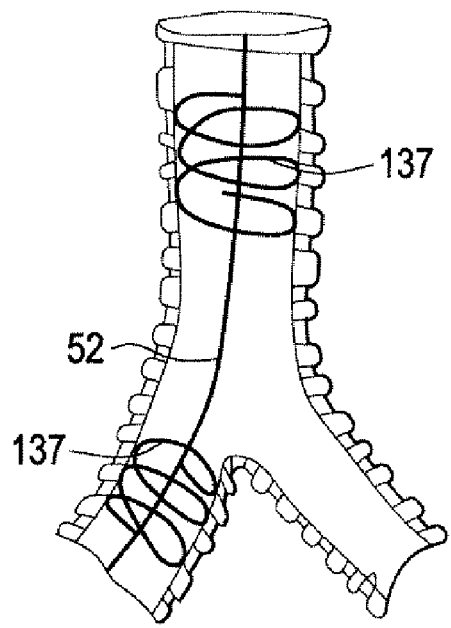

FIGS. 8H-8K illustrate some embodiments of electrical leads 52 that include at least one lead securing member 137 for substantially retaining the electrical lead 52 at a certain position within the airway, such as the trachea or bronchus. Because the electrical lead 52 is a foreign object to the airway tissues, irritation may occur, causing discomfort and/or other undesirable conditions, such as chronic coughing, itching, or tissue granulation. In one embodiment, as illustrated in FIG. 8H, at least two lead securing members 137 may be formed as a pin, arm, rod, or other member extending radially from the electrical lead 52 in approximately opposite directions and substantially affixing to, or exerting pressure against, the inner wall of the airway in which the electrical lead 52 is positioned, and the electrical lead 52 is suspended therebetween. In another embodiment, as illustrated in FIG. 8I, the lead securing member 137 may be formed as a coil or other radially extending elliptical member, such that the lead securing member at least partially contacts the circumference of the inner wall of the airway and the electrical lead 52 is suspended therebetween. The lead securing members 137 illustrated in FIGS. 8H and 8I allow the electrical lead 52 to be suspended within the interior lumen of the airway, and avoid substantial contact with the inner wall.

Figure 8J:
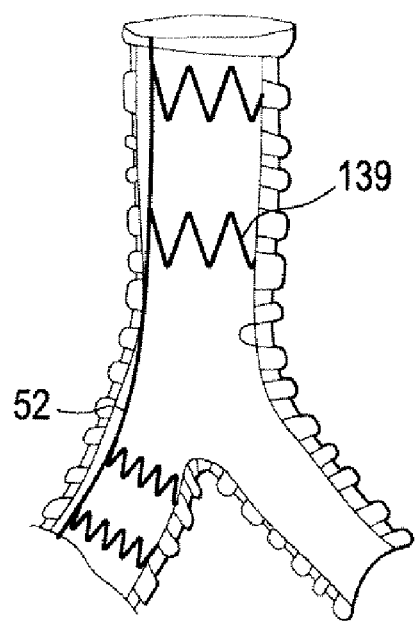
Figure 8K:
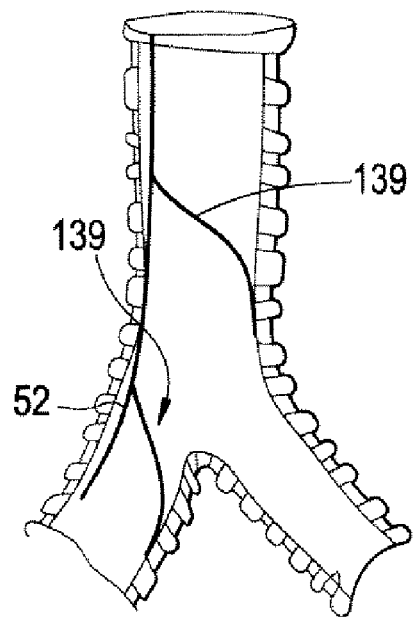

FIGS. 8J and 8K illustrate still other embodiments of lead securing member 139 which biases the electrical lead 52 toward the inner wall of the airway, such as against the trachea or bronchus. In this way, the electrical lead 52 may be at least partially or totally encapsulated by the epithelial tissue of the airway inner wall to allow the body's natural mechanisms to protect against and combat contamination, such as bacteria or infection resulting therefrom. In one embodiment, as illustrated in FIG. 8J, the lead securing member 139 is an expandable member, similar to those described with reference to FIG. 3A or 8D, that exerts a radially biasing force against the inner wall of the airway and causes the electrical lead 52 to interface with the inner wall opposite the lead securing mechanism 139. In this example, the lead securing member 139 is configured as an expandable member, such as, but not limited to, a stent-like member, an inflatable balloon sleeve, a spring, or a coil. In another embodiment, as illustrated in FIG. 8K, the lead securing member 139 is configured as a pin, arm, rod, or other member extending radially from the electrical lead 52 in an approximately opposite direction and substantially affixing to or exerting pressure against the inner wall of the airway opposite the electrical lead 52. The lead securing member of this embodiment creates a biasing force which causes the electrical lead 52 to interface with the inner wall opposite the lead securing member 139. In still another embodiment, the lead securing member 139 may be like one of the electrode anchor devices or controller housing anchor devices described herein and illustrated in FIG. 3A, 3B, 3E, 3F, or 8D. The lead securing members 137, 139, as described herein, may be formed of a biocompatible elastomeric material or shape memory material. Examples of these materials include, but are not limited to, elastomeric polymers (such as silicone, polyurethane), flexible metals, and shape memory alloys (e.g., Nitinol™).

The electrical leads carrying one or more electrodes may be of any known design, including unipolar, bipolar, tripolar, multi lumen, single lumen, coaxial, or bifurcated. The electrical lead may be insulated, for example by silicone, polyurethane, silicone with polyurethane overlay, or any other material known in the art to be suitable for electrically isolating medical leads.

In some embodiments, the electrical lead may have a variable length. For example, in one embodiment, an electrical lead is longitudinally extensible and retractable to aid in deployment and implantation of the electrode or the pulse generator. As another example, the electrical lead is configured as an expandable and retractable coil or in a telescoping configuration. The ability to change the electrical lead length facilitates implanting the one or more electrodes and the pulse generator. In other embodiments, however, the electrical lead length may not be independently variable, but are adjustable when securing to the pulse generator during implantation.

The electrical leads may also optionally include a radiopaque coating or a radiopaque material to aid in deployment when using imaging techniques, such as x-ray, computed tomography, or fluoroscopy, for example. Furthermore, illustrative electrical leads may be capable of eluting and/or delivering medicinal agents to reduce rejection of the lead and electrode by the surrounding tissue, therefrom. For example, the electrical leads may be coated with steroids, anti-inflammatory agents, anti-bacterial agents, antibiotics, or any combination thereof, as are known. In other embodiments, the electrical lead may include a lumen existing therethrough for selective delivery of such medicinal agents, for example, during electrode deployment as administered by the physician, or while implanted as released from the pulse generator or other source.

Figure 9A:
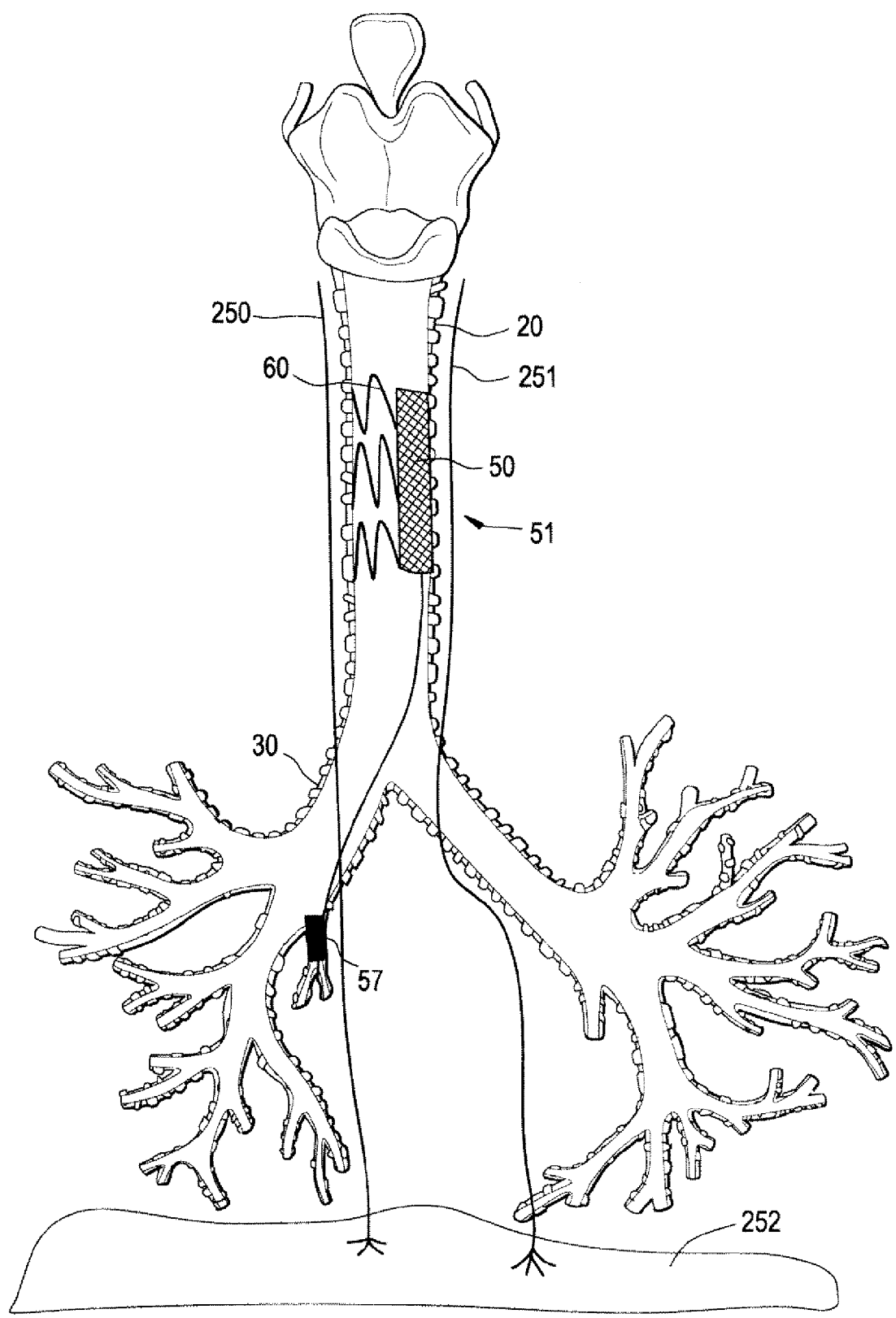
FIGS. 9A-9D are diagrams of illustrative diaphragm pacing device placements according to some embodiments of the invention.

FIGS. 9A-9D illustrate additional embodiments of an implantable diaphragmatic stimulation system having one or more electrodes positioned and fixed at various positions within a human airway. FIG. 9A illustrates one embodiment of an implantable stimulation system to innervate the right side of the diaphragm 252 that includes a single electrode 57 carried by an electrical lead 52 implanted within the right tertiary bronchus or substantially near the right phrenic nerve 250. In another embodiment, the electrode 57 may be positioned within the airway at higher or lower levels of the bronchial tree to be in proximity to the right phrenic nerve 250. In this embodiment, the system is operable for monitoring diaphragmatic electrical and/or mechanical activity to identify respiratory deficiencies, including, but not limited to, breathing patterns, lack of breathing, shallow breathing, interrupted breathing, sleep apnea, or chronic intractable hiccups, for example. The single electrode 57 may also be used to stimulate the right vagus nerve by delivering appropriately timed electrical pulses from the pulse generator.

Though not illustrated, the implantable diaphragmatic stimulation system may include positioning a single electrode at other positions within the bronchi to be in proximity to other areas of the phrenic nerves network. For example, in another embodiment (similar to that shown in FIG. 9C), the electrode may be placed within the left bronchus and in proximity to the left phrenic nerve 251, in a manner similar to that illustrated for the right side in FIG. 9A, for electrically stimulating the left side of the diaphragm 252.

Figure 9B:
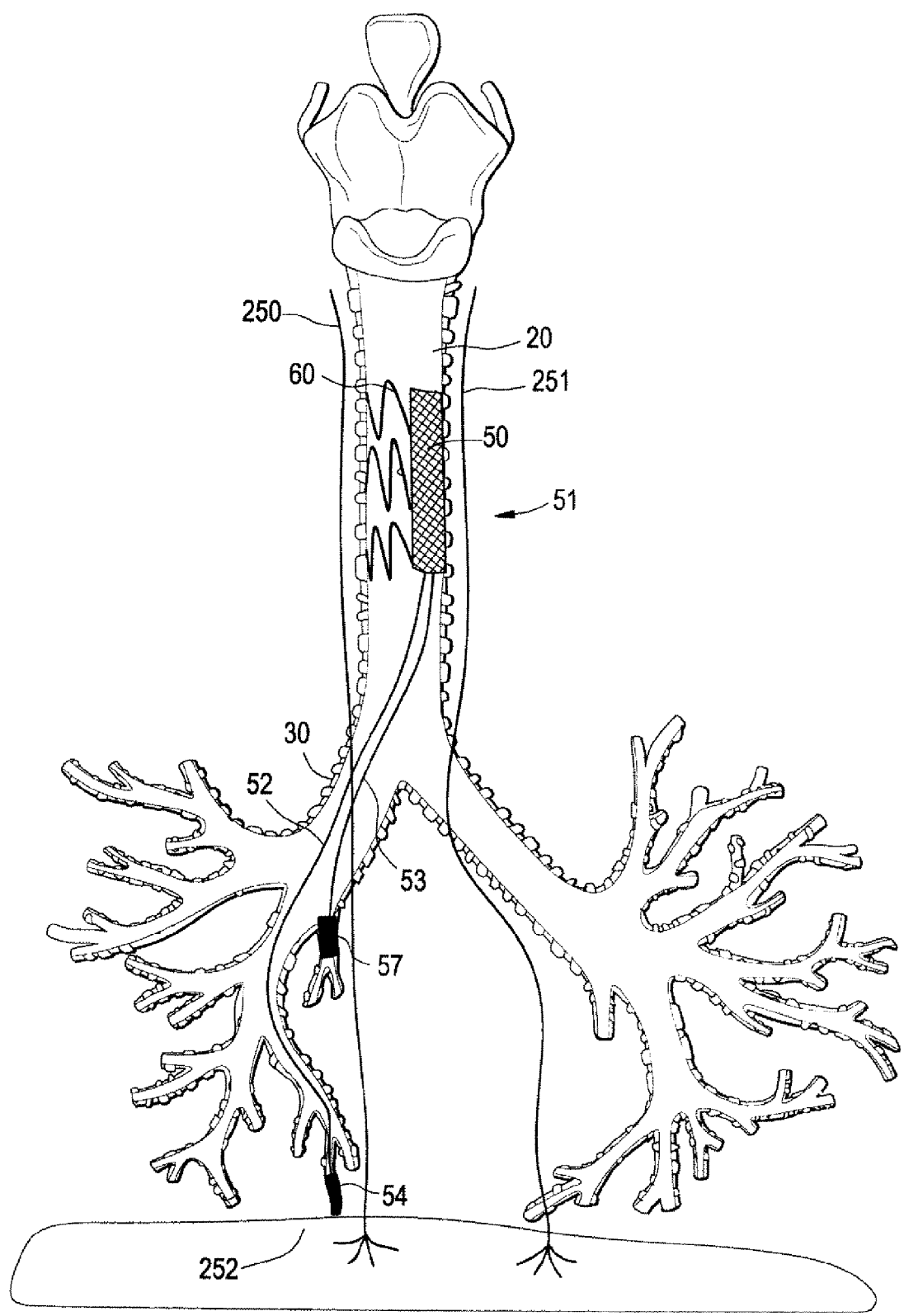

FIG. 9B illustrates another embodiment of an implantable stimulation system to innervate the right side of the diaphragm 252, which includes two electrodes 54 and 57 carried by electrical leads 52 and 53 respectively and implanted within the right bronchial tree. A first electrode 57 is implanted in substantial proximity to the right phrenic nerve 250 and a second, distal electrode 54 is implanted in a distal part of the bronchial tree in proximity to the diaphragm 252. This embodiment is operable to perform diaphragmatic pacing of the right side of the diaphragm 252 by innervating the right phrenic nerve 250 or by stimulating the nerves in proximity or on the diaphragm 252. In one embodiment the electrodes 54, 57 are operable to stimulate simultaneously. Though, in other embodiments, only a single electrode is operable for stimulating the diaphragm 250, while the other electrode performs sensing. In another embodiment, the active electrode or electrode combination is selected manually or automatically based on the a desired pacing configuration. The desired stimulation signal patterns delivered by the pulse generator may be selectable from one or more pre-defined signal patterns, or may be defined by based on criteria including, but not limited to, minimal energy consumption, minimum voltage, patient comfort, or any combination thereof.

Furthermore, in embodiments in which the controller housing or the anchor device includes an additional electrode, as described herein, the system illustrated in FIG. 9B may be operable to perform diaphragmatic pacing, such that the controller housing electrode 51 serves as the counter electrode to the distally placed electrode 54. In another embodiment, the first electrode 57 is operable to serve as a counter electrode to the distally placed electrode 54.

Figure 9C:
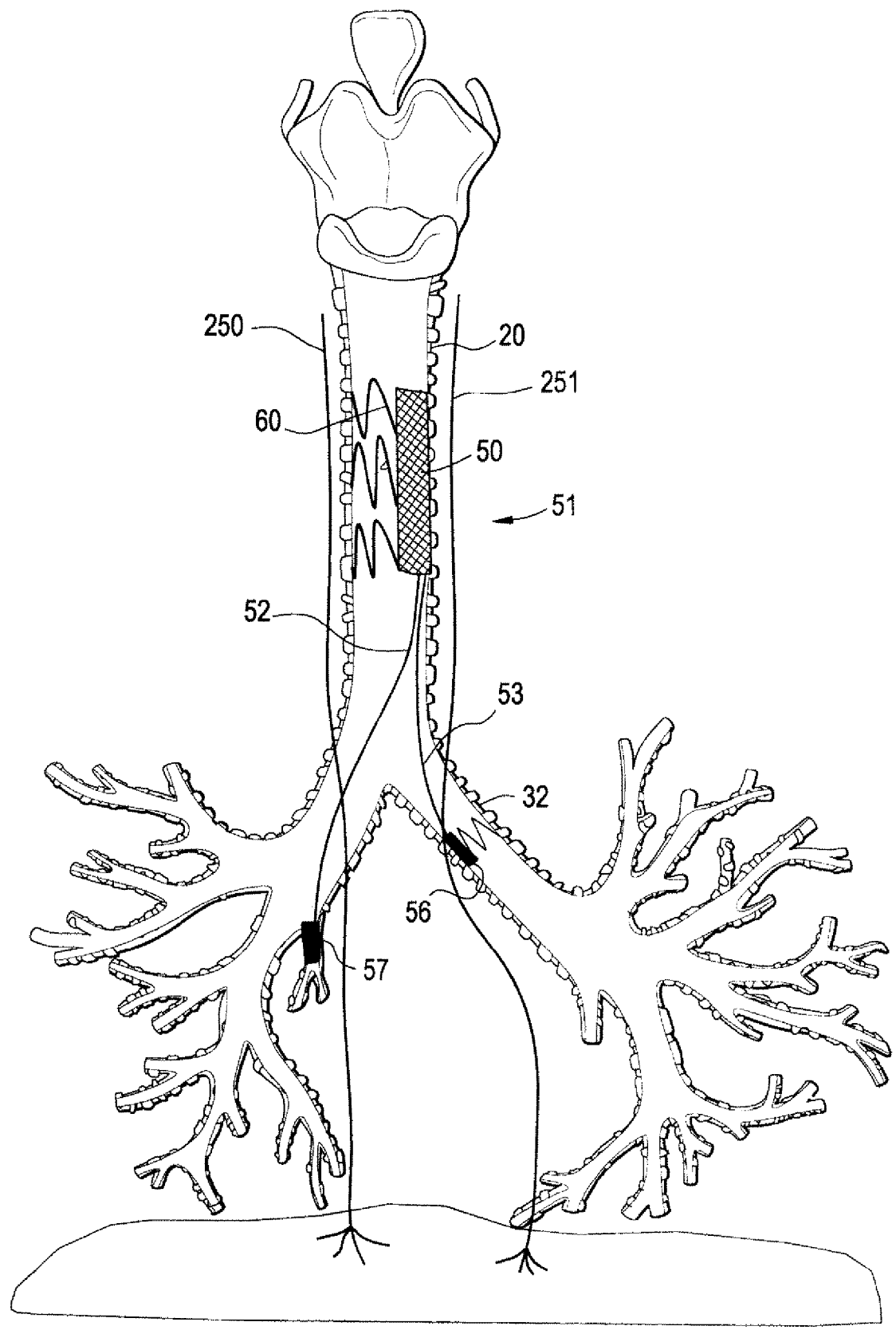

FIG. 9C illustrates another embodiment of an implantable diaphragmatic stimulation system including at least two electrodes 57, 56 carried by electrical leads 52, 53 in electrical communication with a pulse generator 51, each implanted at different sites within the right and the left bronchus. Accordingly, one electrode 57 is positioned in proximity to the right phrenic nerve 250 and one electrode 56 is positioned in proximity to the left phrenic nerve 251. The electrodes 57,56 are operable to perform diaphragmatic pacing by controlling the delay, and in optionally the amplitude, of the electrical pulse to synchronize the contraction between the left and right sides of the diaphragm 252. The embodiment of FIG. 9C may also be adapted for stimulating intercostal nerves, which control the intercostal muscles.

Figure 9D:
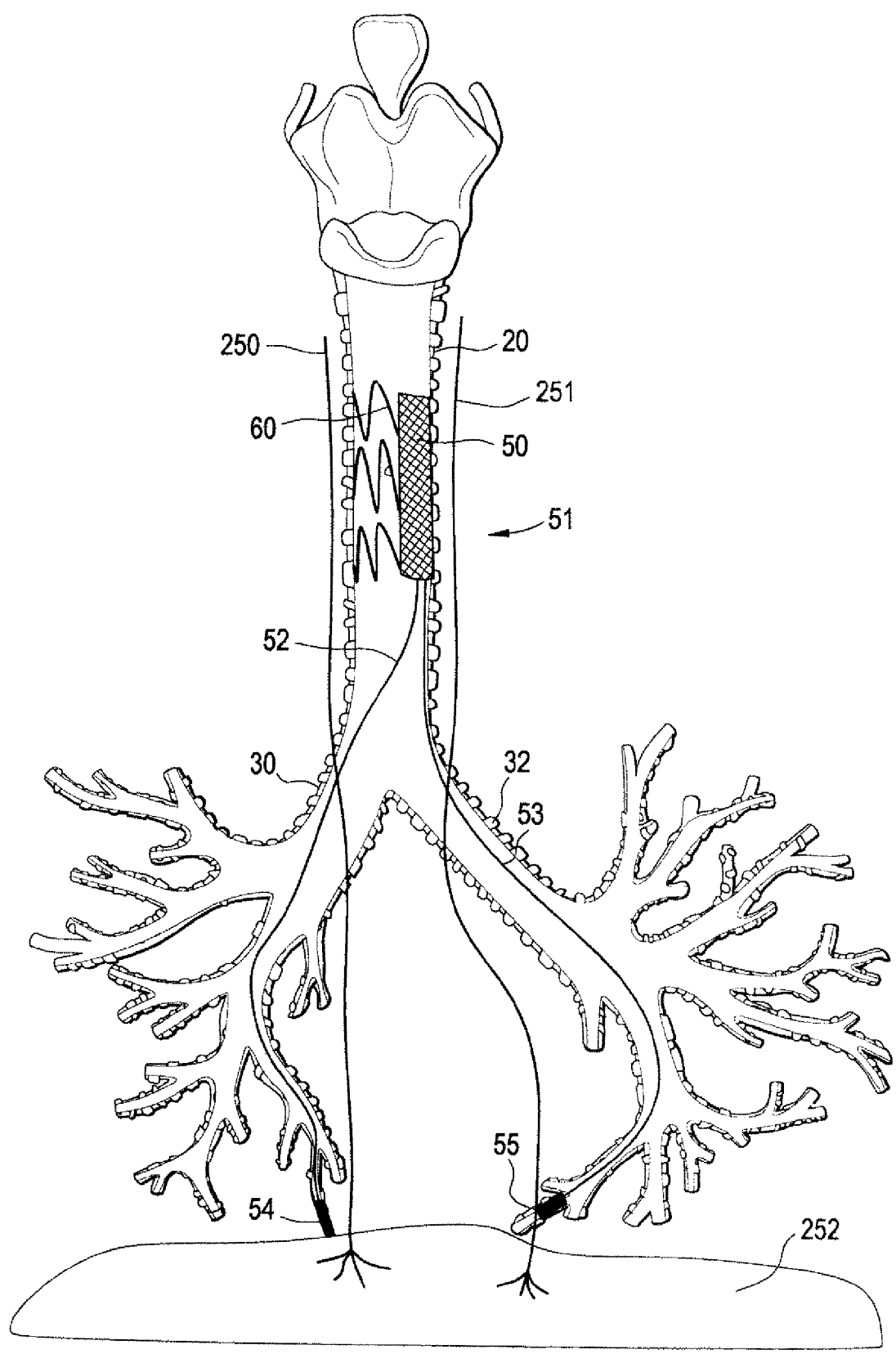

One variation of the embodiment illustrated in FIG. 9C may include one or two additional electrodes implanted distally within the right bronchus and/or left bronchus and in proximity to the diaphragm 252, such as at positions similar to those illustrated in FIG. 9D, for example. Additional electrodes positioned distally an in proximity to the diaphragm 252 may be stimulated in coordination with the electrodes 57, 56 positioned near the right and left phrenic nerves, respectively, to synchronize contraction of the diaphragm 252.

FIG. 9D illustrates another embodiment of an implantable diaphragmatic stimulation system including two electrodes 54, 55 carried by electrical leads 52, 53, respectively. One electrode 55 is implanted in the left tertiary bronchus in proximity to the left side of the diaphragm 252 and the other electrode 54 is implanted in the right tertiary bronchus in proximity to the right side of the diaphragm 252. This embodiment is operable to perform diaphragmatic pacing, such as dual pacing of the diaphragm left and right sides or single side pacing performed by electrode 55 or by electrode 54, and optionally sensing by the other electrode not delivering a stimulation signal. This embodiment may further be operable to provide non-respiratory treatment that may be delivered by stimulating the diaphragm, including increasing intra-abdominal pressure to assist expelling vomit, feces, and/or urine from the body, or applying pressure on the esophagus as it passes through the esophageal hiatus to control acid reflux.

The electrode configurations illustrated in FIGS. 2 and 9A-9D are provided for illustrative purposes only, and other electrode placements within the bronchi or trachea, or any combinations of those described herein, may also be employed to induce breathing and/or diaphragmatic stimulation and/or sensing. Moreover, according to other embodiments, electrodes positionable in a patient's airway may be used in combination with conventionally implanted electrodes, such as phrenic nerve cuff electrodes or diaphragmatic surgically implanted electrodes, with conventional epidermally placeable electrodes, and/or with mechanical ventilation treatments.

Sensing Function

As described with reference to various embodiments, the diaphragm stimulation system may be operable to perform sensing functions as well as electrical stimulation. Physiologic electrical activity, such as electrical potential, impedance, or other physiological parameters of the heart and/or lungs for example, may be measured by the diaphragmatic stimulation system. In one embodiment, one or more electrodes and the pulse generator may be operable to perform the physiological electrical activity sensing, in addition to or instead of electrical stimulation described herein. In another embodiment, the system may include one or more sensors operable for performing mechanical measurements, such as position, pressure, temperature, gas flow, acceleration, or strain, for performing optical measurements, such as imaging, absorption, or fluorescence, or for performing ultrasonic imaging, or any combination thereof. Furthermore, one electrode may be operable to perform both sensing and electrical stimulation functions, thus reducing the number of electrodes and electrical leads implanted within the airway.

As described herein, with reference to FIGS. 2 and 9A-9D for example, in one embodiment, at least one electrode operable for sensing may be positioned away from the stimulation site to serve as a counter electrode for measuring diaphragm or phrenic nerve electrical activity, such as electrical impedance, between one or more other electrodes implanted in various positions within the airway. In another embodiment, the electrodes may also be used for monitoring cardiac activity. For example, ventricular tachycardia may be detected by monitoring electrical activity of the left ventricle or alternatively the right ventricle. As another example, electrodes implantable in the airway may also detect other heart conditions, such as myocardial infarction and atrial fibrillation, for example.

In another embodiment, electrical impedance may be measured across a substantial area of the lungs due to the various sensor electrode implantation sites available within the bronchi, such as those locations illustrated in FIGS. 2 and 9A-9D. For example, electrical impedance may be measured between two sensing electrodes implanted within the bronchi, such as between the tertiary bronchi or bronchioles, of a single lung, or between the tertiary bronchi or bronchioles of the left lung and the tertiary bronchi or bronchioles of the right lung. Implanting sensing electrodes within the airway focuses electrical impedance measurements one the lungs, and may be achieved through minimal or no contribution from external devices, thus providing more accurate measurements than from conventional systems having electrodes implanted outside of the airway. However, in other embodiments, one sensing electrode may be implantable within the airway while a reference electrode may be positionable outside of the lungs, such as an electrode associated with a pulse generator or anchor device implantable within a trachea or primary bronchus, an electrode implantable subcutaneously, or an epidermally placeable electrode (e.g., externally affixed to a patient's upper torso). Measuring electrical impedance in the lungs can correlate to the amount of fluids accumulated within a patient's lungs, which may be used to for early detection of congestive heart failure and decompensation resulting therefrom, or for detection of other diseases or conditions that may affect electrical impedance across the lungs or other areas within the thoracic cavity.

In other embodiments in which the pulse generator or the anchor device includes an electrode, the electrical impedance may be measured between one or more other implanted electrodes and the pulse generator or anchor device electrode. For example, a device having a pulse generator electrode implanted within the trachea and at least one electrode implanted within a tertiary bronchus or a bronchiole may provide electrical impedance measurements from between the two electrodes and thus across a substantial portion of the lungs or the heart.

In addition to monitoring diaphragm electrical activity or cardiac electrical activity, one or more other sensors may be carried by an electrical lead for sensing mechanical activity of the diaphragm, lungs, and/or heart. For example, one or more sensors, such as an accelerometer, a strain gauge, a pressure transducer, or other sensors suitable for measuring position or movement, located within the bronchi in close proximity to the diaphragm, may sense movements resulting from various sources, including thoracic diaphragm movement, lung movement during breathing, and cardiac contractility. Because the lungs are mechanically coupled to the diaphragm and to the heart, diaphragm movement and/or cardiac movement, such as cardiac contractility, may be measured by sensing lung movement. Lung movement caused by breathing is characterized by relative slow acceleration compared to cardiac contraction and may be substantially isolated, filtered, separated, or otherwise distinguished through signal processing, such as filtering, to distinguish breathing movement form cardiac movement. Signal processing may be performed by the pulse generator or other electrical circuitry existing within the controller housing or external to the patient. Measuring lung movement may be useful for detecting respiratory irregularities or conditions for coordinating and/or synchronizing respiratory therapy treatment, such as diaphragmatic pacing, as is described in detail herein. Measuring cardiac movement may be useful for detection of atrial fibrillation, ventricular fibrillation, bradycardia, or myocardial infraction, for example.

In one embodiment, the distal tip of the electrical lead or sensor may include a needle or probe to pierce the airway wall and secure the sensor in the tissue including the diaphragm or tissue substantially close to it. However, in other embodiments, the electrical lead may be secured at least partially in the airway by anchoring means as described herein while the needle or probe pierces the airway wall and extends into the tissue. As described in reference to other embodiments, the electrical lead and sensor may be guided to the implantation site using imaging techniques, such as, but not limited to, fluoroscopy, computed tomography, magnetic resonance imaging, x-ray, ultrasound, position emission tomography, as are known. In some embodiments, the needle or probe tip may include one or more sensors for sensing parameters, such as, but not limited to, diaphragmatic contractility, diaphragmatic electrical activity, cardiac electrical activity, cardiac contractility, blood pressure, blood flow, cardiac motion, oxygen, and the like. A needle or probe tip may additionally, or alternatively, include an electrical stimulation electrode operable for providing electrical stimulation therapy as described herein. In one embodiment, the needle or probe tip for piercing the airway may have a relatively small diameter, such as approximately 0.05 mm to approximately 4 mm, and in some embodiments less than approximately 1.5 mm, to reduce the risks of pneumothorax, which may result from air or gas accumulating in the pleural cavity.

III. Method of Implanting a Pulse Generator in an Airway

In illustrative embodiments, the method of use of the stimulation systems described herein may include at least one electrode implantable within a patient's airway, for example the trachea, the primary, secondary, or tertiary bronchus, the bronchioles, or any branch thereof, and a pulse generator implanted within the trachea, the primary bronchus, or both. Various techniques may be performed to implant the electrode or the pulse generator within an airway. For example, techniques similar to those used to perform a bronchoscopy, laryngoscopy, tracheal intubation, or percutaneous catheterization may be performed to position and implant the electrodes or the pulse generator.

Figure 10:
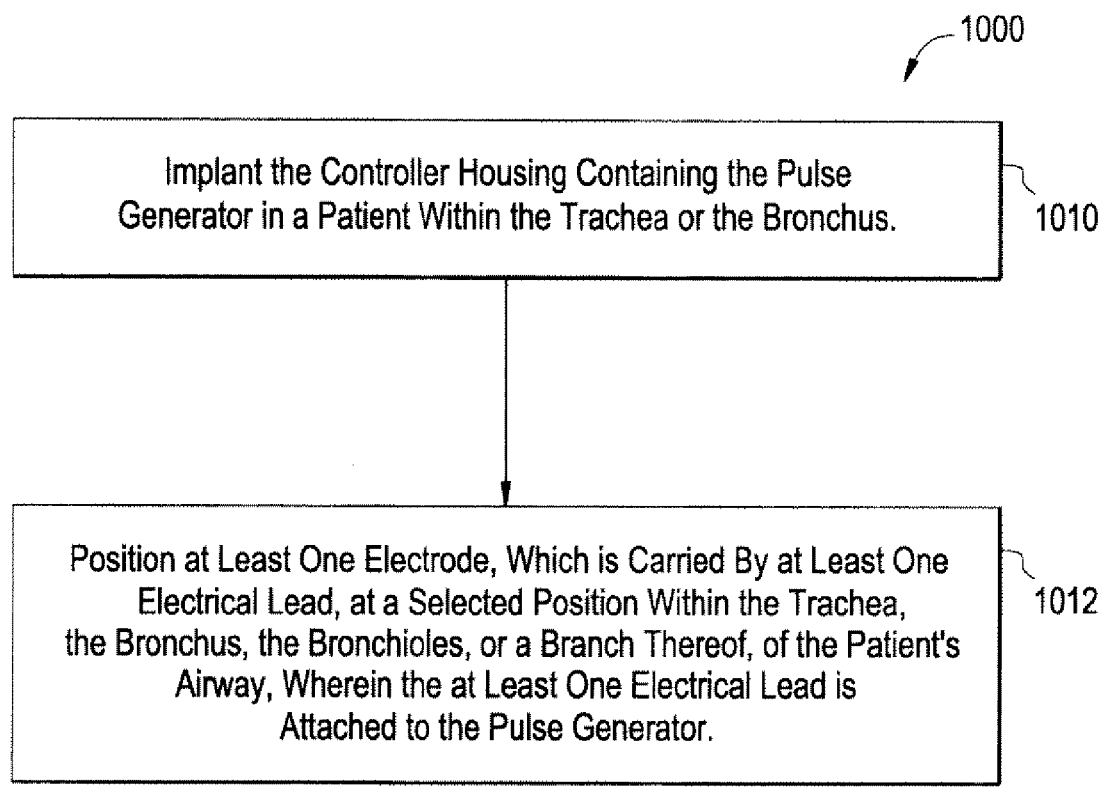
FIG. 10 is a flowchart of an illustrative method of implanting a diaphragm pacing device according to one embodiment of the invention.

FIG. 10 illustrates a method for implanting a diaphragmatic stimulation device according to one embodiment in which the controller housing is implanted within a patient's airway. Flowchart 1000 illustrates an example of a method for implanting a diaphragmatic device including a controller housing and pulse generator and at least one electrode carried by at least one electrical lead, such as those described herein with reference to FIGS. 2 and 9A-9D.

The method begins at block 1010. At block 1010, the controller housing containing the pulse generator is implanted in the patient within the trachea or a bronchus, such as the right or left primary bronchus. The controller housing may be inserted through the patient's oral or nasal cavity and deployed to the trachea or the right or left primary bronchus. In one embodiment, such as described herein with reference to FIG. 7, the controller housing may be positioned partially within the trachea and partially within one or both of the primary bronchi at the bronchial bifurcation. The controller housing may be any controller housing operable to perform electrical stimulation or sensing of diaphragmatic, pulmonary, or any other physiologic functions, such as those described herein with reference to FIGS. 3A-3F, 4, and 6A-6B. The controller housing may be implanted using procedures similar to those which may be used to deploy and position an electrode, as described herein, or procedures similar to those performed for tracheal intubation.

The controller housing is anchored within the airway to retain the housing at the selected position. The controller housing may further include one or more sensing or stimulation electrodes associated with the casing or the anchor device. Accordingly, anchoring may further serve to improve electrical coupling of any controller housing or anchor electrodes. The controller housing may be fixed within the airway by an anchor device, such as those described herein with reference to FIGS. 3A-3F.

Following block 1010 is block 1012, in which at least one electrode carried by at least one lead is positioned at a selected position (also referred to as an "implantation site") within the trachea, the primary, secondary, or tertiary bronchus, the bronchioles, or any branch thereof. The electrode may be inserted through the patient's oral or nasal cavity, and deployed through the trachea and bronchi to the selected implantation site. The electrode may be any suitable design, such as those described herein with reference to FIGS. 8A-8G.

The order of placement of electrodes within the bronchi for embodiments including more than one electrode may depend, at least in part, on factors such as each electrode's placement relative to one or more other electrodes or the criticality or immediacy of each electrode's purpose. A catheter, endoscope, or other elongated cannula suitable for deploying medical devices, may be used to delivering the electrical lead and electrode through the airway and to the selected implantation site. Any imaging technique known in the art, such as fluoroscopy, computed tomography, magnetic resonance imaging, x-ray, ultrasound, or position emission tomography may also be utilized to assist with delivering and positioning of the electrode.

Each electrode positioned within the airway may be fixed within the airway to retain the electrode at its selected position site and to improve electrical coupling. The electrode or electrodes may be fixed within the airway by an anchor device, such as those embodiments described herein with reference to FIGS. 8A-8G.

Each electrical lead carrying an electrode is attachable to the pulse generator to enable electrical communication therebetween. The electrical lead may be attached prior to implantation, during implantation, or after implantation of the electrodes and/or controller housing (e.g., the pulse generator). Furthermore, in one embodiment, the electrical lead may be permanently integrated within the controller housing, and thus permanently attached. The electrical lead or leads optionally may be fixed within the airway by a lead securing member, such as the embodiments described herein with reference to FIGS. 8H-8K.

The steps described herein need not be performed in the exact order as presented. For example, in some implantation methods, the controller housing may be positioned and anchored prior to the electrodes. In another example, the electrical leads may be attached to the controller housing prior to positioning and anchoring the controller housing, the electrodes, or both the controller housing and the electrodes.

Although FIG. 10 describes an illustrative method of implanting a pulse generator within the airway, the pulse generator may be implantable subcutaneously rather than within the airway as described herein, for example as described with reference to FIGS. 19-21.

Figure 11:
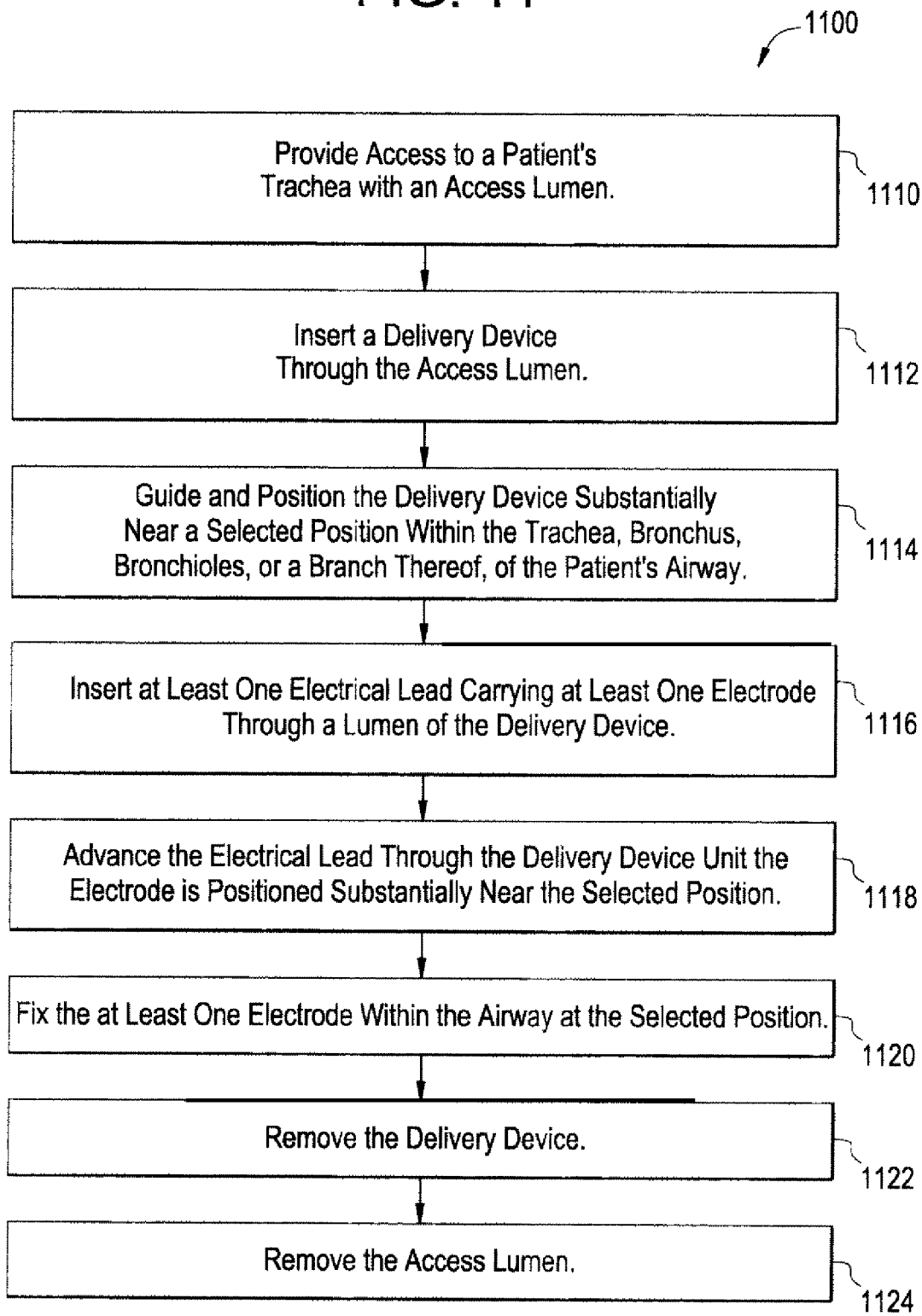
FIG. 11 is a flowchart of an illustrative method of implanting an electrode according to one embodiment of the invention.

FIG. 11 illustrates a flowchart 1100 describing one method for implanting at least one electrode of an implantable diaphragmatic stimulation system within the airway of a patient, for example the trachea, the primary, secondary, or tertiary bronchus, the bronchioles, or any branch thereof, according to certain embodiments, such as those described herein with reference to FIGS. 2, 8A-8K, and 9A-9D.

The method begins at block 1110. At block 1110, access is provided to a patient's trachea for subsequent insertion of one or more delivery devices and one or more electrical leads each carrying at least one electrode or other sensor. Access may be provided by inserting an access catheter, for example, an endotracheal tube, such as those used when intubating a patient, or an endoscope, such as those used when performing bronchoscopies or laryngoscopies. Accordingly, the access catheter may be inserted orally or nasally. This method may be performed while the patient is under general anesthesia, regional anesthesia, local anesthesia, or while the patient is anaesthetized.

Block 1112 follows block 1110, in which a delivery device may be inserted through the access catheter. The delivery device may be any device suitable for aiding with access by a medical device into a lumen of the body, for example, a catheter, guidewire, or combination thereof. Illustrative catheters that may be used include, but are not limited to, a torque catheter, a steerable catheter, a pre-shaped catheter varying by application, a deflectable catheter, or a catheter and guidewire combination. The delivery device may be a series of catheter systems, by which a first catheter aids in the placement of a second catheter that carries the electrical lead and electrode, for example. Depending upon the implantation site, example catheter diameters suitable for delivery range from approximately 1 mm to approximately 14 mm; though, the catheter diameter depends upon its intended use. For example, a catheter having a diameter of about 1 mm to about 5 mm is useful for gaining access to and navigating smaller lumens, such as for deploying an electrical lead. As another example, a catheter having a diameter of about 1 mm to about 7 mm is useful for navigating using a bronchoscope or other imaging device. As another example, a catheter having a diameter of about 4 mm to about 14 mm is useful for the deployment of a tracheal device, such as an implantable pulse generator. The diameter of the catheter or other delivery device typically depends upon many factors, including, but not limited to, the size of the implantation site, the size of the patient, the configuration of the device being deployed, and the expected duration of the within the lumen.

Following block 1112 is block 1114, in which the delivery device is guided to and positioned substantially near the selected position for implantation. As described herein, the selected implantation site may be at any path within the patient's airway, such as the trachea, primary, secondary, or tertiary bronchus, or the bronchioles. In illustrative embodiments, the selected implantation site for performing electrical stimulation may not be the desired site for performing sensing. In this situation, a compromise implantation site may be selected, the site correlating to the most important function (e.g., the selected stimulation site) may be selected, or separate stimulation and sensing electrodes may be implanted. As described herein, the two electrodes may be carried by the same electrical lead or may be carried by individual electrical leads.

Figure 23:
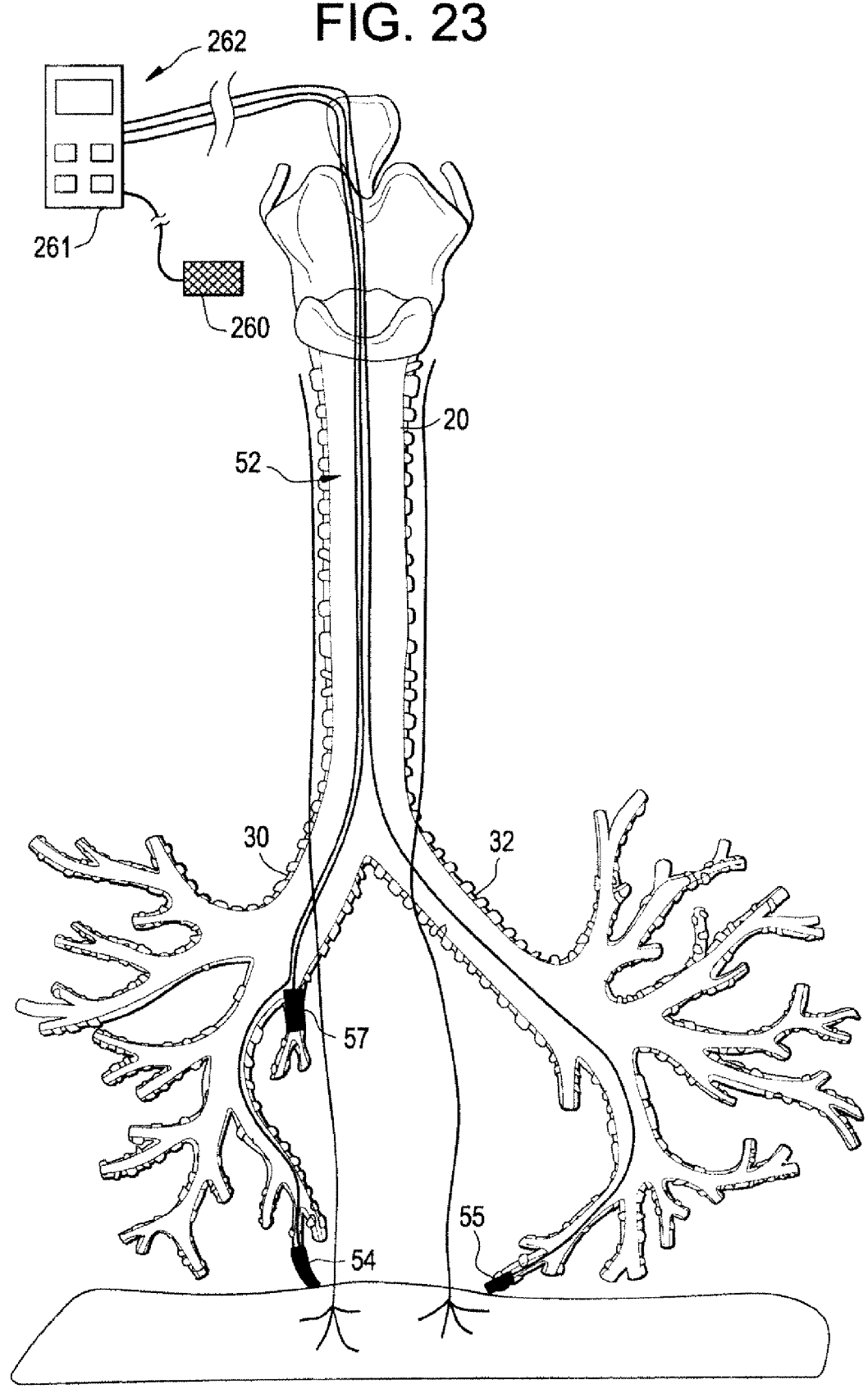
FIG. 23 is a diagram of illustrative diaphragm pacing device placement according to one embodiment of the invention.

In one embodiment, as further described by example with reference to FIG. 23, the electrode implantation sites include at least one electrode site in operable proximity to the diaphragm or the patient's phrenic nerve. For example, in one embodiment, one electrode is positioned in a distal location of the patient's tertiary bronchi proximal the diaphragm. In another embodiment, two electrodes are placed in the patient's tertiary bronchi, each located near a different hemisphere of the diaphragm. In yet another embodiment, an electrode may be positioned at any position within the airway that is proximal one of the patient's phrenic nerves, to permit stimulating the diaphragm via stimulation of the phrenic nerve. It is appreciated that any combination of these electrode positions, or any other described or referenced herein, may be used in various embodiments. Moreover, as further described herein, such as with reference to FIG. 23, one or more reference electrodes may be implanted within the patient's airway, or within or on any other portions of the patient's body (e.g., within the patient's GI tract, subcutaneously, or externally placed electrodes attached to the patient's skin).

One or more imaging techniques may be used to assist guiding the delivery device to the implantation site. Representative examples of suitable imaging techniques include, but are not limited to, bronchoscopy, bronchography, fluoroscopy, computed tomography, magnetic resonance imaging, x-ray, ultrasound, or position emission tomography. The delivery device optionally may include a radiopaque coating or a radiopaque component, as known in the art, to increase visibility and aid in deployment using certain imaging techniques. Other navigation techniques may also be used to aid in deployment. One technique may include the deployment technology developed by superDimension, Ltd. (Herzelia, Israel) known as the in Reach System™, which includes a catheter with a magnetic tracking device calibrated with a computed tomography scan of the patient, allowing for the computed tomography data to assist in guiding the catheter to the implantation site. Another example of a guiding technique may include the location technique developed by MediGuide, Ltd. (Haifa, Israel) known as the Medical Positioning System™, which includes a catheter or other delivery device having a miniaturized sensor and enables three-dimensional tracking of the device's position. Yet another example of a guiding technique may include a mapping electrode within the delivery device, such that the mapping electrode may be used to aid in selection of the implantation site. For example, electrical coupling of an electrode, electrical impedance over a wide range of frequencies, and electrical coupling at multiple positions within the airway may be mapped to identify optimal implantation sites. In one embodiment, one of the electrodes intended to be used for ultimate stimulation and/or sensing may also be used as the mapping electrode, leaving the electrode in place. In another embodiment, an additional mapping electrode may be used with the delivery device and removed prior to positioning and fixing the system electrode or electrodes. For example, a mapping electrode or other sensor may detect one or more intrinsic signals generated by the heart, such as electrical activity or acoustic signals. The mapping electrode may be integrated with the implantable electrical lead or with the delivery device. Additional guiding techniques can be utilized, such as measuring the electrical threshold for stimulating the targeted nerve, the diaphragm, or a specific portion thereof. For embodiments that measure the electrical threshold, an algorithm may determine the stimulation gradient, for example, by calculating the derivative of the measured threshold along its path.

Block 1116 follows block 1114, in which the electrical lead carrying the one or more electrodes is inserted through the delivery device after the delivery device has been positioned at or near the desired implantation site. As previously described, the delivery device may have a lumen through which the electrical lead may be inserted, such as a catheter, or the delivery device may be integrated with the electrical lead and electrode, such that deployment and positioning of the delivery device also deploys the electrical lead and electrode. For example, according to one embodiment, a delivery device includes a first catheter deployed through the airway to the implantation site, and a second catheter housing the electrical lead and electrode therein, which is deployed through the first catheter. Accordingly, in some embodiments, the delivery device may be integrated with the electrical lead and electrode, and all or some of the steps described at blocks 1114-1118 may be performed concurrently.

At block 1118, following block 1116, the electrical lead is advanced through the delivery device to or substantially near the selected implantation site. As described with reference to insertion/positioning of the delivery device, the method optionally may include imaging techniques or other guiding technologies to assist in deployment of the lead to identify the location of the electrode and its proximity to the selected implantation position.

Block 1120 follows block 1118, in which the electrode may optionally be anchored within the airway lumen at the selected implantation position. Any of the described anchor devices may be used to assist anchoring and retaining the electrode at or near the implantation site, such as those described with reference to FIGS. 8A-8G. For example, an electrode embodiment as described with reference to FIGS. 8E and 8F deployed through a catheter or other cannula will have the two or more electrode sub-components compressed within the catheter and the expandable connector under tension during delivery through the delivery device. Upon positioning the electrode at or near the implantation site, the delivery device is removed, which releases the tension on the expandable connector and causes the electrode sub-components to expand radially in contact with the inner walls of the airway at the selected implantation site. In other electrode embodiments, the anchor devices may require additional action, such as, but not limited to, mechanically extending rigid radially extensible members, inflating a balloon or a balloon sleeve, applying heat, radio frequency, electrical, or other energy to change a shape memory alloy-based anchor device, suturing, or stapling, for example. In yet other embodiments, the electrode anchor device may anchor without additional action, such as anchor devices configured as hooks, barbs, studs, or adhesive, or anchor devices having a diameter the same as or slightly larger than the inner wall of the airway that lodge within the airway. Optionally, one or more lead securing members may be used to assist retaining the electrical lead within the airway, such as is described with reference to FIGS. 8H-8K.

Blocks 1122 and 1124 follow block 1120, in which the delivery device and the access catheter are removed upon positioning and fixing the electrode or electrodes. However, in some embodiments, the access catheter and/or the delivery device may be used during implantation of the controller housing (if not implanted prior), and the removal steps occurring at blocks 1122 and 1124 may occur subsequent to deployment and implantation of the controller housing.

As described herein, the electrical leads may be attached to the controller housing prior to deployment of the electrical leads, or they may be free from the controller housing and attached subsequent to deployment of the electrical leads either before or after deployment of the controller housing. Accordingly, in some embodiments, upon removing the delivery device and the access catheter, the electrical leads temporarily extend out of the patient's oral or nasal cavity until subsequent attachment to and implantation of the controller housing. Though, in some embodiments, the electrical leads are retained entirely within the patient's airway, such as when the controller housing is implanted prior to the electrical leads or otherwise.

In yet other embodiments, as described with reference to FIGS. 25A-25B, the electrode or electrodes are wireless electrodes in wireless communication with a pulse generator, and do not require electrical leads. However, the methods described with reference to FIG. 11 may also be used to deploy and position a wireless electrode.

Figure 12:
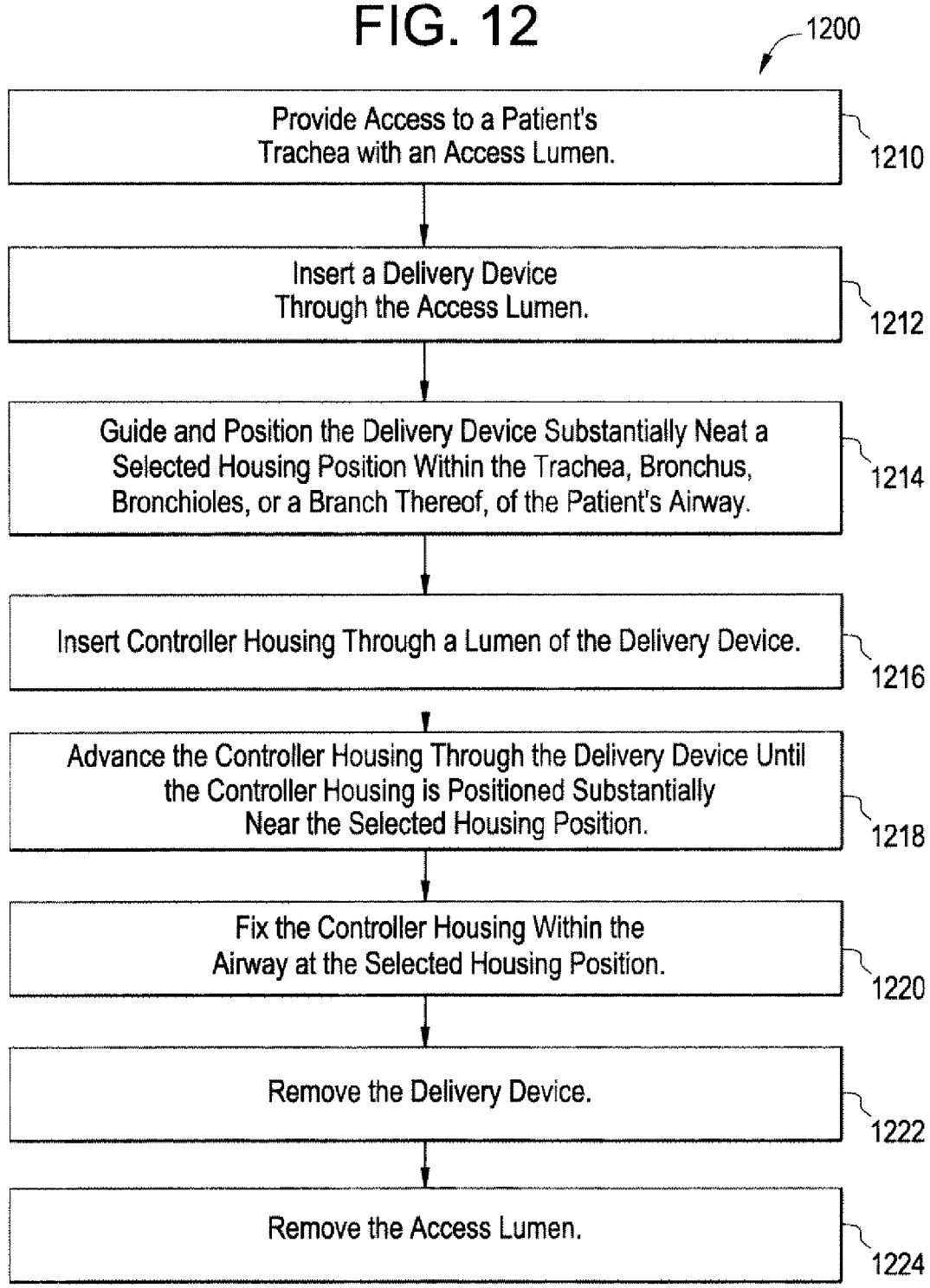
FIG. 12 is a flowchart of an illustrative method of implanting a controller housing according to one embodiment of the invention.

FIG. 12 illustrates a flowchart 1200 describing one method for implanting a controller housing containing a pulse generator of a diaphragmatic (or nerve) stimulation device, within the airway of a patient, for example the trachea or the left or right primary bronchus, such as described herein with reference to FIGS. 2, 3A-3F, and 9A-9D. This method may include steps similar to those described with reference to FIG. 11 for implanting one or more electrodes.

The illustrative method begins at block 1210. At block 1210 access is provided to a patient's trachea for subsequent insertion of one or more delivery devices and the controller housing. Access may be provided by inserting an access catheter, for example, an endotracheal tube, such as those used when intubating a patient, an endoscope, such as those used when performing bronchoscopies or laryngoscopies. Moreover, the access catheter may be inserted orally or nasally. This illustrative method may be performed while the patient is under general anesthesia, regional anesthesia, local anesthesia, or performed without anesthesia.

Block 1212 follows block 1210, in which a delivery device may be inserted through the access catheter. The delivery device may be any device suitable for providing access of a medical device into a lumen of the body, such as those described with reference to FIG. 11. In one embodiment of the method, the delivery device may be a series of catheter systems, by which a first catheter aids in the placement of a second catheter that may carry the controller housing, for example. In another embodiment, however, the delivery device may include a guidewire or other supporting device first inserted through the access catheter and a second catheter or other device carrying the controller housing that slides over the guidewire. In yet another embodiment, the delivery device may be a single catheter carrying the controller housing directly to the implantation site without the use of a guidewire or additional catheter. This embodiment may best be used when the implantation site is within the patient's trachea because the site is relatively close to the patient's oral or nasal cavity, larger in diameter, and may be visible during implantation.

Following block 1212 is block 1214, in which the delivery device is guided to and positioned substantially near the desired implantation site. The implantation site may be at any point within the patient's airway, such as the trachea or the right or left primary bronchus. In one embodiment, in which the pulse generator includes one or more electrodes on the housing or anchor device, the electrode may optionally be used to identify desired implantation site based at least in part on stimulation or sensing functioning as described above. Furthermore, one or more imaging techniques, for example those described with reference to FIG. 11, may optionally be used to assist guiding the delivery device to the implantation site.

Block 1216 follows block 1214, in which the controller housing is inserted through the delivery device after the delivery device has been positioned at or near the desired implantation site. The delivery device may have a lumen through which the controller housing may be inserted, such as a catheter. The controller housing may be integrated with the delivery device at the outset, such that deployment and positioning of the delivery device also deploys the controller housing. Accordingly, for embodiments in which the controller housing is integrated with the delivery device, all or some of the steps described at blocks 1214-1218 may be performed concurrently.

At block 1218, following block 1216, the controller housing may be advanced through, over, or with the delivery device to or substantially near the selected implantation site. As described with reference to deployment of the delivery device, some embodiments optionally include imaging techniques or other guiding technologies to assist in deployment of the lead to identify the location of the controller housing and its proximity to the selected implantation position.

Block 1220 follows block 1218, in which the controller housing is fixed within the airway lumen at the selected implantation position. Any of the anchor devices described herein may be used to assist fixing and retaining the controller housing at or near the implantation site, such as those described with reference to FIGS. 3A-3F or those described with reference to FIG. 11 for implanting an electrode.

Blocks 1222 and 1224 follow block 1220, in which the delivery device and the access catheter are removed upon positioning and anchoring of the controller housing. In some embodiments, however, the access catheter and/or the delivery device are used during implantation of the electrical lead and electrode (if not implanted prior), and the removal steps occurring at blocks 1222 and 1224 may occur subsequent to deployment and implantation of the electrodes.

Figure 13:
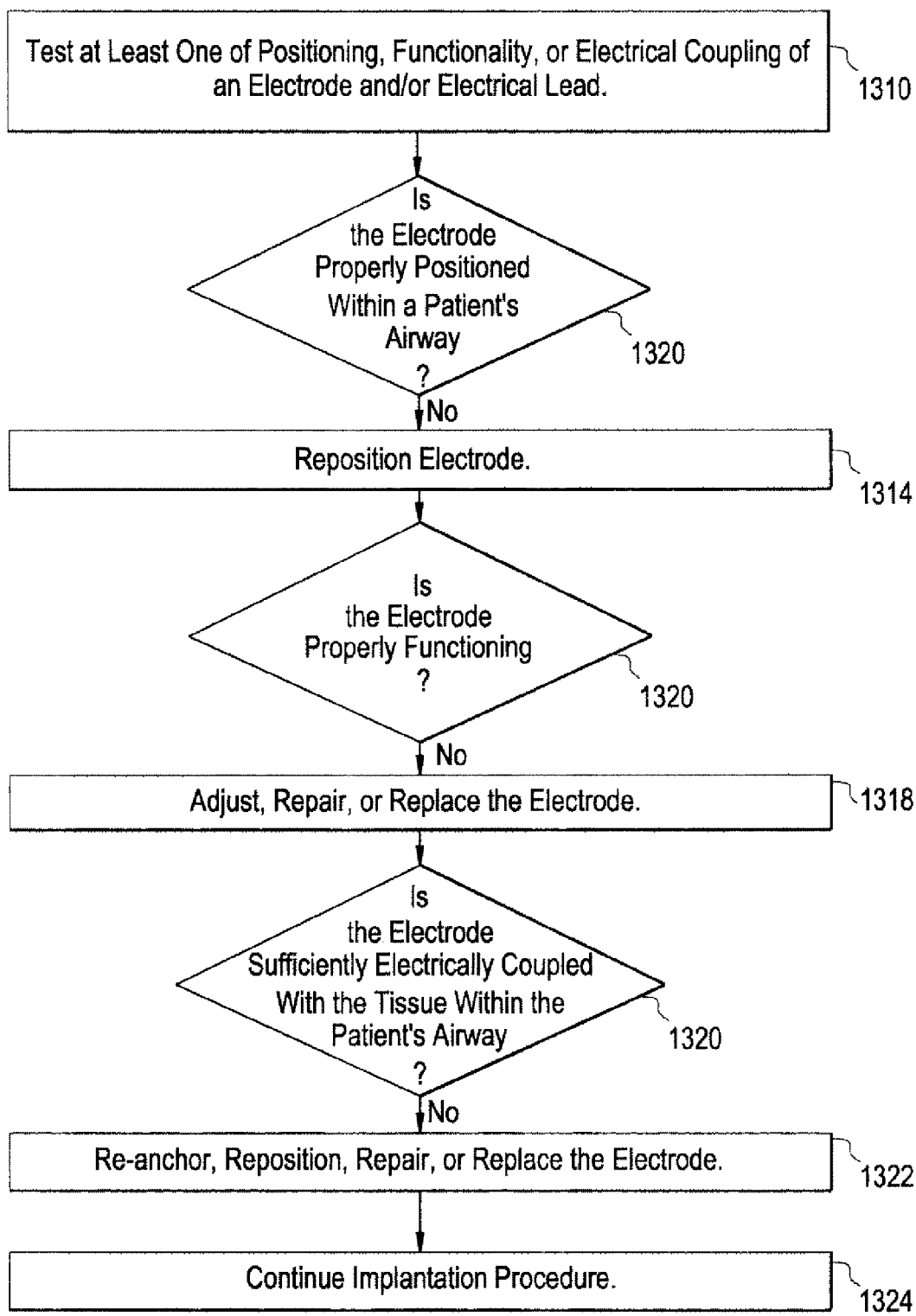
FIG. 13 is a flowchart of an illustrative method of testing an implanted electrode according to one embodiment of the invention.

Upon positioning and implanting at least one or more electrodes within the patient's airway, the functionality, position, and/or electrical coupling of each electrode may be tested. FIG. 13 illustrates a flowchart 1300 describing one method for testing at least one of the positioning, functionality, or electrical coupling of each electrode subsequent to implantation.

The method begins at block 1310. At block 1310, the electrode testing procedures for testing at least one of the positioning of the electrode, the functionality of the electrode, or the electrical coupling of the electrode begin subsequent to implanting the electrode within a patient's airway. This step may include attaching the proximal end of the electrical lead carrying the implanted electrode to external testing electrical circuitry, software, and/or hardware. In other embodiments, the electrical lead is attached to the controller housing prior to its implantation and the pulse generator is used at least partially during the testing procedures. While the flowchart 1300 illustrates performing the testing procedures subsequent to implantation of each electrode, the testing procedures may be performed after all electrodes have been implanted, after the controller housing has been implanted, or at any other suitable stage in the implantation methods subsequent to implanting the electrode being tested.

One or more of the decision blocks 1312, 1316, and 1320 follow block 1310, in which at least one of the results of the positioning, functioning, or electrical coupling testing is queried. Each of the steps described at blocks 1312, 1316, or 1320 are not required to be performed, and various methods of use may perform only a subset of the testing and determination procedures.

At decision block 1312, it is determined whether the electrode is properly positioned. This determination may be performed using any of the imaging techniques, guiding techniques, or electrical signal monitoring described herein. If it is determined that the electrode is not positioned properly, then block 1314 follows, in which the electrode is repositioned according to any of the electrode placement methods described herein, such as those described with reference to FIG. 11. Alternatively, if it is determined that the electrode is positioned properly, then block 1316 follows.

At decision block 1316, it is determined whether the electrode is properly functioning. This determination may be performed using externally located testing circuitry, electronic controllers, software, hardware, and the like, as is suitable for performing electrode testing. Electrode functions, such as conductivity, electrical stimulation functioning, or sensing functioning, may be tested by this procedure. For example, whether the electrode stimulation is within a predefined acceptable range, or whether the electrode stimulation threshold is stable can be tested at block 1316. Safe operation may be tested at this stage as well. If it is determined that the electrode is not functioning properly, then block 1318 follows, in which the electrode may be adjusted, repaired, or replaced. Alternatively, if it is determined that the electrode is functioning properly, then block 1320 follows.

At decision block 1320, it is determined whether the electrode is sufficiently electrically coupled with the tissue at the selected implantation site. Similar to testing the functionality, external hardware, software, and/or the pulse generator may be used to perform the electrical coupling testing. In one example, the electrical impedance is measured between the implanted electrode and another electrode operating as a reference electrode, and using electronic circuitry, such as a resistance-capacitance-inductance meter, as known in the art. If it is determined that the electrode is not properly coupled, then block 1322 follows, in which the electrode may be re-anchored, repositioned, repaired, or replaced. Alternatively, if it is determined that the electrode is coupling properly, then block 1324 follows.

At block 1324 the testing procedures are completed and subsequent implantation steps may be performed as necessary, such as implanting additional electrodes, the controller housing, or attaching the electrical leads to the housing, as is described herein with reference to FIGS. 10-12, for example.

As illustrated by FIG. 13, a testing method may be performed subsequent to implantation of each electrode. The method may be performed prior to attaching the electrical leads to the controller housing, and be tested using external testing circuitry and hardware. In another example, the method may be performed subsequent to attaching the electrical leads to the controller housing, either prior to or subsequent to implanting the controller, and may at least partially use the pulse generator to perform the testing. In other example testing methods, the testing may be performed only after all of the electrodes are implanted.

Figure 14:
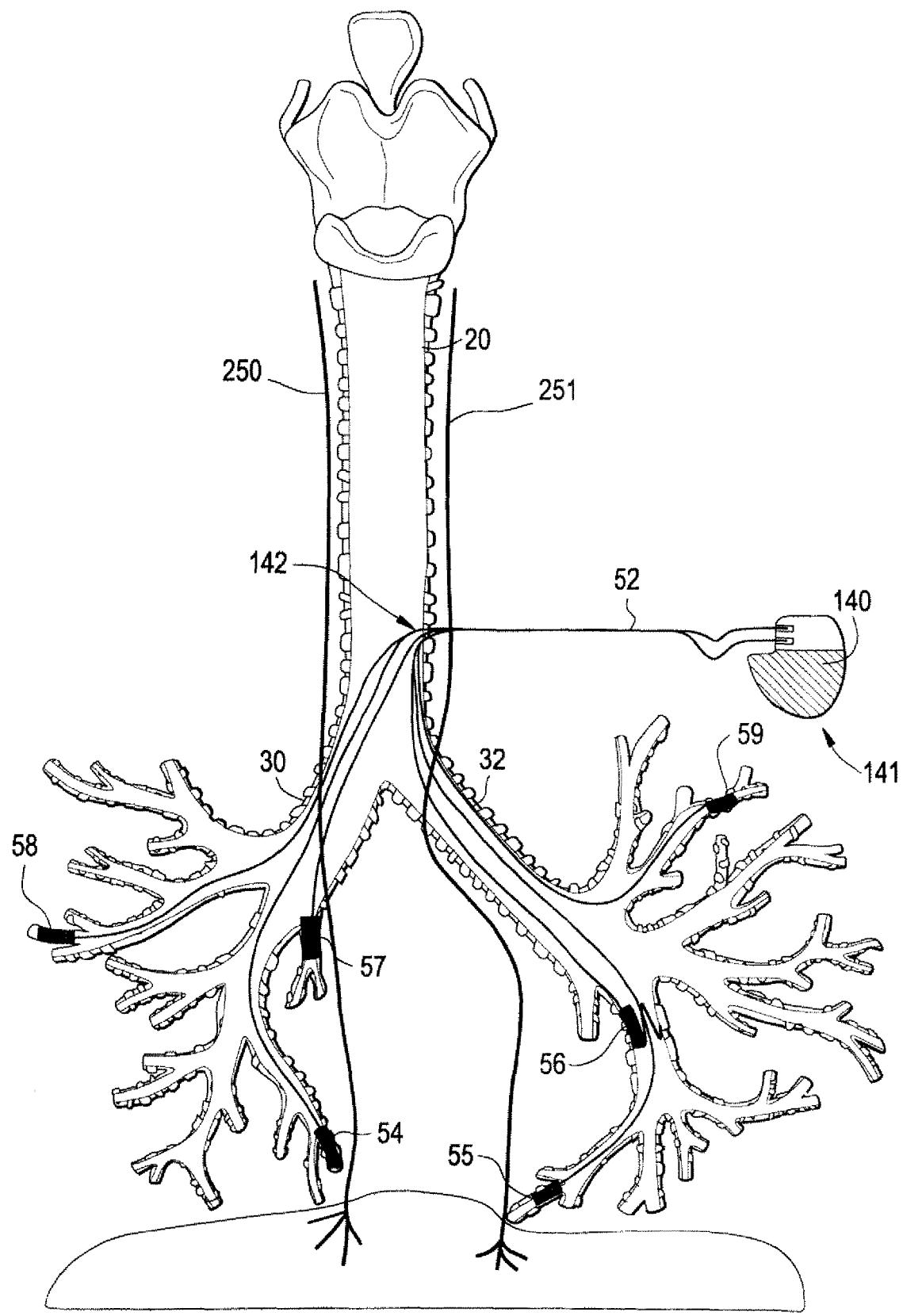
FIG. 14 is a diagram of an illustrative diaphragmatic device placement according to one embodiment of the invention.

IV. Implantable Electrodes and Electrical Leads Attachable to a Pulse Generator Implantable Subcutaneously In another embodiment, a controller housing including a pulse generator may be implantable at a subcutaneous location within the patient, and at least one electrical lead carrying at least one electrode fixable within the trachea or bronchi, may pass through, or communicate wirelessly at, an area of the patient's trachea or a primary bronchus. FIG. 14 illustrates one embodiment of an implantable diaphragmatic stimulation system having a controller housing 140 including a pulse generator 141 implantable subcutaneously and at least one electrode implantable within the bronchi. Thus, the diaphragmatic device of this embodiment minimizes the components implanted within the airway, but does require an invasive surgical procedure for implantation of the controller housing 140. For example, the controller housing 140 may be surgically implanted approximately in a patient's pectoral region and a subcutaneous tunnel formed from the controller housing 140 to the patient's trachea or primary bronchus. In other variations of this embodiment, another subcutaneous location may be selected as the implantation site for the controller housing.

The pulse generator 141 of this embodiment may be operable to perform some or all of the same functions described herein, such as those with reference to FIG. 2 describing a pulse generator implanted within an airway. For example, the pulse generator 141 may perform electrical stimulation through the one or more attachable electrical leads and electrodes, such as is used to perform diaphragmatic pacing, phrenic nerve stimulation, diaphragm stimulation for controlling the intra-abdominal pressure for helping to expel vomit, feces, and urine from the body, or for controlling the pressure on the esophagus as it passes through the esophageal hiatus for preventing acid reflux. The pulse generator 141 may be operable to sense or measure diaphragmatic electrical activity, other diaphragmatic activity, breathing, lung movement and/or other physiological parameters.

As used with this embodiment, the pulse generator 141 may be a conventional implantable pulse generator suitable for subcutaneous implantation, as is commercially available, which may also commonly be referred to as an "implantable pulse generator" or "IPG." However, the electrical circuitry, software, and hardware of the pulse generator 141 may be altered or adapted for operation with electrodes implantable within the airway, in contrast to conventional implantable pulse generators used with electrodes in direct contact with the phrenic nerve or the thoracic diaphragm. The controller housing 140 may be proportioned to have a substantially flat shape to ease placement subcutaneously and avoid discomfort to the patient. The controller housing 140 may be hermetically sealed, electrically isolated, and biocompatible in order to operate safely and to withstand the biological environment within which it may be implanted.

The pulse generator 141 is electrically coupled to at least one electrical lead 52, carrying at least one electrode. The electrode or electrodes may be positioned at or near the distal end of the electrical leads 52, as illustrated in FIG. 14. However, in other embodiments, an electrode may be positioned at another point distanced from the lead's distal end. The device of FIG. 14 is illustrated as including six electrodes 54, 55, 56, 57, 58, 59 implantable within the bronchi, each connected to a different electrical lead 52, in a similar manner as is described with reference to FIG. 2, to show various example electrode implantation sites. It is appreciated, however, that according to some embodiments, fewer electrodes may be implanted, such as one or two electrodes implanted in operable proximity to the patient's diaphragm, and/or one or more electrodes in operable proximity to the patient's phrenic nerve(s), which may be used to perform diaphragmatic stimulation. In another embodiment, the pulse generator 141 may be operated in combination with one or more airway implanted electrodes and with one or more conventionally implanted electrodes, such as phrenic nerve cuff electrodes or conventional diaphragm electrodes.

A subcutaneous tunnel, through which the one or more electrical leads 52 may pass, is surgically formed between the controller housing 140 implantation site, for example near the pectoral region, and a junction 142 at the trachea or the left or right bronchus. As illustrated, the electrical lead or leads 52 pass through one or more apertures formed in the trachea 20 or the left or right primary bronchus 30, 32 at the junction 142 and into one or more locations within the airway. Alternatively, rather than passing through an aperture, the electrical lead may communicate wirelessly across the junction 142. In the embodiment illustrated in FIG. 14, a single lead 52 is coupled to the pulse generator 141 and splits into multiple leads carrying each electrode 54, 55, 56, 57, 58, 59 to respective selected implantation positions within the airway. In other embodiments, however, each electrode may be carried by individual leads, which may be optionally bundled to ease the passage through an aperture, or simplify wireless communication, at the junction 142. The electrical leads 52 used in these embodiments may be substantially similar to other electrical leads described herein. The embodiment in FIG. 14 is provided for illustrative purposes, and other electrode and controller housing positioning and configurations are envisioned. For example, the electrodes may be positioned at any selected electrode position, as illustrated in FIGS. 9A-9D.

Cannula

In one embodiment, the trachea or the left or right primary bronchus may be penetrated and one or more apertures may be formed therethrough for passing at least one electrical lead carrying at least one electrode from the subcutaneously implanted controller housing and into the bronchi. In one embodiment including multiple implantable electrical leads, an aperture for each electrical lead may be formed in the trachea or the left or right primary bronchus, to reduce the aperture sizes and to reduce the friction caused within each aperture to minimize stresses caused on the electrical lead or on the airway wall. A cannula may optionally be implanted in the wall of the trachea or bronchus to aid in sealing the thoracic cavity from the airway, exclude the passage of air, biological contaminants, or biological fluids therebetween, provide structural integrity to the aperture in the airway wall, house the electrical leads to ease movement therethrough, and reduce irritation, inflammation, or infection where the electrical leads may otherwise contact the trachea or bronchus wall. In some embodiments, however, the cannula may not be implanted in the trachea or bronchus wall, but may be affixed to the inner or exterior wall of the trachea or bronchus and around the aperture formed therein. The cannula may be formed in any shape suitable to be implanted in the trachea or bronchus and to permit one or more electrical leads to pass therethrough, such as, but not limited to, tubular, sleeve-like, disk-like, or elliptical, for example. The cannula may be constructed from any biocompatible materials suitable for subcutaneous implantation and to provide at least partial rigidity and structural support in the passage, such as metals, polymers, or any combination thereof. Furthermore, in an embodiment having multiple apertures formed in the airway wall, multiple cannulae may be dimensioned to position an individual cannula in each aperture.

Figure 15A:
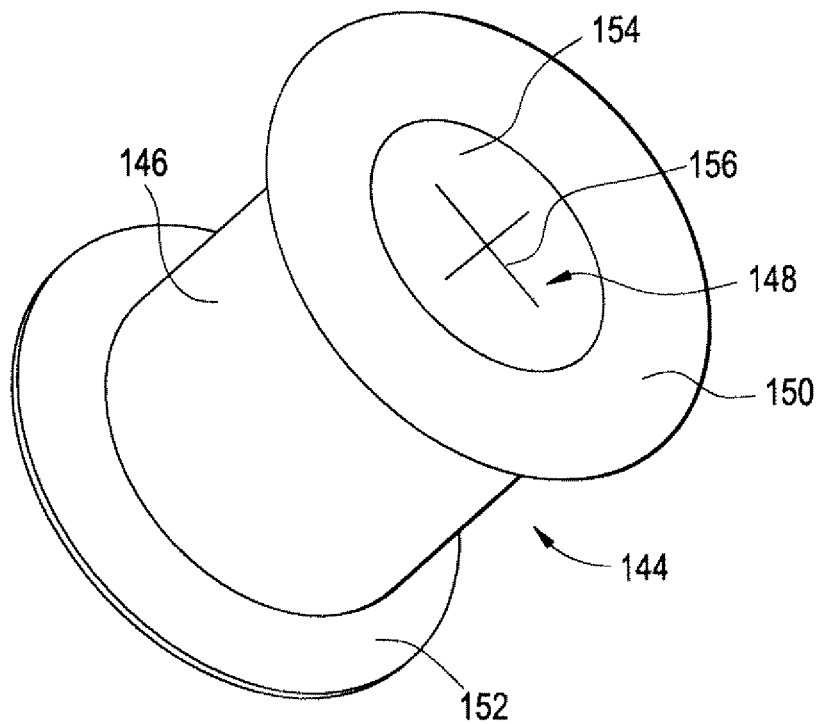
FIG. 15 is a diagram of an illustrative cannula according to one embodiment of the invention.

FIG. 15A illustrates one representative example of a cannula useful with the systems and methods described herein. The cannula 144 is formed as a sleeve or conduit, having an outer surface 146 and an inner surface (not shown) existing within the cannula 144, and defining an orifice 148 extending therethrough. In one embodiment, the inner diameter of the cannula 144 ranges from about 1 mm to about 4 mm, to allow for passing one or more electrodes therethrough. In another embodiment, the cannula 144 may have multiple orifices for passing individual leads therethrough, such that each individual orifice may have a diameter of about 1 mm to about 4 mm. In one embodiment, the length of the cannula 144 ranges from approximately 0.5 mm to about 3 mm, which may generally depend upon the configuration of the cannula 144 and the actual trachea or bronchus wall thickness, although the cannula 144 dimensions may depend upon the size of the passage, which ultimately depends, for example, upon its position, the size of the patient, or the number of electrical leads to pass therethrough. The cannula 144 may optionally include a first flange 150 and a second flange 152 extending radially from opposite ends of the cannula. The first and second flanges 150, 152 are positionable against the inner wall and the outer wall of the airway to aid in retaining the cannula 144 implanted in the passage and to aid in sealing the thoracic cavity from the airway environment. The first and second flanges 150, 152 may further have a preformed curvature approximating that of the curved surfaces of the inner trachea and outer trachea, respectively, to aid in sealing, retention, and/or comfort.

In various embodiments, the cannula 144 further includes an inner membrane 154 extending between at least one of the flanges 150, 152 and across the orifice 148, having one or more slots or apertures 156 formed therethrough. The aperture 156 is dimensioned to have approximately the same or slightly smaller diameter as the electrical lead or leads intended to pass therethrough, such that the aperture 156 forms at least a partial seal around the electrical lead or leads. The inner membrane 154 allows passage of the electrical leads and provides further isolation between the environments. The inner membrane 154 may be formed from any biocompatible elastomeric material suitable for subcutaneous implantation, such as an elastomeric polymer, for example. Though not shown, two inner membranes 154 may be included, one on each end of the cannula and extending between each flange 150, 152.

Cannula 144 may be formed from pliable materials, for example, elastomeric polymers, such as silicone or polyurethane, such that they may be at least partially compressed within a lumen of a delivery device, such as a catheter or other cannula. When properly positioned and upon release from the delivery device, a pliable cannula 144 expands into place in the passage formed in the trachea or bronchus and each of the flanges 150, 152 expands radially inside and outside the airway, respectively. Various other cannula designs and shapes are envisioned, and any cannula suitable for the functions described herein may be used.

Figure 15B:
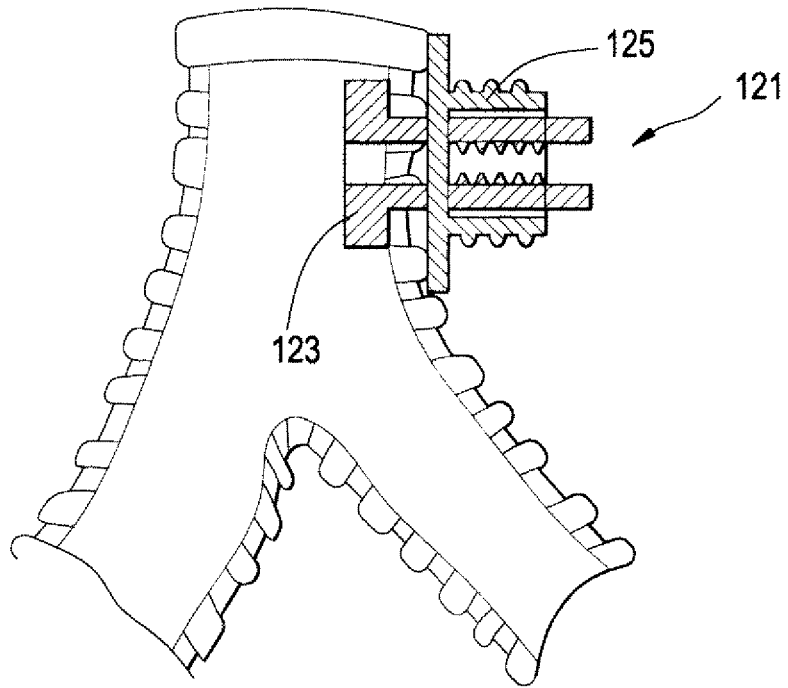

FIG. 15B illustrates another embodiment of a cannula useful in the systems and methods described herein. The cannula 121 may be configured in a manner similar to that illustrated by FIG. 15A but including two interconnecting sleeves (or interconnecting flanges), an inner sleeve 123 adapted for implantation in the trachea or bronchus from the interior and an exterior sleeve 125 adapted for implantation from the exterior of the trachea or bronchus. In one example, the inner sleeve 123 has an exterior diameter substantially the same or slightly smaller than the inner diameter of the exterior sleeve 125 to allow for slideably connecting them. Each of the inner sleeve 123 and exterior sleeve 125 has flanges extending radially therefrom, one or more orifices extending therethrough, and/or one or more membranes or sealing rings, as described with reference to FIG. 15A. Slideably connectable sleeves 123, 125 forming a cannula adjustably compensate for trachea or bronchus wall thickness, thus improving the seal formed by the cannula 121. A cannula 121 configured in this manner may be implanted in the aperture using techniques similar to those described herein with reference to FIGS. 16A-16C or 17A-17B.

Figure 16A:
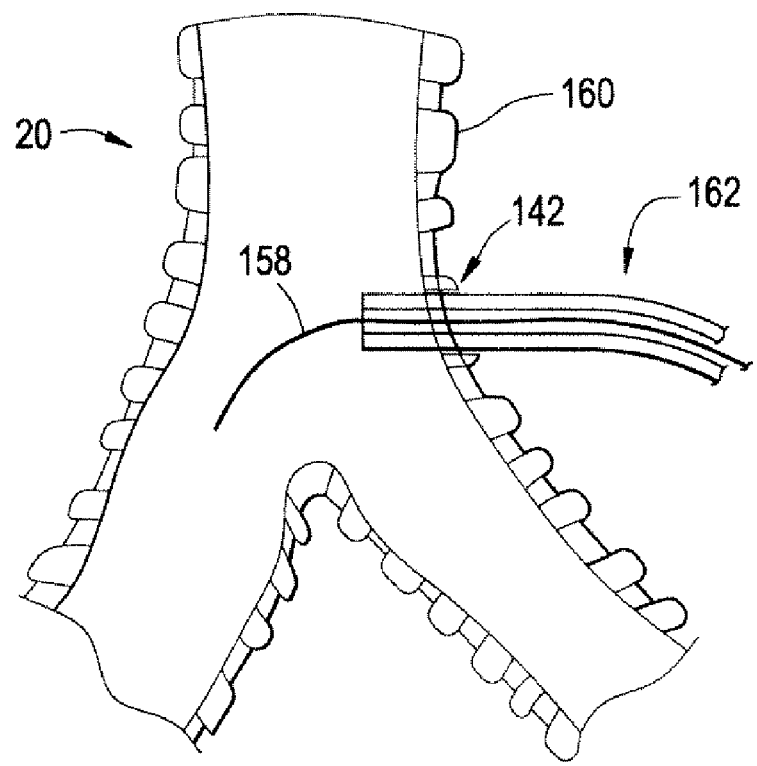
FIGS. 16A-16C are diagrams of an illustrative cannula implantable within a trachea or bronchus according to one embodiment of the invention.
Figure 16B:
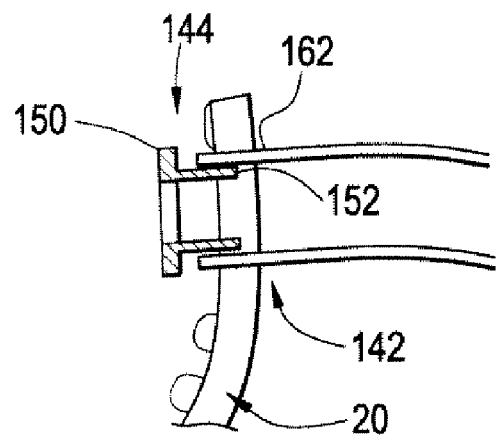
Figure 16C:
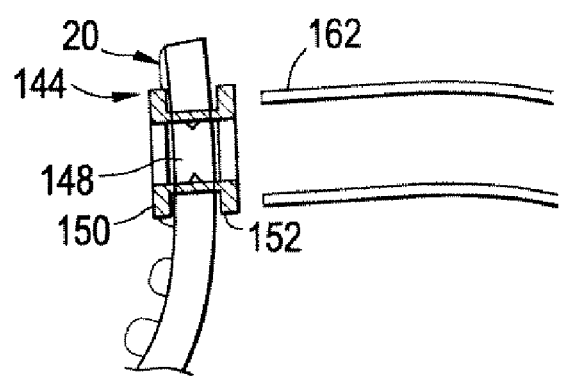

FIGS. 16A-16C illustrate a cross section of one embodiment of cannula 144 that may optionally be implanted within the wall of the trachea or primary bronchus at a junction 142, and represent illustrative stages in one method for implanting the cannula 144. FIG. 16A illustrates an initial stage during the implantation of the cannula 144 within the airway. The cannula 144 may be implanted during, or subsequent to, forming an aperture or passage in the trachea 20, such as by using a tunneling device, needle, or wire 158. In some embodiments, the aperture is formed with the tunneling device 158 through the wall and between the cartilage rings 160 of the trachea 20. If necessary or desired, the diameter of the aperture may be increased using a fenestrator, catheter tip, blade, tunneling device 158, or other suitable device for forming and/or opening an aperture in a human lumen. Subsequent to opening the aperture to the desired size, a cannula delivery device 162, such as a catheter or other elongated cannula for delivery, is inserted through the aperture and advanced into the airway of the trachea 20. The catheter may be inserted through the aperture over the tunneling device 158, or the tunneling device 158 may be removed prior to insertion of the cannula delivery device 162.

FIG. 16B illustrates a cross section of the cannula 144 during another stage of the implantation method. In this embodiment, the cannula 144 is formed from pliable materials and compressed within the delivery device 162 for delivery to the trachea 20. FIG. 16B illustrates the cannula 144 partially disposed within the distal tip of the delivery device 162 and partially released such that the first flange 150 is expanded radially within the airway of the trachea 20 and the second flange 152 remains compressed within the delivery device 162.

FIG. 16C illustrates a cross section of the cannula 144 implanted in the trachea 20 wall after removing the delivery device 162. Properly implanted, the first flange 150 is positioned substantially against the inner wall of the trachea 20 and the second flange 152 is positioned substantially against the exterior wall of the trachea 20. Accordingly, the first and second flanges 150, 152 serve to retain the cannula 144 in the trachea wall, as well as provide an additional barrier between the two environments (e.g., one sterile, one non-sterile). In one embodiment, the cannula 144 includes an anchor device for retaining the cannula 144 in place, similar to certain devices described herein with reference to certain controller housing or electrode embodiments. Example anchor devices may include, but are not limited to, one or more hooks, barbs, studs, suture, staples, adhesives, or any combination thereof.

Upon implanting the cannula 144 in the trachea wall, one or more electrical leads are passed into the patient's airway from the subcutaneously implanted controller housing, through the subcutaneous tunnel, and through the cannula orifice 148. Alternatively, the electrical lead may be orally or nasally inserted into the patient's airway, as described with reference to other embodiments herein, and are passed from within the airway, through the cannula 144, through the subcutaneous tunnel, and to the subcutaneously implanted controller housing. In other embodiments, however, one or more electrical leads are pre-inserted into the cannula and carried through the trachea 20 concurrent with implanting the cannula 144. In another embodiment, the electrical lead is implanted through an aperture formed in the trachea and the cannula 144 is subsequently passed over the electrical lead for implantation.

Figure 17A:
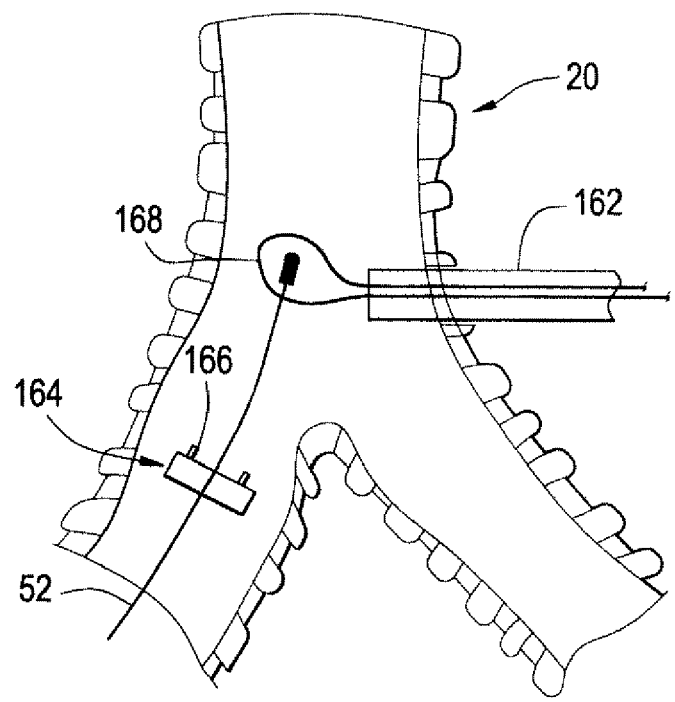
FIGS. 17A-17B are diagrams of an illustrative cannula implantable within a trachea or bronchus according to one embodiment of the invention.
Figure 17B:
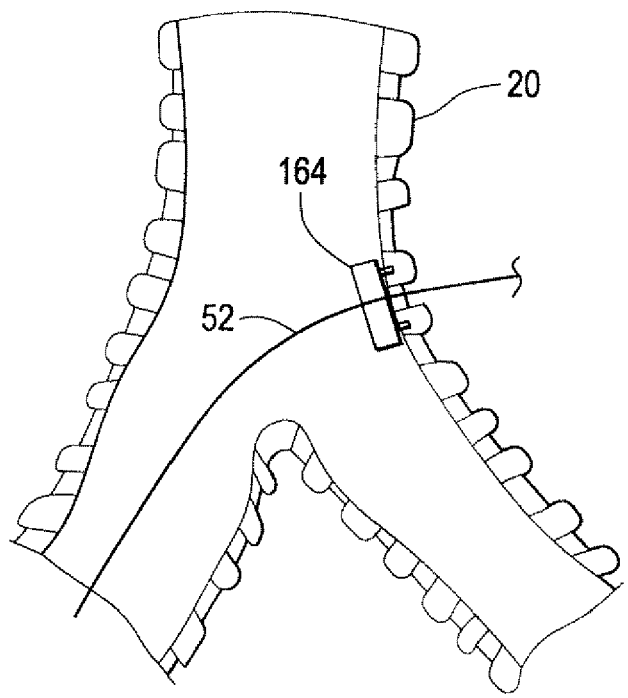

FIGS. 17A-17B illustrate a cross section of one embodiment of a cannula that may optionally be affixed to the inner or exterior wall of the trachea or bronchus around an aperture formed therein, and represent illustrative stages in a method for implanting the cannula. FIG. 17A illustrates a cannula 164 integrated with an electrical lead 52, such that the electrical lead 52 passes through the cannula 164. This cannula 164 is formed in a disk-like shape having an orifice extending therethrough. The cannula 164 may serve as a flange for mounting or affixing to the inner wall of the trachea 20 around the aperture. Similar to the cannula described with reference to FIG. 15, an inner membrane may also extend across the orifice for retaining the electrical lead or leads and to provide an additional seal. The electrical lead 52 slides within the cannula 164 to allow for adjustment and freedom of movement during positioning and implantation of the electrode, the controller housing, and the cannula. The cannula 164 may further include one or more anchor devices 166, similar or identical to other anchor devices described herein.

The electrical lead 52 may first be orally or nasally inserted into the patient's airway having the cannula 164 thereon. As illustrated in FIG. 17A, a delivery device 162 is passed from the subcutaneous tunnel through the aperture formed in the trachea wall. A retrieval tool 168, such as, but not limited to, a lasso, snare, forceps, hook and eye, and the like, is passed through a lumen of the delivery device 162 into the airway. The retrieval tool 168 is adapted to grasp the proximal end of the electrical lead 52 and pull it through into the delivery device 162 lumen. After receiving the proximal end of the electrical lead 52, the delivery device 162 is pulled through the aperture in the trachea 20 until the cannula 164 affixes to the trachea's 20 inner wall. Affixed to the inner wall, optionally by one or more anchor devices 166, the cannula 164 retains the one or more electrodes passing therethrough, as well as substantially seals the aperture formed in the trachea, excluding passage of air or biological fluids between the airway and the thoracic cavity.

FIG. 17B illustrates the cannula 164 anchored to the inner wall of the trachea 20 by anchor devices 166. As is shown, the electrical lead passes from within the airway, through the cannula 164, and to a subcutaneously implanted controller housing. In another embodiment, the cannula 164 is affixed to the exterior wall of the trachea, and the electrical lead 52 and electrode are implanted by passing the delivery device 162 through the cannula 164 and into the airway, and passing the electrical lead 52 therethrough to the selected implantation position within the bronchi.

While the embodiments described in FIGS. 16A-16C and 17A-17B include implanting a cannula in the trachea, in other embodiments, a cannula may be implanted at a point in the bronchus, for example, in the left primary bronchus or the right primary bronchus, using similar methods. Cannula designs and methods other than those described herein may be employed to aid in the retention of electrical leads and sealing the thoracic cavity from the airway. For example, certain embodiments may not include a cannula, but may allow the one or more electrical leads to pass directly through the aperture formed in the trachea or bronchus wall. Furthermore, in other embodiments, other means for sealing the aperture may be used, such as an adhesive, a membrane, suturing, or stapling, for example.

In embodiments in which one or more devices are passed from within the airway to a subcutaneous position within the body, contamination from within the airway may be prevented and/or treated to promote a more sterile environment. For example, in some embodiments, the electrode, electrical lead, cannula, or other device may be covered with a sterile sleeve prior to subcutaneous insertion from the trachea. In other embodiments, the electrode, electrical lead, cannula, or other device may be treated (e.g., coated) with an antimicrobial material, such as antiseptic and/or antibiotic agent. Furthermore, the patient may be treated with antibiotics, steroids, or other pharmaceutical agents systemically or by inhalation, prior to and/or after the implantation procedure. Devices, such as electrodes, leads, or a controller housing implantable within the airway may be similarly coated or treated to prevent infection and scarring within the airway.

Wireless Tissue Interface

Figure 18:
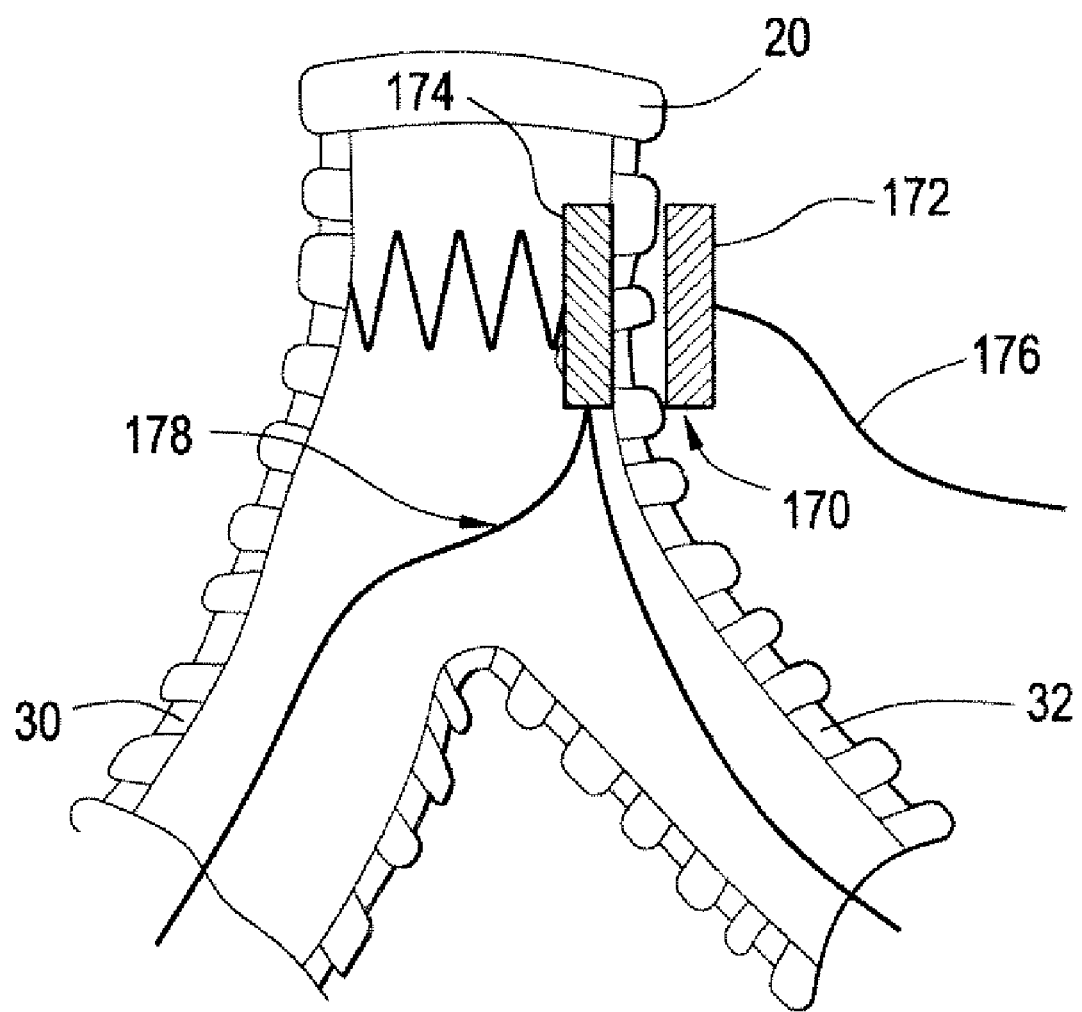
FIG. 18 is a diagram of an illustrative tissue interface according to one embodiment of the invention.

As described, one embodiment may include a tissue interface adaptable for wirelessly communicating one or more electrical signals between the pulse generator and the electrodes implanted within the bronchi, rather than forming an aperture in the trachea or bronchus. FIG. 18 illustrates a cross section of an example of a tissue interface 170 operable for wireless communication, according to one embodiment. In one example, the tissue interface 170 is formed as two components—an exterior interface 172 and an interior interface 174. The exterior interface 172 is adaptable to couple with one or more subcutaneous lead portions 176 attachable to a subcutaneously implantable controller housing. The subcutaneous lead portion 176 is implantable within a subcutaneous tunnel formed between the implantation site of the controller housing, for example near the pectoral region, and a junction 142 at a point on the trachea 20 or bronchus 30, 32 for wirelessly communicating electrical signals to and from one or more airway lead portions 178 positioned within the airway. Accordingly, the airway lead portion 178 is adaptable to couple to the interior interface 174 at its proximal end. In another embodiment, the exterior interface 172 and the interior interface 174 are integrated with the distal end of the subcutaneous lead portion 176 and the proximal end of the airway lead portion 178, respectively. The lead portions 176, 178 and the tissue interface 170 may be implanted by any implantation methods described herein.

As described herein, the interior interface 174 and the exterior interface 172 may be affixed to the inner and outer walls of the airway by anchoring devices similar to certain devices described herein with reference to the controller housing or electrode embodiments. For example, the anchoring device may utilize one or more hooks, barbs, studs, suture, staples, adhesive, or any combination thereof. In another embodiment, the interior interface 174 and the exterior interface 172 may be affixed to the inner and outer walls of the airway by magnetic fixation, such as by integrating or affixing polar opposite magnets to the interior interface 174 and the exterior interface 172.

Electrical signals may be wirelessly communicated across the tissue interface by electromagnetic induction, for example. However, other wireless means for transmitting electrical signals may be employed, such as radio frequency, ultrasonic, infrared, or other electromagnetic waves. For example, the exterior interface 172 and the interior interface 174 may each have a wireless transmitter and receiver operable to communicate wirelessly through protocol, such as radio frequency, microwave, infrared, for example. Further, in this embodiment, the interior interface 174 may include electronic circuitry, a power source, hardware, and/or software for receiving and transmitting wireless communications from and to the pulse generator, and for generating electrical stimulation pulses or performing sensing functions. Thus, in this embodiment, electrical stimulation or sensing functions is divided, with at least some of the electrical stimulation signals being generated within the airway, for example within the interior interface 174 and at least some of the logic for determining timing, delay, magnitude, and the like of signals occurring within the subcutaneously implanted pulse generator. Furthermore, at least part of the sensing functions may be performed within the airway and communicated wirelessly to through the tissue interface 170 to the controller housing.

In another embodiment, the interior interface 174 need not include a power source. For example, the energy required to operate the device may be transmitted through a tissue interface 170 adapted to operate similar to an electrical transformer including a primary coil in the exterior interface 172 and a secondary coil in the interior interface 174. Generating an oscillating current in the primary coil will then induce a current in the secondary coil, as is known. In certain embodiments having a primary and secondary coil, the current may be coded to allow communicating information in the current, such as signals or commands to the interior interface 174. In one embodiment, the interior interface 174 includes electronic circuitry for receiving the current, optionally decoding the information transmitted thereby, and for generating electrical signals, such as for stimulation or sensing.

In another embodiment, such as is described below with reference to FIGS. 25A-25B, the electronic circuitry for performing stimulation and/or sensing are integrated within or near the electrode carried by the airway lead 174. In yet other embodiments, at least one or both of the subcutaneous lead 176 or the airway lead 174 may be unnecessary. Instead, wireless communications may be sent directly from a pulse generator (e.g., implanted subcutaneously, implanted within the trachea or bronchus, or residing external to the patient) to one or more wireless electrodes implanted within the airway. As described in more detail with reference to FIGS. 25A-25B, wireless electrodes include electronic circuitry, a power source, hardware, and/or software for receiving and transmitting wireless communications and for generating electrical stimulation pulses and/or performing sensing functions.

V. Method of Implanting a Pulse Generator Subcutaneously

In one aspect, the system may include at least one electrode implantable within a patient's airway, for example the primary, secondary, or tertiary bronchus, or the bronchioles, and a controller housing containing a pulse generator implantable subcutaneously and external to the patient's airway. Various techniques may be performed to implant an electrode within the airway or to implant the controller housing subcutaneously. For example, techniques similar to those described herein with reference to FIGS. 10 and 11 may be performed to position and implant the one or more electrodes. Additional methods are described for implanting a controller housing subcutaneously, external to the patient's airway.

Figure 19:
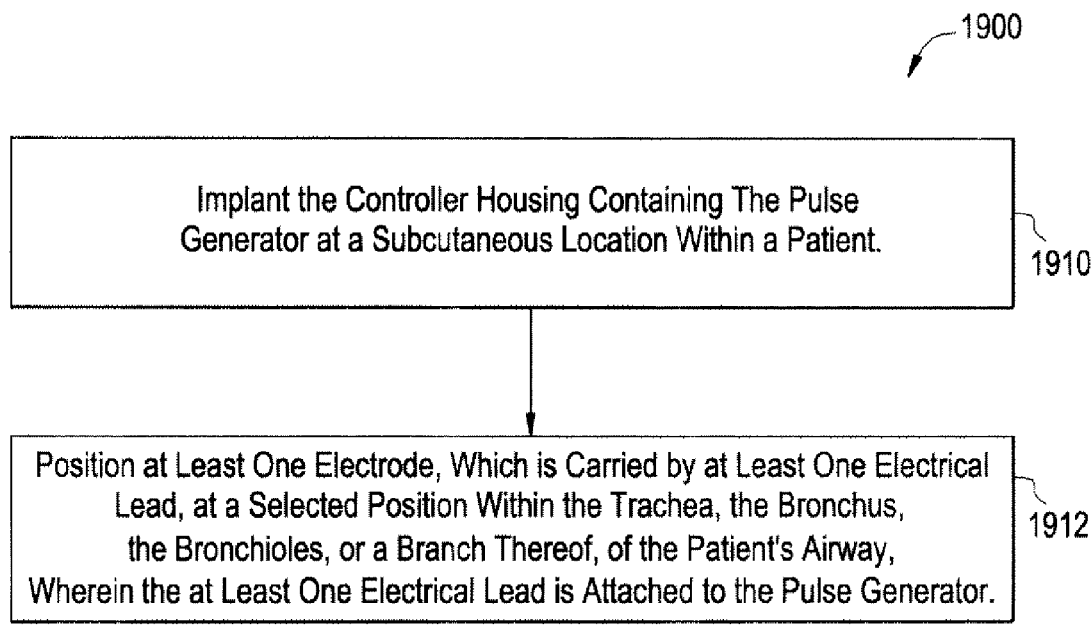
FIG. 19 is a flowchart of an illustrative method of implanting a diaphragm pacing device according to one embodiment of the invention.

FIG. 19 illustrates a flowchart 1900 describing one example of a method for implanting an implantable diaphragmatic stimulation system including a controller housing and at least one electrode carried by at least one lead, such as the embodiments described with reference to FIGS. 15-18.

The method begins at block 1910. At block 1910 the controller housing is implanted subcutaneously. An incision is made and the controller housing may be implanted in a manner similar to methods used for commercially available implantable controller housings, as are known. The controller housing may be any illustrative controller housing operable to perform electrical stimulation or sensing of diaphragmatic, pulmonary, or any other physiologic functions, such as the embodiment described with reference to FIG. 14.

Block 1912 follows block 1910, in which at least one electrode carried by an electrical lead is positioned at an implantation site within the trachea or the bronchi. The electrical lead may be deployed from the controller housing through an aperture formed in the trachea or bronchus. Alternatively, the electrical lead may be inserted through the patient's oral or nasal cavity, and deployed through the trachea to the selected implantation position in the airway, such as is described with reference to FIG. 12. The electrode may be any illustrative electrode embodiment as described herein, such as any of the embodiments described with reference to FIGS. 8A-8G. As described herein, some embodiments may include more than one electrode; thus, each electrode is positioned at its implantation site within the bronchi at block 1912 of this illustrative method. The order of placement of electrodes within the bronchi for embodiments including more than one electrode may be at least partially dependent upon factors such as each electrode's placement relative to other electrodes or the criticality or immediacy of each electrode's purpose. A delivery device, such as a catheter, endoscope, or other device having an elongated lumen suitable for deploying medical devices, may be used to deploy the electrode and lead through the airway and to the implantation site. The delivery device may be inserted into the airway through the aperture formed in the trachea or bronchus or may be inserted orally or nasally into the airway. In one embodiment, an imaging technique known in the art, such as, but not limited to, fluoroscopy, computed tomography, magnetic resonance imaging, x-ray, ultrasound, or position emission tomography may also be performed to assist in the deployment and positioning of the electrode.

Each electrode positioned within the airway is fixed within the airway to retain the electrode at the desired implantation site and to improve electrical coupling. The electrode or electrodes may be fixed within the airway in any manner described herein, such as with reference to FIG. 11.

Each electrical lead carrying an electrode is coupled to the pulse generator to enable electrical communication therebetween. Accordingly, in one embodiment, an electrical lead deployed by way of a delivery device passing through the catheter may already pass through a subcutaneous tunnel created from the controller housing to the aperture in the trachea or bronchus, and may simply be attached to the controller housing if not already coupled. In another embodiment, however, the electrical lead may have been inserted orally or nasally into the airway. For this embodiment, the lead is snared or otherwise pulled through the aperture formed in the trachea, through the subcutaneous tunnel, and attached to the subcutaneously implanted controller housing. This step is optional, and may not be required for certain embodiments. For example, in some embodiments, the electrical lead or leads are permanently affixed to the controller housing. In other embodiments, wireless communication is used instead of electrical leads.

The steps described herein need not be performed in the exact order as presented. For example, in some implantation methods, the electrodes may be positioned and anchored prior to implanting the controller housing. In another example, the electrical leads may be attached to the controller housing prior to implanting the controller housing, the electrodes, or both.

Figure 20:
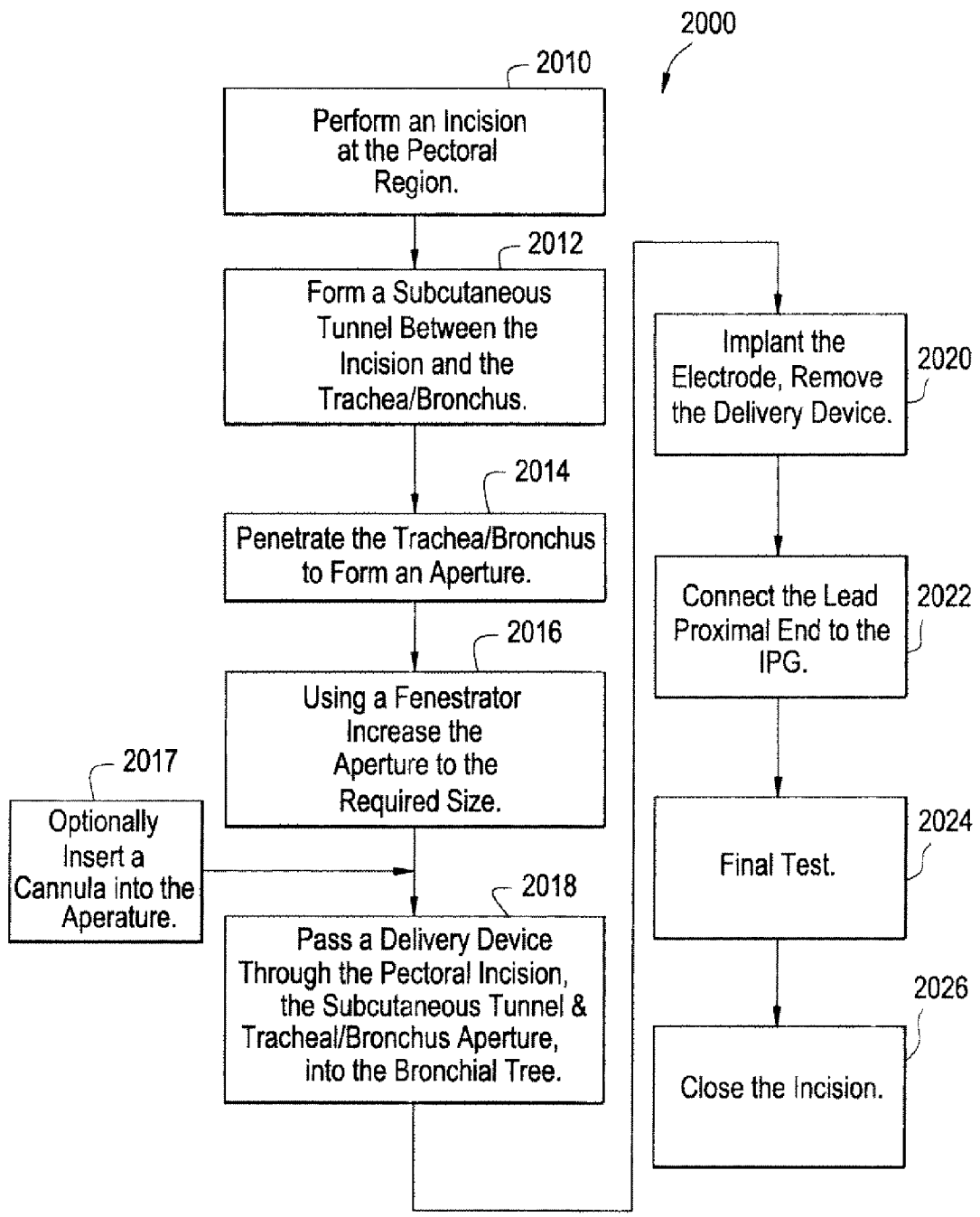
FIG. 20 is a flowchart of an illustrative method of implanting a diaphragm pacing device according to one embodiment of the invention.

FIG. 20 illustrates a flowchart 2000 describing one method for implanting a controller housing of a diaphragmatic stimulating device subcutaneously, for example at or near the pectoral region, according to another embodiment, such as described with reference to FIGS. 14-17.

The method begins at block 2010. At block 2010 an incision is made through the patient's epidermis and dermis for implanting the controller housing at the controller housing implantation site. In one embodiment, the incision is made at or near the patient's pectoral region. However, the incision may be made at any another area suitable for access to the implantation site.

Block 2012 follows block 2010, in which a subcutaneous tunnel is formed between the controller housing implantation site and a point on either the trachea or the bronchus, for example the left or right primary bronchus, using a tunneling device and procedure as known in the art. The subcutaneous tunnel allows one or more electrical leads to pass subcutaneously from the controller housing to the trachea or bronchus. Accordingly, the subcutaneous tunnel has a diameter large enough at least for the electrical lead or leads to exist therein, and optionally large enough for an electrode delivery device, such as a catheter, to pass therethrough. The size of the subcutaneous tunnel may be adjusted by changing the size of the tunneling device or by subsequent enlarging procedures using the tunneling device, for example.

At block 2014, following block 2012, the trachea or bronchus is penetrated and an aperture formed therein for passing the one or more electrical leads therethrough and into the patient's airway. A point of penetration may be determined using one or more imaging and/or guiding technologies, as described herein, or by palpation. In one embodiment, the aperture is formed between cartilage rings. According to one embodiment, the point of penetration is accessed, and the aperture formed, from the subcutaneous tunnel and into the airway. In another embodiment, the penetration is made from within the trachea or bronchus and into the subcutaneous tunnel. The penetration may be made and the aperture formed using a needle, wire, spike, blade, forceps, and the like, which may optionally be inserted through a delivery device, such as a catheter, to the point of penetration.

Following block 2014 is block 2016 in which the size of the aperture is adjusted, based on the intended electrode configuration for the device. The passage diameter may be increased using a fenestrator, catheter tip, forceps, blade, tunneling device, or other suitable device for forming or opening an aperture in a human lumen. As described with reference to FIGS. 15-17, a cannula optionally may be implanted in the aperture, or affixed to the exterior and/or inner wall, of the trachea or bronchus at block 2017.

At block 2018, following block 2016, a delivery device is guided to and positioned substantially near the selected electrode implantation position within the patient's airway. In one embodiment, the delivery device is guided from the subcutaneous tunnel, through the aperture (and optionally the cannula), and into the airway to the implantation site. In another embodiment, however, the delivery device is inserted orally or nasally. The delivery device may be guided and positioned substantially near the selected implantation site using methods similar to those described with reference to FIG. 11 describing electrode implantation, and may optionally be positioned using imaging techniques or other guiding technologies.

Block 2020 follows block 2018, in which the electrical lead carrying the one or more electrodes is inserted through the delivery device, deployed to the implantation site, and the electrode is fixed therein. Upon positioning the delivery device at the implantation site, the electrical lead and electrodes may be fixed in the same manner as described with reference to FIG. 11. Upon implantation of the one or more electrodes, the delivery device may be removed through the trachea or bronchus aperture and the subcutaneous tunnel, or through the oral or nasal cavity, depending upon initial insertion method.

Block 2022 follows block 2020, in which each electrical lead carrying an electrode is coupled to the pulse generator to enable electrical communication therebetween. The electrical leads may be coupled to the controller housing in the same manner as is described with reference to FIG. 19. This step is optional and may not be required for certain embodiments. For example, in some embodiments, the electrical lead or leads may be permanently affixed to the controller housing. In other embodiments, wireless communication may be used instead of electrical leads.

At block 2024, following block 2022, the electrode testing procedures for testing at least one of the positioning of the electrode, the functionality of the electrode, or the electrical coupling of the electrode may be performed in the same manner as is described with reference to FIG. 13. Furthermore, if the embodiment includes an aperture formed in the trachea or bronchus and a cannula implanted therein, the positioning, stability, and seal of the cannula may be optionally tested at this step.

Following block 2024, after the testing procedures are performed, the incision is closed and the implantation method is completed at block 2026.

These steps need not be performed in the exact order as presented. For example, in some implantation methods, the electrodes may be positioned and anchored prior to implanting the controller housing. In another method, the electrical leads may be attached to the controller housing prior to implanting the controller housing, the electrodes, or both. In yet another method, the testing procedures may be performed after implanting each electrode or after implanting a cannula, for example.

Figure 21:
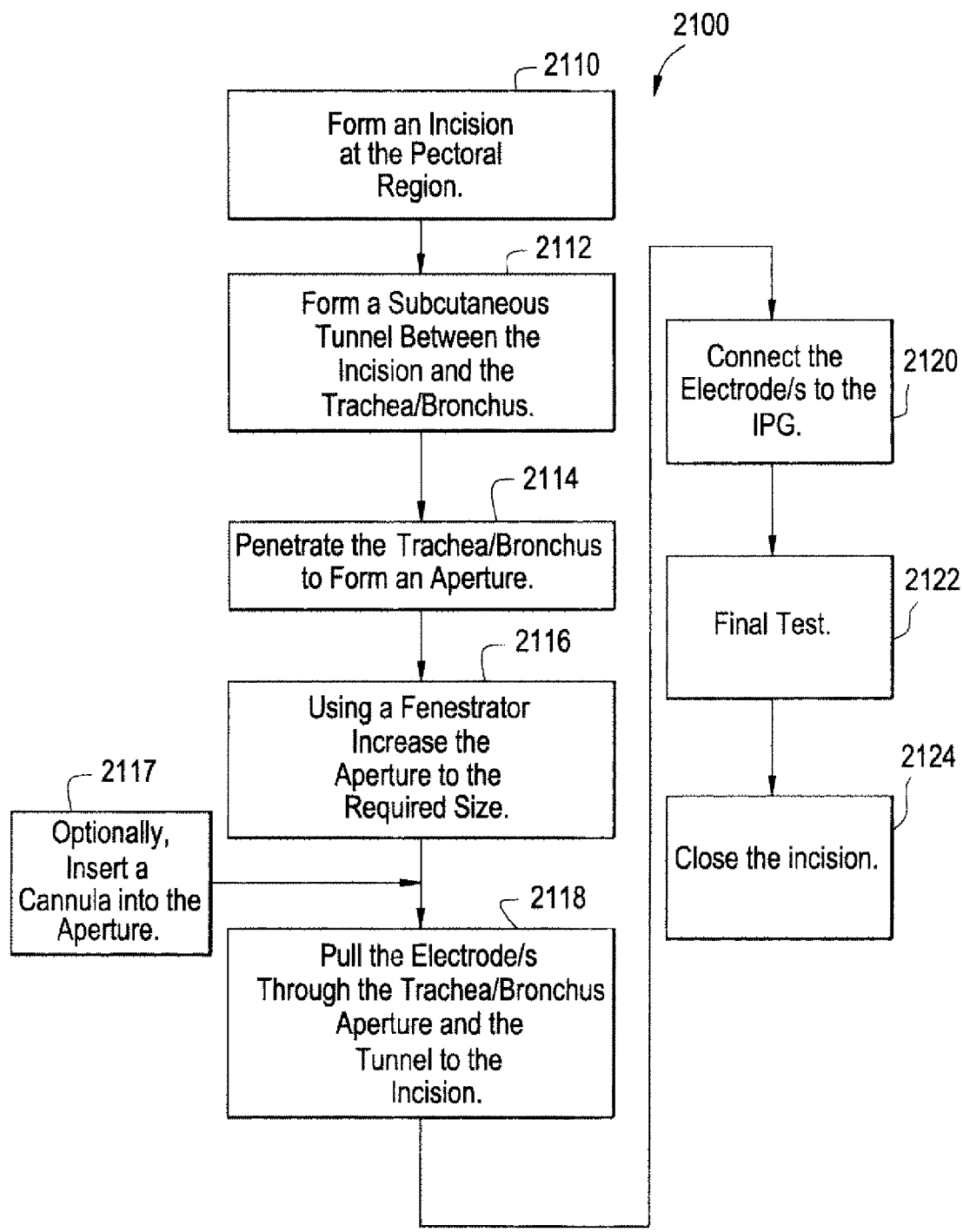
FIG. 21 is a flowchart of an illustrative method of implanting a diaphragm pacing device according to one embodiment of the invention.

FIG. 21 illustrates a flowchart 2100 describing another suitable method for implanting a controller housing subcutaneously, for example, at or near the pectoral region, and pulling one or more electrical leads from within the trachea or bronchus, according to various embodiments, such as those described with reference to FIGS. 14-17.

The method may begin at block 2110. The steps performed at blocks 2110-2117 may be performed in a substantially similar manner as the steps described with reference to blocks 2010-2017 of FIG. 20. However, for the implantation method described with reference to FIG. 21, the electrical leads may be implanted through an oral or nasal cavity, in a substantially similar manner as is described with reference to FIG. 11. Upon implantation, the electrical leads remain within the airway.

Block 2118 follows block 2117, in which a retrieval catheter, and/or a retrieval tool is used to grasp the proximal end of the electrical lead within the airway and pull the lead through the aperture to attach to the subcutaneously implanted controller housing, such as is described with reference to FIGS. 17A-17B. An endoscope, such as a bronchoscope or laryngoscope, or other visualization, imaging, or guiding techniques, may aid in grasping and retrieving the electrical lead by the retrieval tool. As described above with reference to FIG. 20, in one embodiment, the trachea or bronchus is penetrated from within the airway to form the aperture, rather than from within the subcutaneous tunnel. In another embodiment, the proximal end of the electrode or electrodes remain external to the patient, for example passing out of the patient's oral or nasal cavity.

The retrieval tool is passed through the aperture from the subcutaneous tunnel and out of the same orifice, allowing the grasping or temporary coupling of the electrical lead to be performed externally. Upon grasping, the retrieval tool is pulled through the aperture and the subcutaneous tunnel, for attachment of the electrical lead with the controller housing. In another embodiment, the retrieval tool is initially inserted through the patient's airway, such as through the oral or nasal cavity, and then through the aperture into the subcutaneous tunnel for deploying and attaching the electrical lead to the controller housing. In one embodiment that includes a cannula, such as the cannula described with reference to FIGS. 17A-17B, the cannula is affixed to the inner or exterior wall of the trachea or bronchus when the electrical lead is pulled, as described more completely with reference to FIGS. 17A-17B.

The steps performed at blocks 2120-2124 may be performed in a substantially similar manner as the steps described with reference to blocks 2022-2026 of FIG. 20.

VI. Method of Electrically Stimulating a Thoracic Diaphragm

Figure 22:
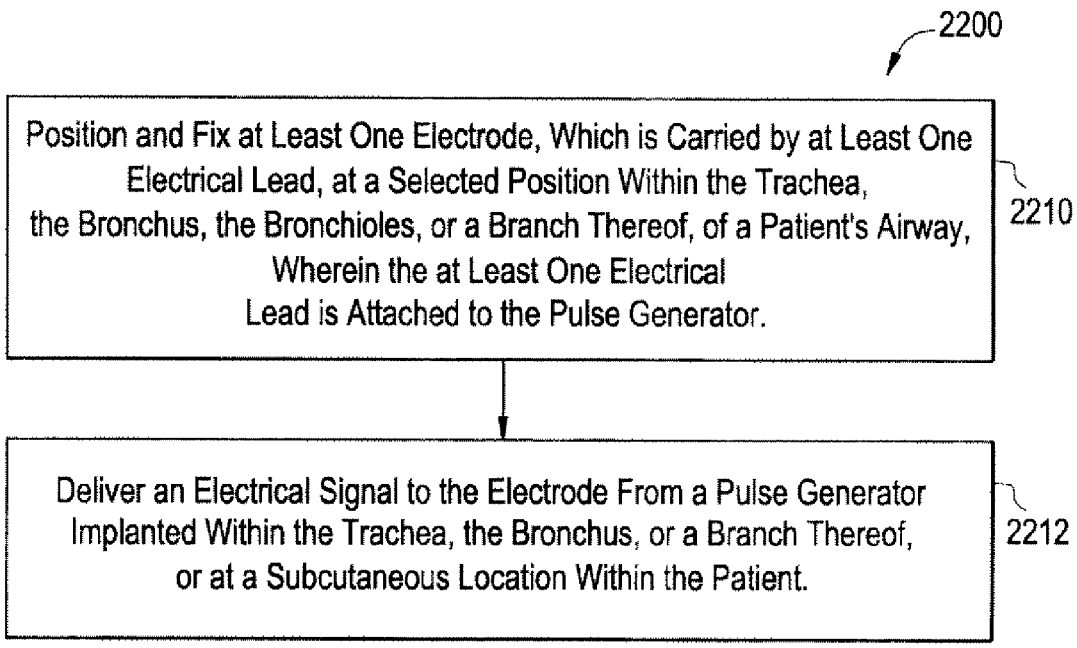
FIG. 22 is a flowchart of an illustrative method of electrically stimulating a diaphragm according to one embodiment of the invention.

FIG. 22 illustrates a flowchart 2200 describing one method for stimulating a patient's diaphragm using a representative implantable diaphragmatic stimulation system as described herein, such as those described with reference to FIGS. 2, 9A-9D, 14, 23, and 25A-25B.

The method begins at block 2210. At block 2210, at least one electrode is positioned and fixed at a selected position within the patient's trachea, primary, secondary, or tertiary bronchus, bronchioles, or any branch thereof within a patient's airway. The one or more electrodes may be carried by one or more electrical leads, respectively, which are attached to a controller housing including a pulse generator implanted within the patient. The electrode and electrical lead may be positioned and fixed by illustrative methods and devices described herein, such as those described with reference to FIGS. 8A-8K, 10, and 11.

Following block 2210 is block 2212, in which an electrical stimulation signal is delivered from the pulse generator. As described herein, the pulse generator may be housed within the control housing and implantable within the patient's airway, such as the trachea or primary bronchus, implantable subcutaneously external to the patient's airway, such as within the pectoral region, or may reside external to the patient, such as is described with reference to FIG. 23 or 25A-25B. The electrical stimulation signal may be effective for performing diaphragmatic pacing (e.g., for providing or supplementing ventilation assistance therapy), diaphragm stimulation for controlling the intra-abdominal pressure for helping to expel vomit, feces, and urine from the body, or for controlling the pressure on the esophagus as it passes through the esophageal hiatus for preventing acid reflux, or any combination thereof.

VII. Electrodes and Electrical Leads Attachable to an External Pulse Generator

In one embodiment, a controller housing including a pulse generator may reside external to the patient, and at least one electrical lead carrying at least one electrode fixable within the trachea or bronchi may be introduced through the patient's mouth or nasal cavity. FIG. 23 illustrates one embodiment of a diaphragmatic stimulation system having a controller housing 262 including a pulse generator 261 that resides external to the patient's body and is in electrical communication with at least one electrode implantable within the bronchi. Thus, the diaphragmatic device of this embodiment minimizes the components implanted within the body and does not require an invasive surgical procedure for implantation of the controller housing 262 or the electrical leads and electrodes. For example, one or more electrical leads 52 carrying one or more electrodes may be introduced to the patient's airway through the nasal cavity or the mouth in a procedure similar to those performed for intubation, bronchoscopy, and the like.

The pulse generator 261 of this embodiment is operable to perform some or all of the same functions described herein, such as those with reference to FIG. 2 describing a pulse generator implanted within an airway. For example, the pulse generator 261 can perform electrical stimulation through the one or more attachable electrical leads and electrodes, such as is used to perform diaphragmatic pacing, phrenic nerve stimulation, diaphragm stimulation for controlling the intra-abdominal pressure for helping to expel vomit, feces, and urine from the body, or for controlling the pressure on the esophagus as it passes through the esophageal hiatus for preventing acid reflux. In one embodiment, the pulse generator 261 is also operable to sense or measure diaphragmatic electrical activity, other diaphragmatic activity, breathing, lungs movement, and/or other physiological parameters.

As used with this embodiment, the pulse generator 261 may be a conventional controller used for operating conventional implantable diaphragmatic pacing systems such as the NeuRx DPS™ by Synapse Biomedical Inc. (Oberlin, Ohio), or a conventional phrenic nerve stimulator, such as the Avery Breathing Pacemaker System, by Avery Biomedical Device, Inc. (Commack, N.Y.), or any commercially available other pulse generator. However, the electrical circuitry, software, and hardware of the pulse generator 261 may be altered or adapted for operation with electrodes implantable within the airway, as compared to conventional implantable pulse generators used with electrodes in direct contact with the phrenic nerve or the thoracic diaphragm.

The pulse generator 261 is electrically coupled to at least one electrical lead 52, carrying at least one electrode. The electrode or electrodes may be positioned at or near the distal end of the electrical leads 52, as illustrated in FIG. 14, for example. However, in other embodiments, one or more electrodes may be positioned at other points distanced from the electrical lead's 52 distal end. The device illustrated in FIG. 23 includes two electrodes 54, 55 implantable at the distal portions of the tertiary bronchi, each connected to a different electrical lead 52, in a similar manner as is described with reference to FIG. 2. In other embodiments, an externally placed pulse generator may communicate wirelessly to one or more electrodes implanted at one or more other positions within the patient's trachea or bronchi, implanted within the patient's GI tract, implanted subcutaneously, and/or affixed externally.

In another embodiment, the pulse generator 261 may be operated with one or more internally implanted electrodes (not shown), such as phrenic nerve cuff electrodes or conventional diaphragm electrodes, and/or with one or more external electrodes, such as one or more external patch electrodes 260, such as may be used as a reference electrode positioned proximal to the patient's diaphragm, or as an external defibrillation electrode or external heart pacing electrode. The external patch electrode 260 may include additional sensing components, for example, but not limited to, a sensing electrode for monitoring electrocardiograms or any other physiological electrical signal, a breathing monitor, an activity monitor, a motion sensor, an accelerometer, a microphone, an ultrasonic sensor for monitoring echo or imaging of the body, a temperature sensor, a heart rate sensor, a blood pressure monitor, or any combination thereof.

Figure 24A:
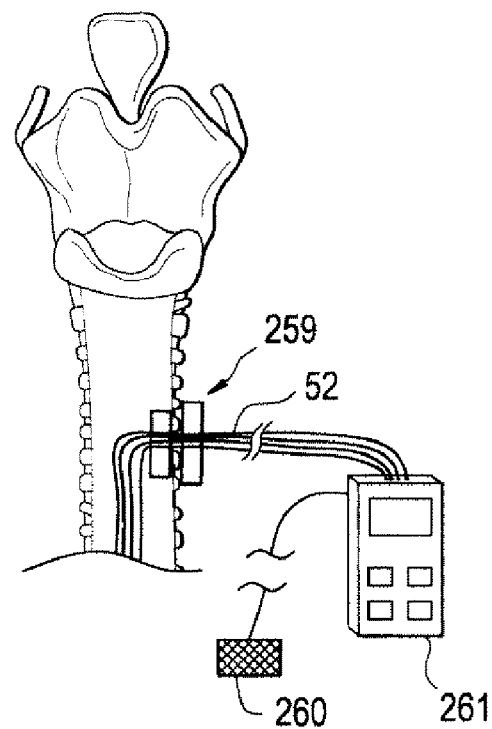
FIGS. 24A-24B are schematic diagrams of an illustrative placement of an electrical lead according to some embodiments of the invention.
Figure 24B:
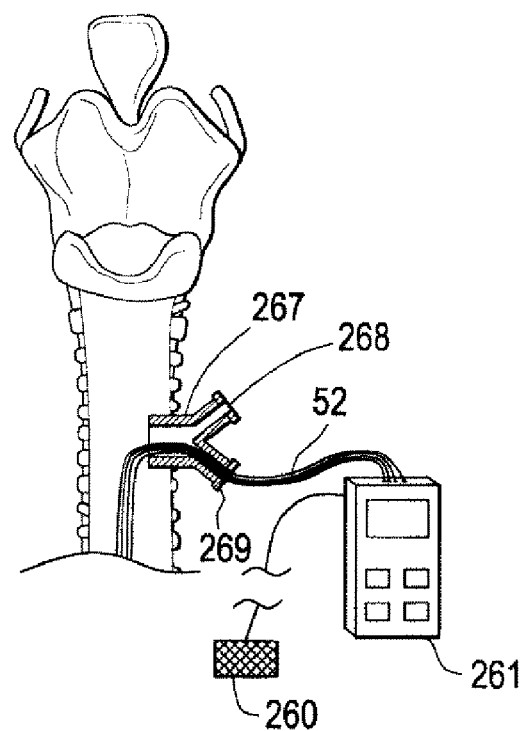

FIGS. 24A-24B illustrate another embodiment of a system including electrical leads and electrodes implantable within a patient's airway and connectable to an external controller housing 262 including a pulse generator 261. One difference between this embodiment and those illustrated and described with reference to FIG. 23 is that the electrical leads 52 exit the body via an artificial exit port, such as the single trachea access stoma 259 illustrated in FIG. 24A or the multiple trachea access stoma 267 illustrated in FIG. 24B, rather than a natural exit, such as orally or nasally. Some of the patients who may benefit from diaphragmatic stimulation or other treatments described herein may already have an artificial access to their trachea, such as may be used for mechanical ventilation to bypass the upper airway or for other medical indications. Various techniques are described herein to deploy and retrieve electrical leads and electrodes implantable within the airway. Any of these methods may also be used with the embodiments illustrated in FIGS. 24A-24B to deploy electrical leads carrying electrodes through an existing or then created artificial tracheal access, which may decrease the procedure complexity, reduce associated risks, and may allow stimulating the diaphragm, the phrenic nerve, or other nerves even for treatments where stimulation is provided only for a limited time (e.g., temporary treatment), or for short durations (e.g., minutes to hours) during the day and night.

With reference to FIG. 24A, an example of a single tracheal access stoma 259, which may be used deploy electrical leads 52 into the airway. The electrical leads 52 may be connected to an external pulse generator 262, such as is described with reference to FIG. 23. The single tracheal access stoma 259 may also be used to administer other therapies to the patient, including mechanical ventilation or a by-pass to the upper airway. These therapies may be administered simultaneously with, or sequential to, the electrical stimulation, such as diaphragmatic stimulation.

FIG. 24B illustrates another embodiment for providing access through a patient's trachea including a multiple tracheal access stoma 267, which includes at least two entrance ports. This multiple tracheal access stoma 267 allows administering multiple therapies via an existing single tracheal access. In the example illustrated in FIG. 24B, the electrical leads 52 are deployed to the trachea via a first access port 269 while a second access port 268 is available to administer another therapy. For example, the second access port 269 may be used to provide mechanical ventilation in parallel to the electrical stimulation, or as a safety measure to provide ventilation of the patient in case electrical stimulation fails or any other reason in which ventilation is not sufficient. A mechanical ventilation system may be connected to a sensor for monitoring ventilation (not shown) including blood oxygen saturation, breathing, blood pressure, vitality, or any other sensor or monitor for detecting or measuring ventilation or perfusion. In one embodiment, the mechanical ventilation system may be connected to the multiple tracheal access stoma 267 while delivering diaphragm pacing or phrenic nerve stimulation, whereby the mechanical ventilation system is on standby and ready to administer therapy or is operable to administer mechanical ventilation therapy in concert with diaphragmatic pacing or phrenic nerve pacing. In one embodiment, the mechanical ventilation system may by automatically activated based at least in part on comparing a measured ventilation or perfusion to a predefined value or level of ventilation or perfusion. Though, in other embodiments, the mechanical ventilation system may be manually operated.

VIII. Wireless Electrodes in Communication with an External Pulse Generator

Figure 25A:
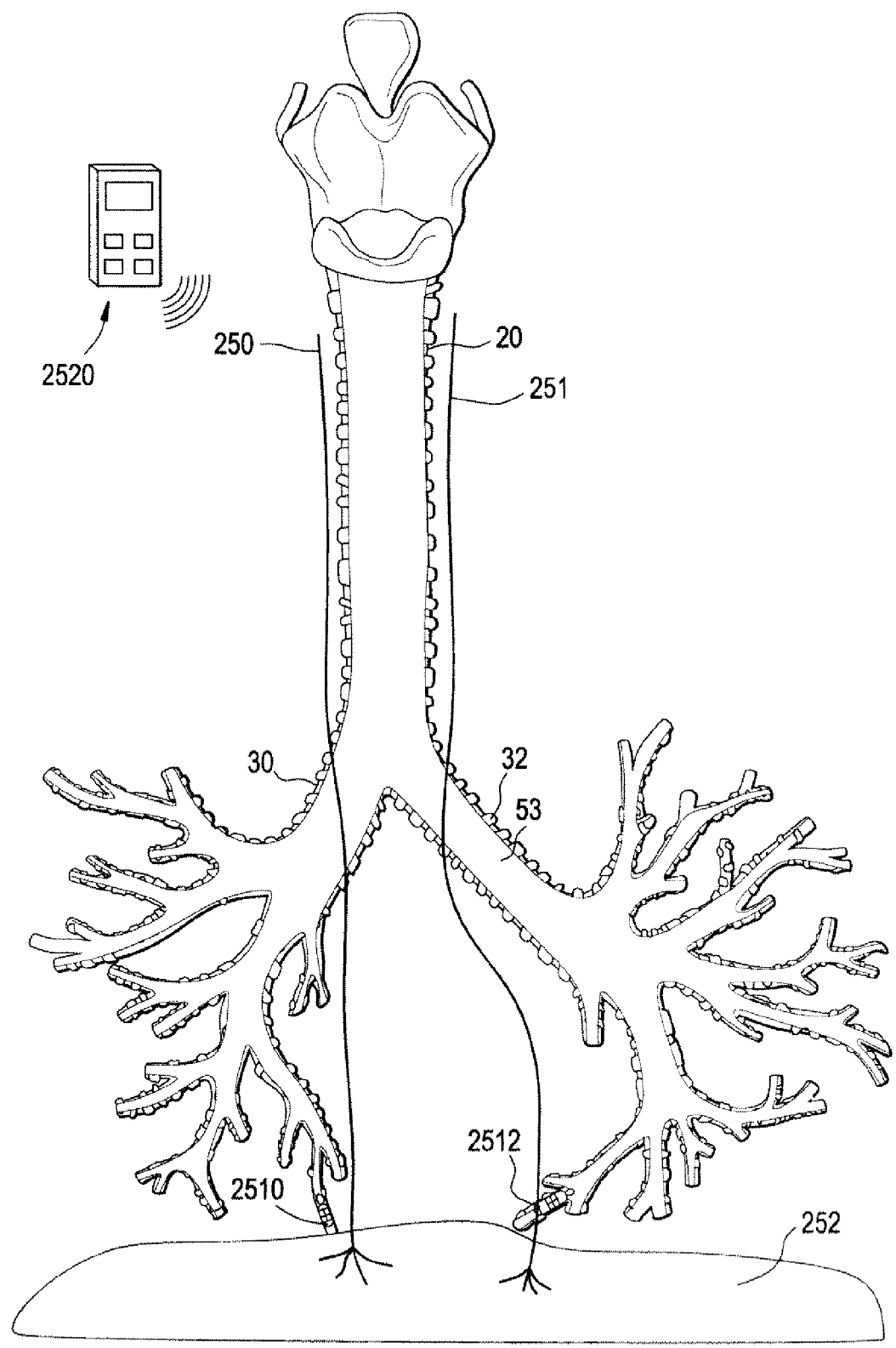
Figure 25B:
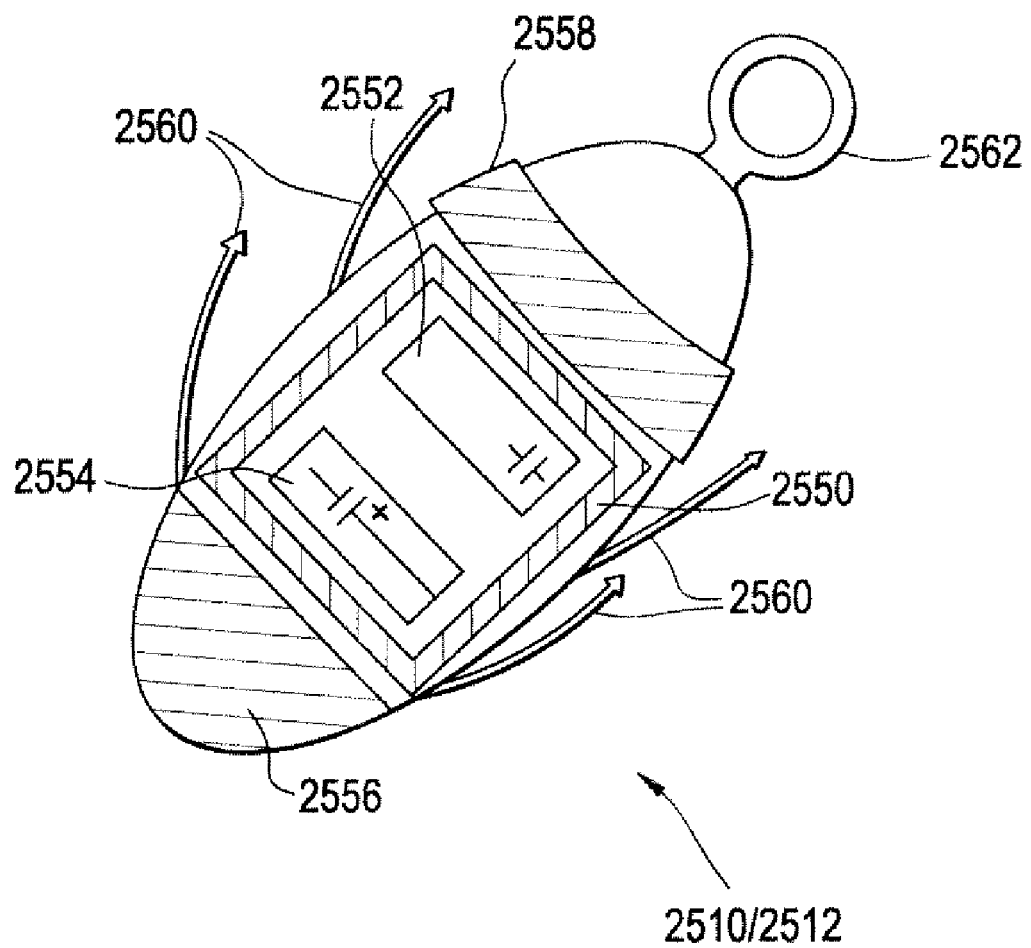

FIGS. 25A-25B illustrate an embodiment of a diaphragmatic stimulation device that incorporates one or more wireless electrodes in lieu of, or in addition to, wired electrodes utilizing electrical leads. FIG. 25A illustrates two wireless electrodes 2510, 2512 implanted in the right and left tertiary bronchi in proximity to the right and left sides of the diaphragm 252, respectively. It is appreciated, however, that any other electrode placement may be implemented with wireless electrodes, such as, but not limited to, those described with reference to FIGS. 2, 9A-9D, and 23. As illustrated, this embodiment is operable to perform diaphragmatic pacing, such as dual pacing of the diaphragm left and right sides or single side pacing performed by electrode 2510 or by electrode 2512, and optionally sensing by the other electrode not delivering a stimulation signal. The use of wireless electrodes and an externally positioned pulse generator minimizes the number of implanted components, thereby simplifying the implantation procedure and minimizing risk of infection, patient discomfort, or device failure due to stress (e.g., on electrical leads).

The wireless electrodes 2510, 2512 are in wireless communication with an externally positioned pulse generator 2520, which may be similar to that described with reference to FIG. 23, but operable to communicate wirelessly, transmitting to and/or receiving signals from the implanted wireless electrodes 2510, 2512. It is appreciated, however, that any other pulse generator configurations may be implemented, such as those implanted within the patient's airway or subcutaneously. Any means for wirelessly communicating between the pulse generator 2520 and the wireless electrodes 2510, 2512, and for causing generation and delivery of one or more electrical stimulation signals by one or more wireless electrodes, may be implemented by the pulse generator's controller hardware, software and/or firmware, such as, but not limited to, via radio frequency ("RF"), magnetic, or acoustic telemetry. In one example embodiment, RF communication means can be employed, such that the pulse generator 2520 and the wireless electrodes 2510, 2512 include RF transmitter/receiver hardware (e.g., coil, antenna, passive, active, etc.), whereby the pulse generator 2520 transmits control commands via RF amplitude modulation.

The wireless electrodes 2510, 2512 include a receiver to receive the control commands. The receipt of the RF signal may be used at least in part to power the controller of the wireless electrodes 2510, 2512 (e.g., if a passive receiver). The controller of the wireless electrodes 2510, 2512 includes control logic and means for storing stimulation energy, such as, but not limited to, a discrete capacitor or an electrolytic capacitor, as is known. Upon receiving the control commands, the wireless electrodes 2510, 2512 are operable to discharge the stored stimulation energy and subsequently begin to recharge between commands. Accordingly, a pulse generator 2520 configured to wirelessly cause generation and delivery of electrical stimulation signals via wireless electrodes may not include a capacitor circuit, or other circuitry, to generate stimulation signals by the pulse generator 2520. In various embodiments, the wireless electrodes 2510, 2512 are operable to wirelessly communicate bi-directionally with the pulse generator 2520 (or other devices), such as when used to perform sensing functions and/or as a reference electrode, as described in more detail herein.

FIG. 25B illustrates a wireless electrode, such as the wireless electrodes 2510, 2512 illustrated in FIG. 25A, according to one embodiment. Each wireless electrode 2510, 2512 includes a receiver 2550, a controller 2552, a power source 2554 (unless it is a passive RF device), and a first electrode contact 2556 at or near its distal tip. According to the embodiment illustrated, each wireless electrode 2510, 2512 optionally includes a second electrode contact 2558 separated from the first electrode contact 2556 (e.g., 1-30 mm). In one embodiment, the second electrode contact 2556 is configured in a circular shape, so as to at least partially encircle the diameter of the electrode body. The second electrode contact 2558 may be operable as a sensing or reference electrode, as further described herein, or as a second stimulating electrode. The controller 2552 includes electronic circuitry and optional software and/or firmware for receiving control commands from a pulse generator 2520 and for generating and delivering the desired stimulation signal. As illustrated, the controller 2552 circuitry is intended to encompass the capacitive circuitry operable to generate, store, and discharge stimulation energy. It is appreciated that any capacitive circuitry may be incorporated, as is known.

The power source 2554 for powering the controller 2552 and associated circuitry may be sized according to the intended purpose and duration of implantation. For example, larger stimulation signals and/or longer duration implants may include a larger power source 2554, whereas electrodes intended to be implanted for short periods of time, used infrequently, or for delivering relatively low levels of stimulation energy can include a smaller power source 2554. The power source 2554 can be non-rechargeable batter, a rechargeable battery, or may be passive (e.g., DC power converted from the RF signals received).

With continued reference to FIG. 25B, the wireless electrodes 2510, 2512 may be deployed using any of the methods already discussed herein, such as, but not limited to, via a bronchoscope or a catheter-based delivery system. The body of the wireless electrodes 2510, 2512 may be shaped and sized to fit securely within the intended implantation site. In various embodiments, the wireless electrodes 2510, 2512 range from approximately 1 mm to approximately 10 mm in diameter, and approximately 3 mm to approximately 50 mm in length. In one embodiment, the wireless electrodes 2510, 2512 range from approximately 2 mm to approximately 6 mm in diameter, and approximately 10 mm to approximately 30 mm in length. The body of the wireless electrodes 2510, 2512 may be made from any biocompatible material, such as, but not limited to, metal, polymer, glass, ceramic, or any other building material or combination used for building implantable devices. The wireless electrodes 2510, 2512 illustrated in FIG. 25B also optionally include one or more anchor devices 2560 configured as expandable members, however, any anchor devices described herein, such as those described with reference to FIGS. 3A-3F and 8A-8K, may be used.

Wireless electrodes can be implanted in patients who are expected to receive ventilation therapy for a relatively short period of time (e.g., a few weeks or months). Thus, in one embodiment, the wireless electrodes 2510, 2512 include removal means 2562 for aiding their removal/extraction from the patient's airway. Removal may be performed by a bronchoscope or other catheter-based procedure, for example, and thus the removal means 2562 may include a hook, eye, or other member that can be grasped by a removal tool.

The wireless electrode configurations illustrated in FIG. 25 are provided for illustrative purposes only, and other wireless electrode placements within the bronchi or trachea, or any combinations of those described herein, may also be employed to induce breathing and/or diaphragmatic stimulation and/or sensing. Moreover, according to other embodiments, wireless electrodes positionable in a patient's airway may be used in combination with conventionally implanted electrodes, such as phrenic nerve cuff electrodes or diaphragmatic surgically implanted electrodes, with conventional epidermally placeable electrodes, and/or with mechanical ventilation treatments.

IX. Method of Electrically Stimulating the Diaphragm

Figure 26:
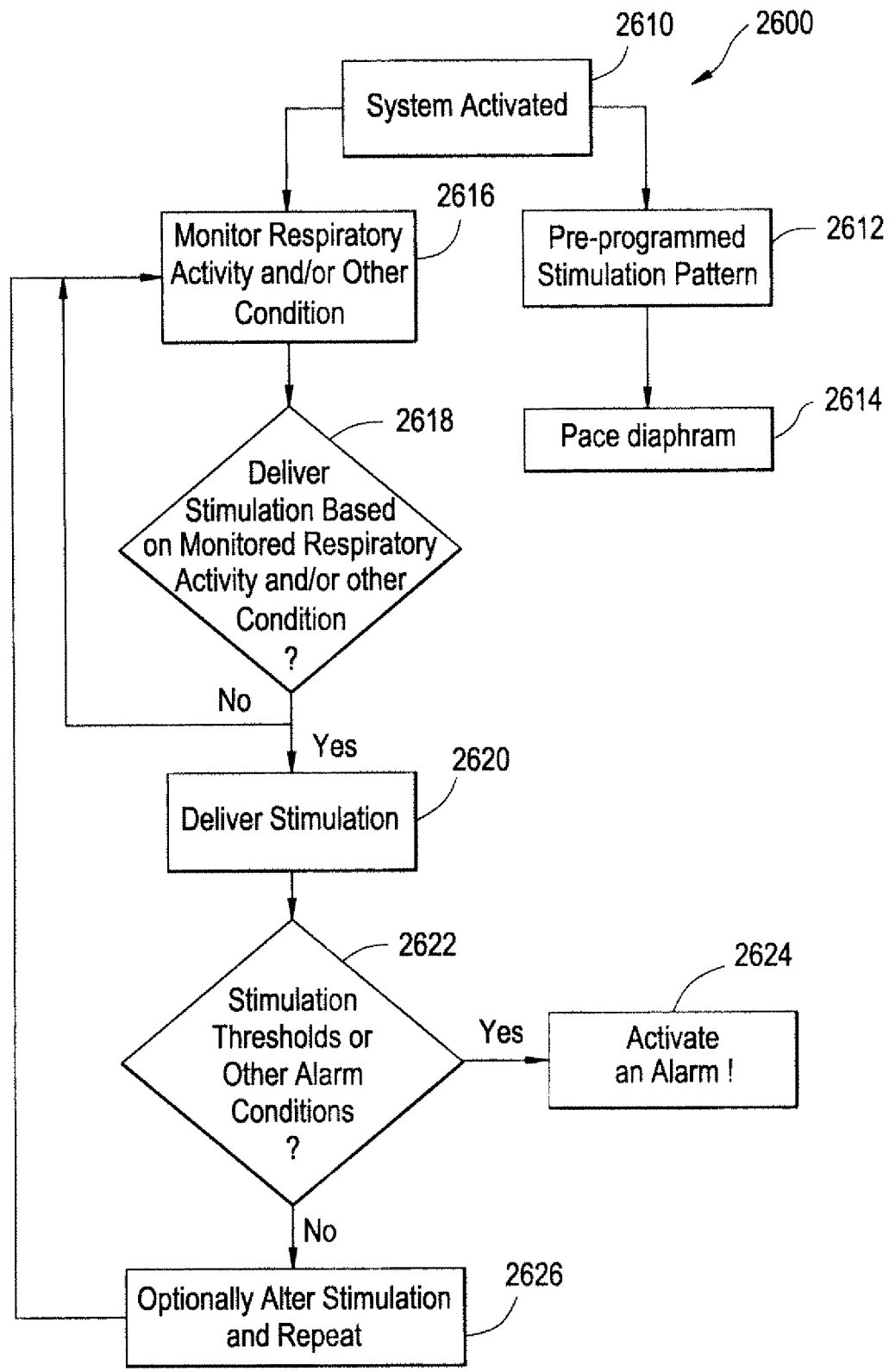
FIG. 26 is a flowchart of an illustrative method of electrically stimulating a diaphragm according to one embodiment of the invention.

FIG. 26 illustrates one embodiment of a method 2600 for stimulating the diaphragm, such as may be described with reference to FIG. 2, 9A, 9C, 9D, 14, 23, 24A, 24B, or 25A, for example. The method 2600 begins at block 2610 in which the diaphragmatic stimulation system is activated (which may also include testing operability of the pulse generator, electrical leads, and/or electrodes). Following block 2610 are blocks 2612 and 2614, in which pre-programmed stimulation patterns are optionally administered for pacing the diaphragm (and/or stimulating the phrenic nerve(s)), or block 2616, in which respiratory activity and/or associated parameters is monitored and analyzed to determine a condition-dependent stimulation pattern for delivering to the patient. Whether pre-programmed stimulation patterns or other condition-dependent stimulation patterns are to be delivered is determined based on the specific implementation of the diaphragmatic stimulation system, and can be programmable using I/O interfaces and/or the communications module of the pulse generator, as described with reference to FIGS. 4-5.

At blocks 2612 and 2614, diaphragm pacing (or other stimulation) is performed based on a pre-programmed stimulation pattern, which may be generated by the pulse generator described in more detail with reference to FIGS. 4 and 5, and delivered to one or more electrical leads carrying one or more electrodes implanted within the patient's airway. Pre-programmed stimulation patterns may include at least some of the following stimulation parameters: stimulation voltage (pattern and amplitude), stimulation current (pattern and amplitude), stimulation pulses repetition rate, pulse shape and width, stimulation duration, stimulation patter including number of cycles, time between cycles, and cycle specific parameters. Pre-programmed stimulation pattern parameters may be stored in a memory associated with the pulse generator, or may be stored in an external system in communication with the pulse generator.

At blocks 2616-2624 a condition-dependent diaphragm pacing stimulation pattern is determined based at least in part on feedback from at least one sensor or other input monitoring respiratory activity or other condition, such as, but not limited to, patient ventilation (e.g., signals from a mechanical ventilation device), perfusion status, breathing, and/or oxygen saturation. The sensor output representing the monitored respiratory activity or other condition is analyzed at decision block 2618 using an algorithm or other suitable means for determining whether diaphragm pacing is required, such as may be performed by a processor, programmed logic, and other data associated with the controller of the pulse generator, as described in more detail with reference to FIGS. 4 and 5. If it is determined at decision block 2618 that pacing is required, the controller executing the algorithm or other suitable means may determine the appropriate stimulation pattern parameters for administering safe and effective diaphragm pacing (or other stimulation) at block 2620. Any of the pacing and/or other stimulation therapies described herein may be provided by the stimulation signal(s) delivered at block 2620. For example, FIGS. 27A-27B provide detailed examples of stimulation patterns that are administered in relation to a patient's breathing patterns and administered mechanical ventilation therapy to supplement the mechanical ventilation therapy administered. Specifically, FIG. 27B illustrates an example of a condition-dependent stimulation pattern delivered to a patient by monitoring the patient's spontaneous breathing patterns and additional mechanical ventilation therapy administered.

Following block 2620 are blocks 2622-2626, in which thresholds or other alarm conditions are analyzed to determine whether to continue delivering therapy and/or to signal an alarm (or other control action in response to the condition identified). At decision block 2622, any stimulation thresholds (e.g., energy thresholds, time thresholds, etc.), or other stimulation conditions, that are set in the controller logic are analyzed to determine whether stimulation can continued to be delivered or whether it should be halted and an alarm generated at block 2624 (or any other control action, such as halting operation, administer different therapy, etc.). If it is determined at decision block 2622 that stimulation should be continued, then block 2626 follows, in which the stimulation signal is optionally altered and the process repeats to block 2616. Any stimulation pattern parameters may be adjusted at block 2626, including, but not limited to, stimulation voltage (pattern and amplitude), stimulation current (pattern and amplitude), stimulation pulses repetition rate, pulse shape and width, stimulation duration, stimulation patter including number of cycles, time between cycles, and/or cycle specific parameters. Accordingly, the method 2600 of FIG. 26 illustrates example methods for operating diaphragmatic stimulation devices described herein to provide stimulation therapy and optionally include a feedback loop based on sensed and/or monitored conditions.

FIGS. 27A-27B provide detailed examples of stimulation patterns that are administered in relation to a patient's breathing patterns and administered mechanical ventilation therapy to supplement or replace mechanical ventilation therapy administered. For example, the diaphragmatic stimulation system can be utilized to administer ventilation therapy to a patient with respiratory impairments in place of conventional mechanical ventilation methods. Though, in another example, the diaphragmatic stimulation system may instead supplement conventional mechanical ventilation therapy, delivered intermittently to assist weaning the patient from the mechanical ventilation, which is achieved by the electrical stimulation of the diaphragm, or delivered when a mechanical ventilation system fails. For example, stimulation may be administered delivering therapy by the diaphragmatic stimulation system over a predefined period of time (e.g., several minutes up to several hours) for every few breathing cycles (e.g., 3 out of every 12 in one minute) in lieu (or optionally in combination with) mechanical ventilation being delivered. In yet another example embodiment, the diaphragmatic stimulation system may be used independent of a conventional mechanical ventilation therapy being administered to facilitate further strengthening the diaphragm (and optionally the costal muscles). It is appreciated that any combination of diaphragmatic stimulation and mechanical ventilation therapy may be administered, including only diaphragmatic stimulation, predetermined patterns of mechanical and diaphragmatic stimulation, diaphragmatic stimulation based on feedback of mechanical stimulation, diaphragmatic stimulation based on patient breathing patterns, diaphragmatic stimulation at the same time as mechanical ventilation, and the like.

FIG. 27A illustrates an example embodiment of simulation pattern used in an embodiment delivering a combination of mechanical ventilation with diaphragmatic simulation therapy. The first pattern I illustrates the mechanical ventilation pattern where every fifth mechanical ventilation cycle is omitted. The second pattern II illustrates the diaphragm stimulation signal pattern, in which a stimulation signal is administered at the omitted portions to induce breathing electrically. The third pattern III illustrates the resulting breathing pattern of the patient being administered by the combined mechanical ventilation and diaphragmatic stimulation therapy. The patterns illustrated here are intended to be illustrative only, and any other pattern in which diaphragmatic pacing replaces mechanical ventilation cycles may be delivered. In one example embodiment, the ratio of mechanical ventilation to diaphragmatic pacing may vary from the 5:1 ratio illustrated in FIG. 27A to any ratio between approximately 2,000:1 to approximately 1:1000. In other embodiments, other combinations may include variable ratio of mechanical ventilation to diaphragmatic pacing or a randomized mix of mechanical ventilation to diaphragmatic pacing. Accordingly, in these embodiments, the diaphragmatic stimulation therapy may be provided in conjunction with the convention ventilation therapy, such as may be beneficial to assist weaning a patient from mechanical ventilation therapy and/or to strengthen the patient's diaphragm.

FIG. 27B illustrates another example embodiment of diaphragmatic simulation therapy delivered in combination with mechanical ventilation. In this example, the respiratory therapy to be administered is controlled by one or more sensors monitoring the respiratory activity of the patient, and therapy is delivered only when the system identifies a problem with the patient's spontaneous breathing. The first pattern I illustrates the patient's desired breathing pattern. The second pattern II illustrates the mechanical ventilation therapy administered. The third pattern III illustrates the administered diaphragmatic stimulation pattern, which is dependent upon the patient's spontaneous breathing and/or the administered mechanical ventilation. As can be seen in pattern III, diaphragmatic stimulation was administered about every one or two breathing cycles. However, the duration between the arrows of pattern III shows a larger absence of diaphragmatic stimulation that resulted from sensed breathing by the patient or support from the mechanical ventilator. The fourth pattern IV illustrates the resulting breathing pattern of the patient being administered by the combined mechanical ventilation and diaphragmatic stimulation therapy. In examples monitoring patient's spontaneous breathing, diaphragmatic stimulation is not delivered because the patient's own breathing already causes contraction of the diaphragm, thus providing the desired exercise to avoid atrophy or further strengthen the diaphragm.

Publications cited herein are incorporated by reference. Modifications and variations of the methods and devices described herein will be obvious to those skilled in the art from the foregoing detailed description. Such modifications and variations are intended to come within the scope of the appended claims.

I claim:

1. A method for electrically stimulating a diaphragm, comprising:
    inserting a catheter into a patient's mouth or nasal cavity;
    delivering at least one electrode carried by at least one electrical lead through a lumen in the catheter;
    positioning and fixing the at least one electrode at a selected position within a patient's bronchus in operable proximity to at least one of a thoracic diaphragm or a phrenic nerve, wherein the at least one electrode and at least one electrical lead are in operable electrical communication with a pulse generator housed within a controller housing; and
    delivering at least one electrical stimulation signal from the at least one electrode to at least one of the thoracic diaphragm or the phrenic nerve.

2. The method of claim 1, wherein the catheter comprises an intubation tube.

3. The method of claim 1, wherein the at least one electrode comprises at least one wireless electrode in wireless communication with the pulse generator, and wherein delivering the at least one electrical stimulation signal comprises:
    wirelessly transmitting at least one command from the pulse generator to the at least one electrode;
    generating the at least one electrical stimulation signal at the at least one electrode upon receiving the at least one command; and
    delivering the at least one electrical stimulation signal from the at least one electrode.

4. The method of claim 3, wherein wirelessly transmitting the at least one command comprises transmitting the at least one command utilizing radio frequency communication.

5. The method of claim 3, further comprising:
    sensing at least one condition associated with the patient's respiratory activity; and
    wirelessly transmitting a signal to the pulse generator containing data associated with the at least one condition from the at least one electrode.

6. The method of claim 5, further comprising:
    generating at least one additional command based at least in part on the data associated with the at least one condition;
    wirelessly transmitting the at least one additional command from the pulse generator to the at least one electrode; and
    generating and delivering at least one additional electrical stimulation signal upon receiving the at least one additional command at the at least one electrode.

7. The method of claim 5, wherein the one or more conditions associated with the patient's respiratory activity comprises at least one of: (a) thoracic diaphragm movement; (b) costal muscle movement; or (c) lung movement.

8. The method of claim 1, wherein delivering the at least one electrical stimulation signal comprises delivering at least one electrical stimulation signal effective in diaphragmatic pacing.

9. The method of claim 1, wherein delivering the at least one electrical stimulation signal comprises delivering the at least one electrical stimulation signal to at least one of: (a) the left side of the patient's thoracic diaphragm; (b) the right side of the patient's thoracic diaphragm; (c) the patient's left phrenic nerve; (d) the patient's right phrenic nerve; or (e) any combination thereof.

10. The method of claim 1, further comprising receiving, at the pulse generator, at least one signal indicating an operation of a mechanical ventilation system, wherein delivering the at least one electrical stimulation signal is based at least in part on the at least one signal indicating the operation of the mechanical ventilation system.

11. The method of claim 10, wherein the at least one electrical stimulation signal is effective to perform at least one of: (a) ventilation therapy; or (b) diaphragmatic stimulation to treat muscle atrophy.

* * * * *